United States Patent
Bales, Jr. et al.

(10) Patent No.: US 9,782,217 B2
(45) Date of Patent: Oct. 10, 2017

(54) RADIO FREQUENCY GENERATOR AND METHOD FOR A CORDLESS MEDICAL CAUTERIZATION AND CUTTING DEVICE

(71) Applicant: Covidien AG, Neuhausen am Rheinfall (CH)

(72) Inventors: Thomas O. Bales, Jr., Coral Gables, FL (US); Matthew A. Palmer, Miami, FL (US)

(73) Assignee: COVIDIEN AG, Neuhausen am Rheinfall (CH)

( * ) Notice: Subject to any disclaimer, the term of this patent is extended or adjusted under 35 U.S.C. 154(b) by 522 days.

(21) Appl. No.: 14/180,726

(22) Filed: Feb. 14, 2014

(65) Prior Publication Data

US 2014/0188101 A1 Jul. 3, 2014

Related U.S. Application Data

(63) Continuation-in-part of application No. 12/270,111, filed on Nov. 13, 2008, now Pat. No. 9,050,098, and
(Continued)

(51) Int. Cl.
*A61B 18/12* (2006.01)
*A61B 18/14* (2006.01)
*A61B 17/00* (2006.01)

(52) U.S. Cl.
CPC ...... *A61B 18/1445* (2013.01); *A61B 18/1206* (2013.01); *A61B 2017/00734* (2013.01);
(Continued)

(58) Field of Classification Search
CPC . A61B 18/10; A61B 18/1206; A61B 18/1286; A61B 18/1233; A61B 2018/1266
See application file for complete search history.

(56) References Cited

U.S. PATENT DOCUMENTS

| 2,230,332 A | 2/1941 | Moore |
| 3,041,478 A | 6/1962 | Andrew |

(Continued)

FOREIGN PATENT DOCUMENTS

| DE | 3041478 | 6/1982 |
| EP | 0 623 316 | 11/1994 |

(Continued)

OTHER PUBLICATIONS

Wikipedia, 555 timer IC, Retrieve from https://en.wikipedia.org/wiki/555_timer_IC on May 19, 2016.*
(Continued)

*Primary Examiner* — Jaymi Della
*Assistant Examiner* — Eunhwa Kim

(57) ABSTRACT

A circuit for generating a radio-frequency signal for a surgical device is disclosed. The circuit has a voltage regulator that supplies direct current (DC) voltage, a first MOSFET, a second MOSFET, and a MOSFET driver. The MOSFET driver receives the DC voltage supplied from the voltage regulator and has a local oscillator. The local oscillator switches the first MOSFET and the second MOSFET on and off at a frequency generated by the local oscillator. The circuit further includes a transformer connected to the first and second MOSFETs, having a center tap and a main voltage applied at the center tap, and providing an alternating current (AC) output.

15 Claims, 50 Drawing Sheets

Related U.S. Application Data a continuation-in-part of application No. 12/324,873, filed on Nov. 27, 2008, now Pat. No. 8,758,342, and a continuation-in-part of application No. 12/403,710, filed on Mar. 13, 2009, now Pat. No. 8,491,581, and a continuation-in-part of application No. 12/403,785, filed on Mar. 13, 2009, now Pat. No. 8,377,059, and a continuation-in-part of application No. 12/403,835, filed on Mar. 13, 2009, now Pat. No. 8,328,802, and a continuation-in-part of application No. 13/397,484, filed on Feb. 15, 2012, now Pat. No. 9,532,829.

(60) Provisional application No. 61/792,859, filed on Mar. 15, 2013.

(52) U.S. Cl.
CPC ............. *A61B 2018/1226* (2013.01); *A61B 2018/1266* (2013.01); *A61B 2018/1286* (2013.01); *A61B 2018/1412* (2013.01); *A61B 2018/1455* (2013.01)

(56) References Cited

U.S. PATENT DOCUMENTS

| | | | |
|---|---|---|---|
| 3,613,682 A | 10/1971 | Naylor | |
| 3,886,944 A | 6/1975 | Jamshidi et al. | |
| 4,359,052 A | 11/1982 | Staub | |
| 4,463,759 A | 8/1984 | Garito et al. | |
| 4,563,570 A | 1/1986 | Johns | |
| 4,878,493 A | 11/1989 | Pasternak et al. | |
| 5,080,983 A | 1/1992 | Alexon | |
| 5,133,713 A | 7/1992 | Huang et al. | |
| 5,136,220 A | 8/1992 | Philipp | |
| 5,149,603 A | 9/1992 | Fleming et al. | |
| 5,207,697 A | 5/1993 | Carusillo | |
| 5,276,306 A | 1/1994 | Huffman | |
| 5,364,392 A * | 11/1994 | Warner | A61B 18/1206 606/33 |
| 5,372,596 A | 12/1994 | Klicek | |
| 5,401,273 A | 3/1995 | Shippert | |
| 5,455,499 A | 10/1995 | Uskali et al. | |
| 5,480,409 A | 1/1996 | Riza | |
| 5,514,129 A | 5/1996 | Smith | |
| 5,688,265 A | 11/1997 | Citronowicz | |
| 5,688,269 A | 11/1997 | Newton et al. | |
| 5,717,306 A | 2/1998 | Shipp | |
| 5,720,744 A | 2/1998 | Eggleston et al. | |
| 5,747,953 A | 5/1998 | Philipp | |
| 5,782,397 A | 7/1998 | Koukline | |
| 5,782,821 A | 7/1998 | Couch | |
| 5,792,138 A | 8/1998 | Shipp | |
| 5,792,165 A | 8/1998 | Klieman et al. | |
| 5,814,044 A | 9/1998 | Hooven | |
| 5,817,119 A | 10/1998 | Klieman et al. | |
| 5,849,020 A | 12/1998 | Long et al. | |
| 5,919,203 A | 7/1999 | Husted | |
| 5,929,764 A | 7/1999 | Brink et al. | |
| 5,935,126 A | 8/1999 | Riza | |
| 5,961,514 A | 10/1999 | Long et al. | |
| 5,984,921 A | 11/1999 | Long et al. | |
| 6,013,991 A | 1/2000 | Philipp | |
| 6,084,523 A | 7/2000 | Gelnovatch et al. | |
| 6,093,186 A * | 7/2000 | Goble | A61B 18/1206 606/32 |
| 6,106,524 A | 8/2000 | Eggers et al. | |
| 6,203,541 B1 | 3/2001 | Keppel | |
| 6,225,777 B1 | 5/2001 | Garcia | |
| 6,235,027 B1 | 5/2001 | Herzon | |
| 6,249,706 B1 | 6/2001 | Sobota | |
| 6,293,942 B1 | 9/2001 | Goble | |
| 6,306,160 B1 | 10/2001 | Nidetzky | |
| 6,482,200 B2 | 11/2002 | Shippert | |
| 6,512,348 B1 | 1/2003 | Wellisz | |
| 6,533,778 B2 | 3/2003 | Herzon | |
| 6,551,312 B2 | 4/2003 | Zhang et al. | |
| 6,562,032 B1 | 5/2003 | Ellman et al. | |
| 6,569,163 B2 | 5/2003 | Hata | |
| 6,585,735 B1 | 7/2003 | Frazier et al. | |
| 6,587,731 B1 | 7/2003 | Ingle et al. | |
| 6,645,198 B1 | 11/2003 | Bommannan | |
| 6,666,875 B1 | 12/2003 | Sakurai et al. | |
| 6,682,528 B2 | 1/2004 | Frazier et al. | |
| 6,726,686 B2 | 4/2004 | Buysse et al. | |
| 6,743,229 B2 | 6/2004 | Buysse et al. | |
| 6,767,352 B2 | 7/2004 | Field et al. | |
| 6,796,981 B2 | 9/2004 | Wham et al. | |
| 6,836,688 B2 | 12/2004 | Ingle et al. | |
| 6,860,880 B2 | 3/2005 | Treat et al. | |
| 6,908,463 B2 | 6/2005 | Treat et al. | |
| 6,921,398 B2 | 7/2005 | Carmel et al. | |
| 6,953,461 B2 | 10/2005 | McClurken et al. | |
| 6,960,210 B2 | 11/2005 | Lands et al. | |
| 6,960,894 B2 | 11/2005 | Carusillo et al. | |
| 7,033,351 B2 | 4/2006 | Howell | |
| 7,083,613 B2 | 8/2006 | Treat | |
| 7,083,618 B2 | 8/2006 | Couture et al. | |
| 7,131,971 B2 | 11/2006 | Dycus et al. | |
| 7,147,638 B2 | 12/2006 | Chapman et al. | |
| 7,150,749 B2 | 12/2006 | Dycus et al. | |
| 7,166,103 B2 | 1/2007 | Carmel et al. | |
| 7,179,258 B2 | 2/2007 | Buysse et al. | |
| 7,207,990 B2 | 4/2007 | Lands et al. | |
| 7,241,296 B2 | 7/2007 | Buysse et al. | |
| 7,300,435 B2 | 11/2007 | Wham | |
| 7,303,557 B2 | 12/2007 | Wham et al. | |
| 7,364,577 B2 | 4/2008 | Wham et al. | |
| 7,598,880 B2 | 10/2009 | Powell et al. | |
| 7,805,263 B2 | 9/2010 | Mack | |
| 2002/0115997 A1 | 8/2002 | Truckai | |
| 2002/0165541 A1 | 11/2002 | Whitman | |
| 2003/0109778 A1 | 6/2003 | Rashidi | |
| 2003/0125735 A1 | 7/2003 | Herzon | |
| 2003/0144680 A1 | 7/2003 | Kellogg et al. | |
| 2003/0181898 A1 * | 9/2003 | Bowers | A61B 18/1206 606/34 |
| 2003/0220638 A1 | 11/2003 | Metzger | |
| 2004/0006335 A1 | 1/2004 | Garrison | |
| 2004/0010250 A1 | 1/2004 | Manna et al. | |
| 2004/0012370 A1 | 1/2004 | Miller | |
| 2004/0092992 A1 | 5/2004 | Adams et al. | |
| 2004/0095107 A1 | 5/2004 | Kernahan | |
| 2004/0116952 A1 | 6/2004 | Sakurai et al. | |
| 2004/0167513 A1 | 8/2004 | Hilal | |
| 2005/0010212 A1 | 1/2005 | McClurken et al. | |
| 2005/0096661 A1 | 5/2005 | Farrow et al. | |
| 2005/0159752 A1 | 7/2005 | Walker et al. | |
| 2005/0174809 A1 * | 8/2005 | Lipcsei | H02M 3/33592 363/16 |
| 2005/0215994 A1 | 9/2005 | Solomon | |
| 2005/0234442 A1 | 10/2005 | Spears | |
| 2005/0273091 A1 * | 12/2005 | Booth | A61B 18/12 606/41 |
| 2006/0089637 A1 | 4/2006 | Werneth et al. | |
| 2006/0116675 A1 | 6/2006 | McClurken et al. | |
| 2006/0142751 A1 | 6/2006 | Treat | |
| 2006/0178670 A1 | 8/2006 | Woloszko | |
| 2006/0189981 A1 | 8/2006 | Dycus | |
| 2006/0206100 A1 | 9/2006 | Eskridge et al. | |
| 2006/0241589 A1 | 10/2006 | Heim et al. | |
| 2006/0293648 A1 | 12/2006 | Herzon | |
| 2007/0010807 A1 | 1/2007 | Chu | |
| 2007/0049926 A1 | 3/2007 | Sartor | |
| 2007/0049927 A1 | 3/2007 | Saltzman | |
| 2007/0105010 A1 | 5/2007 | Cassidy | |
| 2007/0118107 A1 | 5/2007 | Francischelli et al. | |
| 2007/0166617 A1 | 7/2007 | Gozdz | |
| 2007/0175955 A1 | 8/2007 | Shelton, IV et al. | |
| 2007/0182369 A1 | 8/2007 | Gerber | |
| 2007/0208330 A1 | 9/2007 | Treat et al. | |
| 2007/0225698 A1 * | 9/2007 | Orszulak | A61B 18/1206 606/34 |
| 2007/0233053 A1 | 10/2007 | Shelton, IV et al. | |

(56) References Cited

U.S. PATENT DOCUMENTS

| | | |
|---|---|---|
| 2007/0270790 A1 | 11/2007 | Smith et al. |
| 2008/0009860 A1 | 1/2008 | Odom |
| 2008/0097316 A1 | 4/2008 | Malinin et al. |
| 2008/0114349 A1 | 5/2008 | Treat |
| 2008/0147058 A1 | 6/2008 | Horrell et al. |
| 2008/0167644 A1 | 7/2008 | Shelton et al. |
| 2008/0183028 A1 | 7/2008 | Guillen-Garcia et al. |
| 2008/0251568 A1 | 10/2008 | Zemlok et al. |
| 2008/0251569 A1 | 10/2008 | Smith et al. |
| 2008/0255607 A1 | 10/2008 | Zemlok |
| 2011/0224663 A1* | 9/2011 | Heim ................ A61B 18/1206 606/33 |
| 2012/0265196 A1* | 10/2012 | Turner ............. A61B 17/32009 606/34 |
| 2013/0103023 A1* | 4/2013 | Monson ................... H02J 7/00 606/33 |

FOREIGN PATENT DOCUMENTS

| | | |
|---|---|---|
| EP | 1 199 040 | 4/2002 |
| EP | 1 850 406 | 1/2006 |
| EP | 1769765 | 4/2007 |
| FR | 2230332 | 12/1974 |
| JP | H02-043501 | 9/1990 |
| JP | 11-056866 | 3/1999 |
| JP | 2000-254140 | 9/2000 |
| JP | 2000-254141 | 9/2000 |
| JP | 2000-262533 | 9/2000 |
| JP | 2000-287987 | 10/2000 |
| JP | 2001-017385 | 1/2001 |
| JP | 2002-263109 | 9/2002 |
| JP | 2002-538880 A | 11/2002 |
| JP | 2007-125395 A | 5/2007 |
| WO | 2004030552 A1 | 4/2004 |
| WO | 2007/089603 A2 | 8/2007 |
| WO | 2007-091074 | 8/2007 |

OTHER PUBLICATIONS

Wikipedia, 555 IC timer, Retrieved on Nov. 12, 2016 from https://en.wikipedia.org/wiki/555_timer_IC.*
European Search Report of European Patent App. No. 08 85 5351.
International Search Report of PCT/US08/85061.
Canadian Office Action, Application No. 2706958 dated Apr. 21, 2015.
Notice of Rejection dated Dec. 17, 2013 in Japanese Patent App. No. 2010-536205.
First Examination Report dated Jan. 30, 2013 in Australian Patent App. No. 2008329627.
European Search Report dated May 15, 2013 in European Patent App. No. 13160959.
European Search Report dated May 27, 2013 in European Patent App. No. 13160960.
European Search Report dated May 15, 2013 in European Patent App. No. 13160969.
European Search Report dated May 29, 2013 in European Patent App. No. 13161097.
European Search Report dated May 29, 2013 in European Patent App. No. 13160962.
Japanese Notice of Allowance issued in Appl. No. 2014-241598 dated Jun. 2, 2016.
Japanese Office Aciton and English language translation, issued in Appl. No. JP 2016-131304 dated May 31, 2017.

* cited by examiner

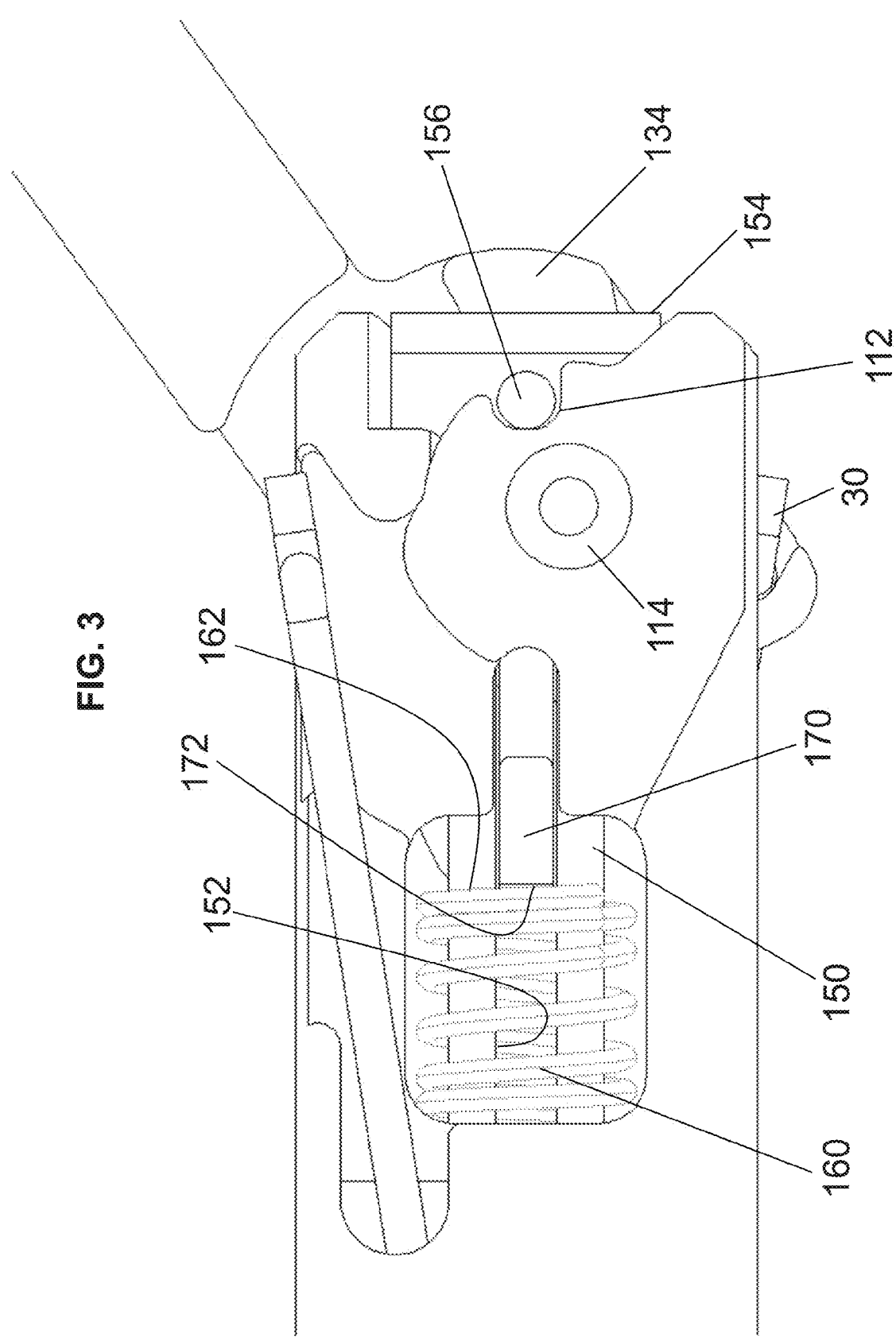

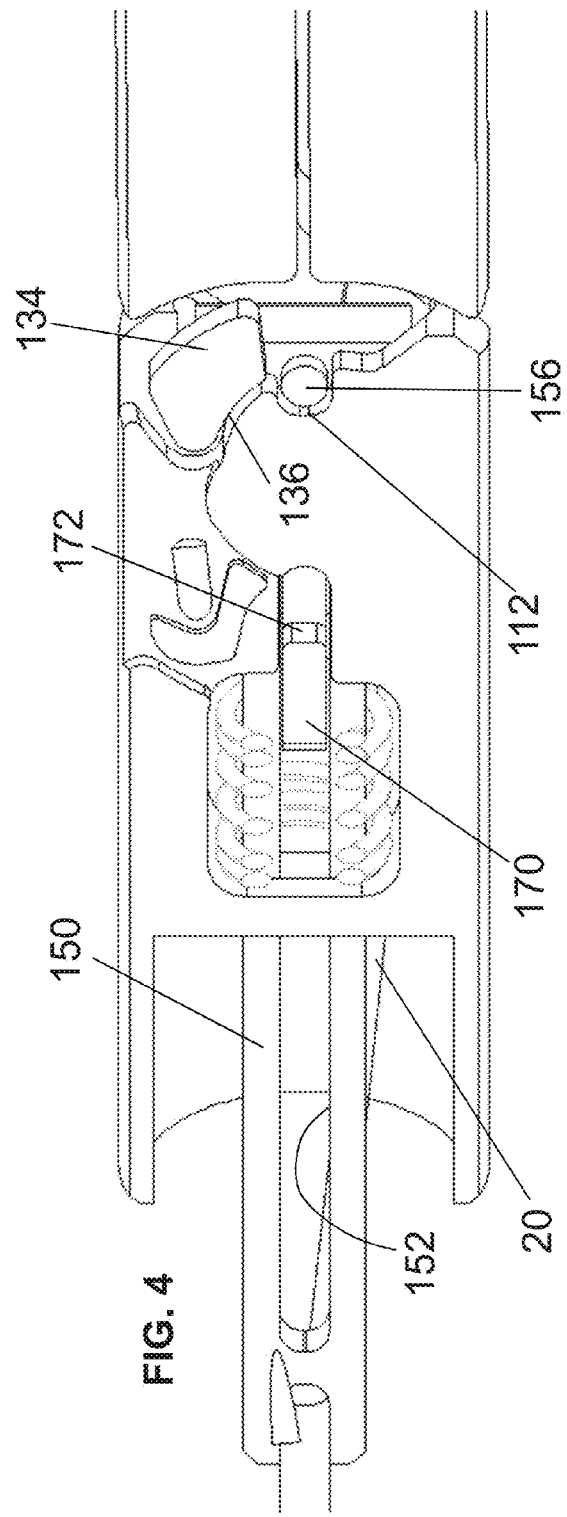
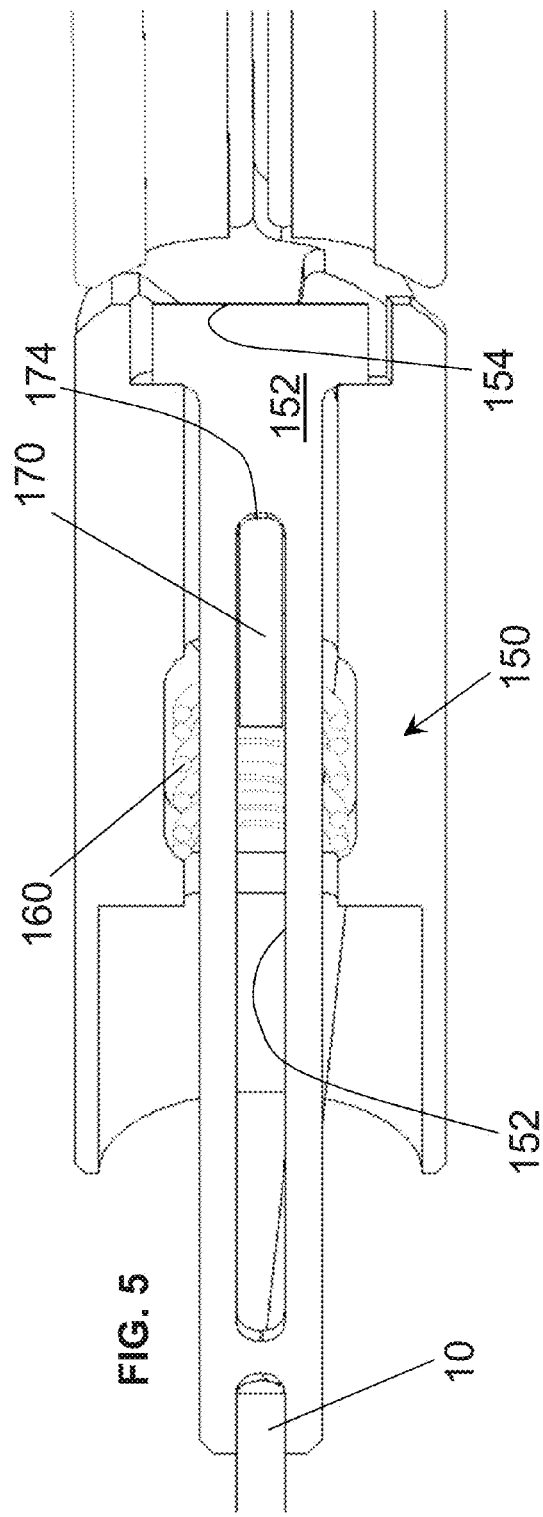

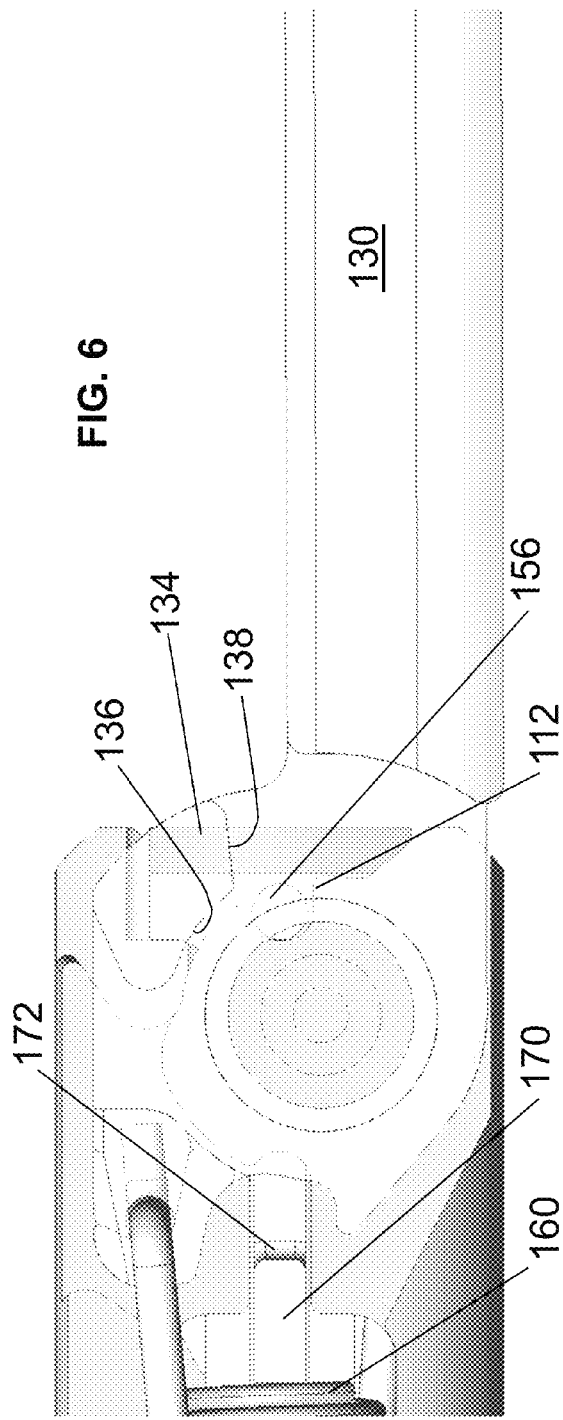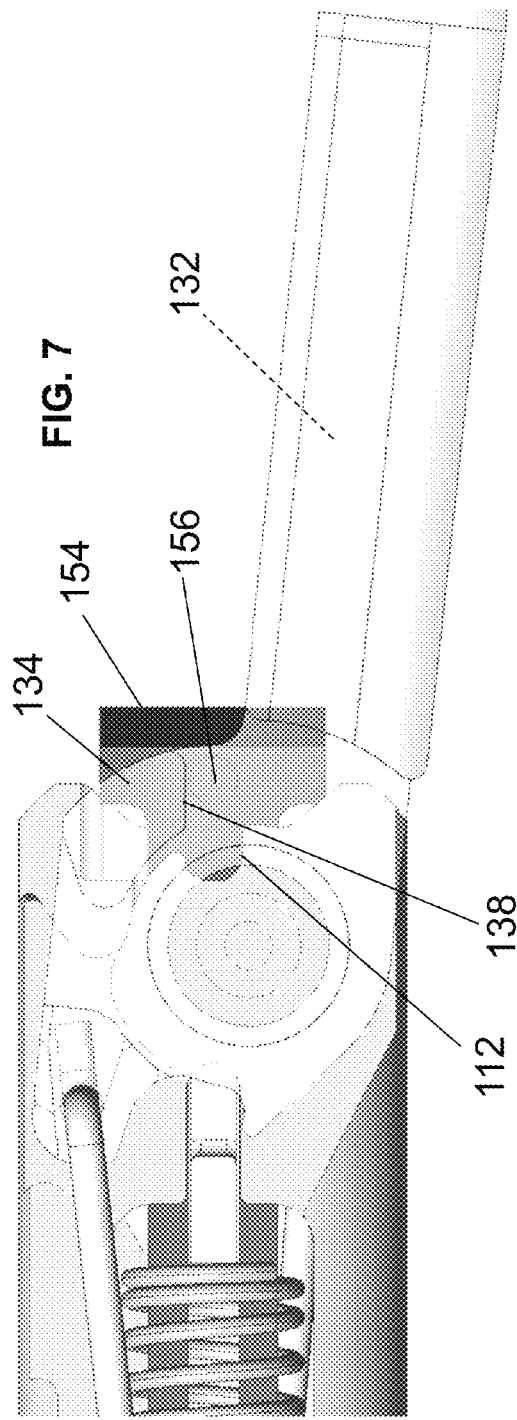

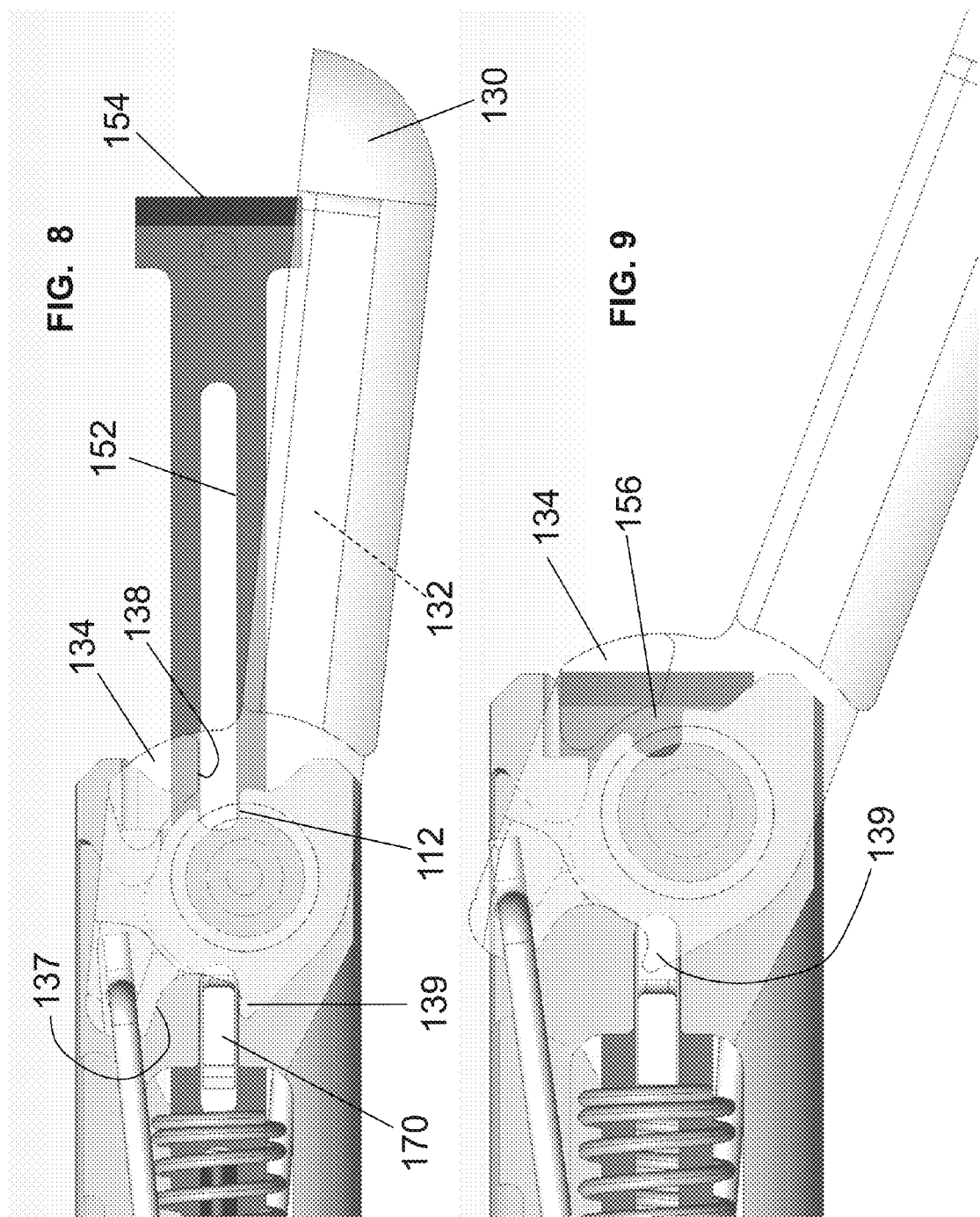

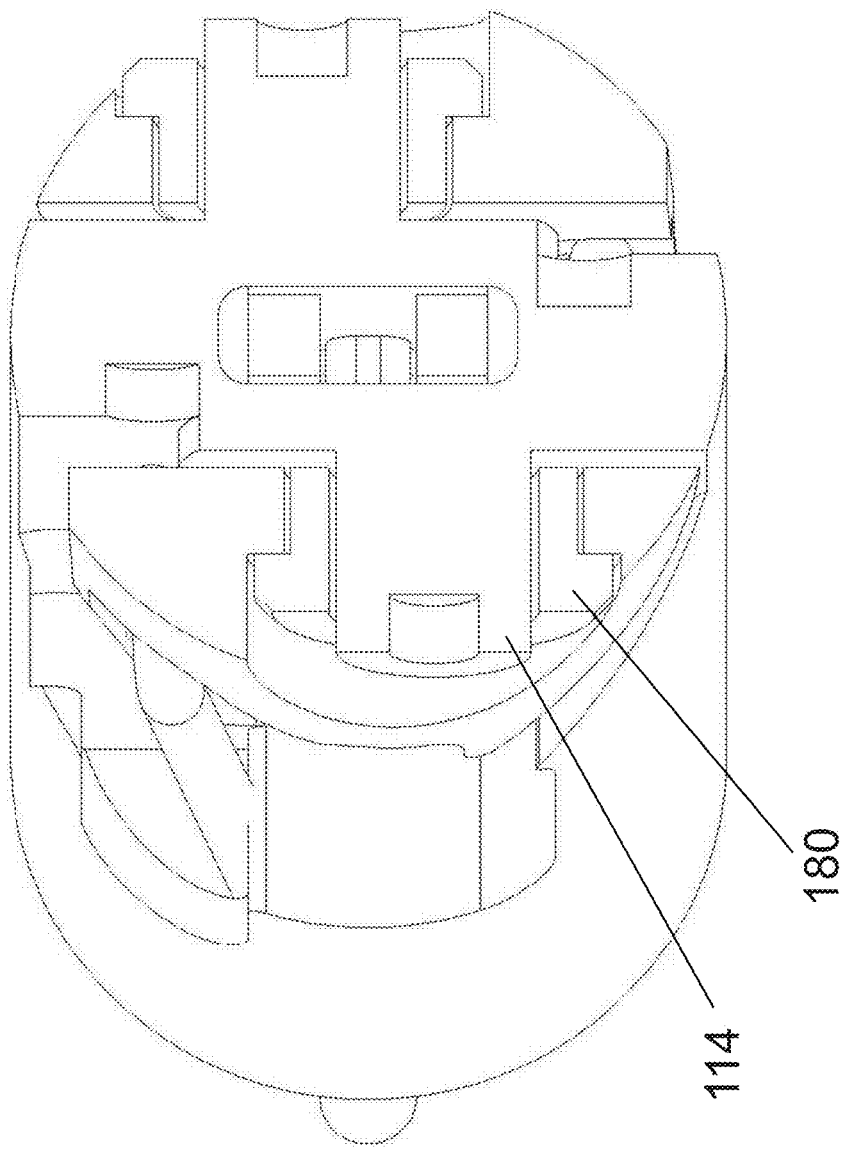

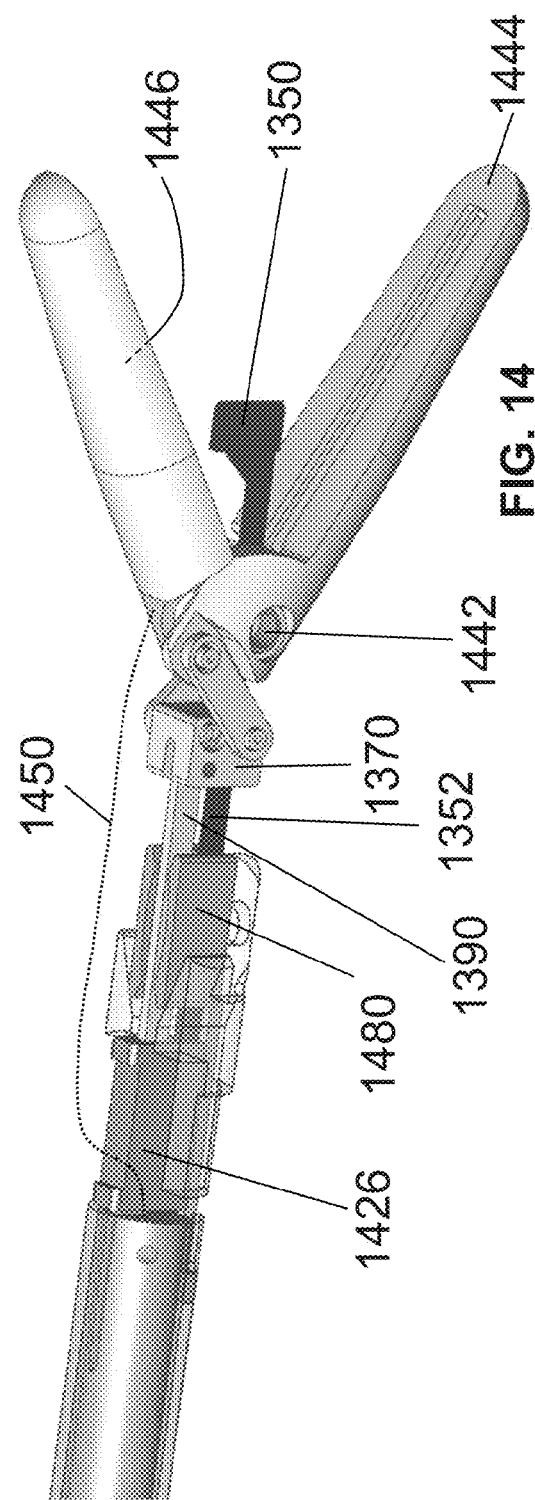
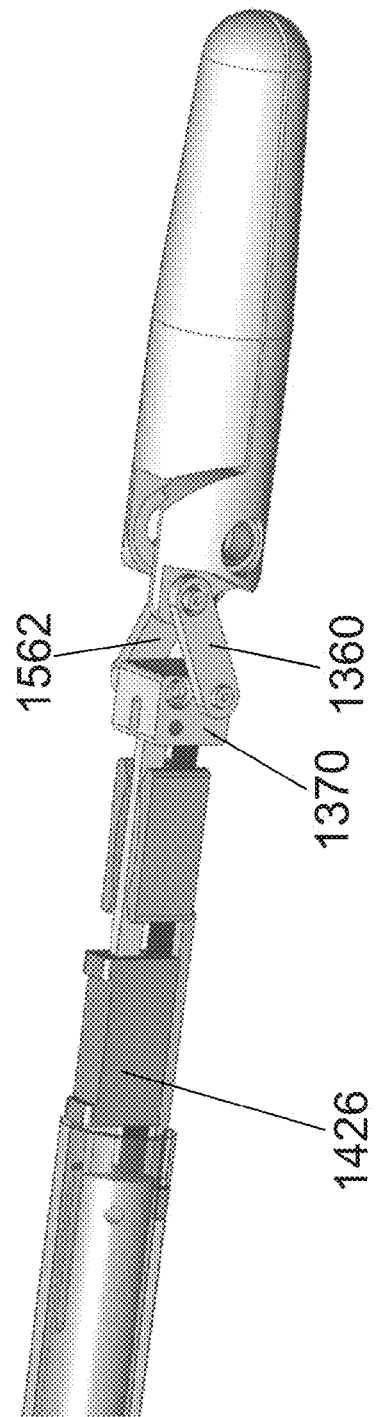
FIG. 14
FIG. 15

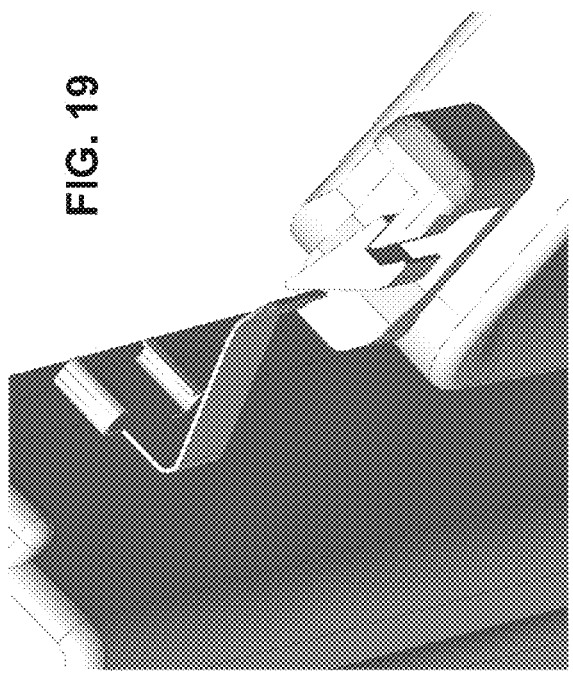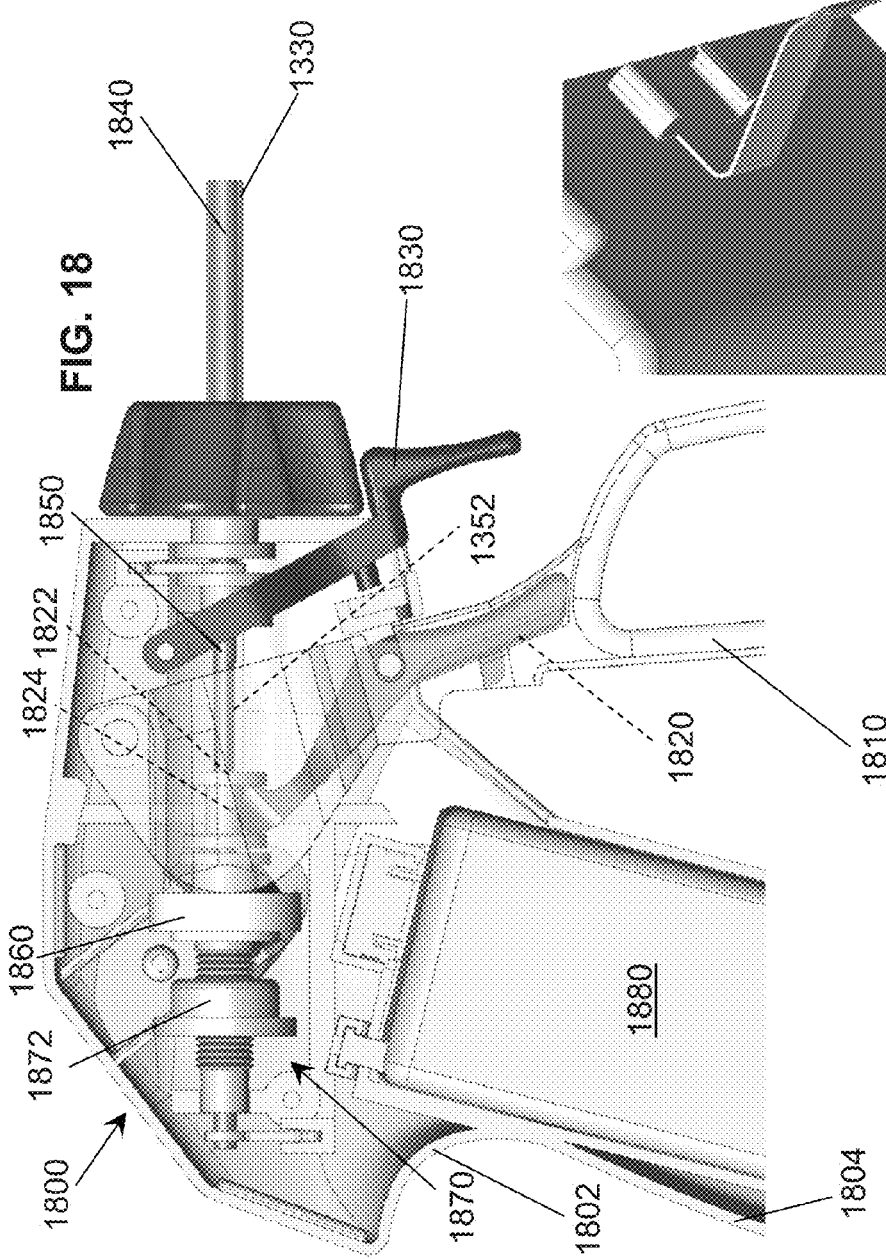

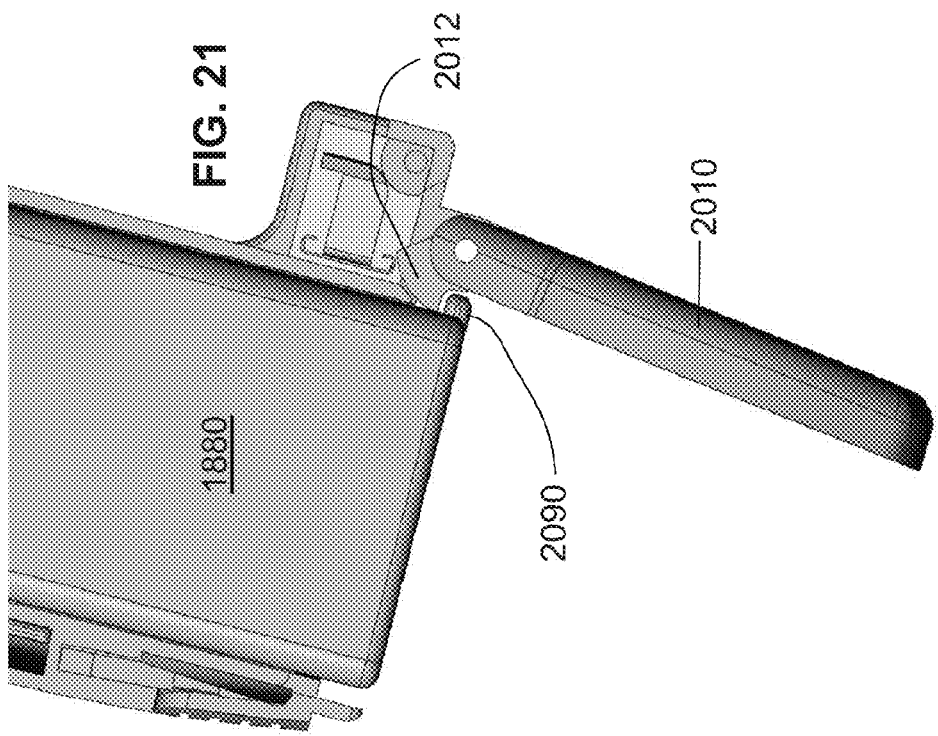
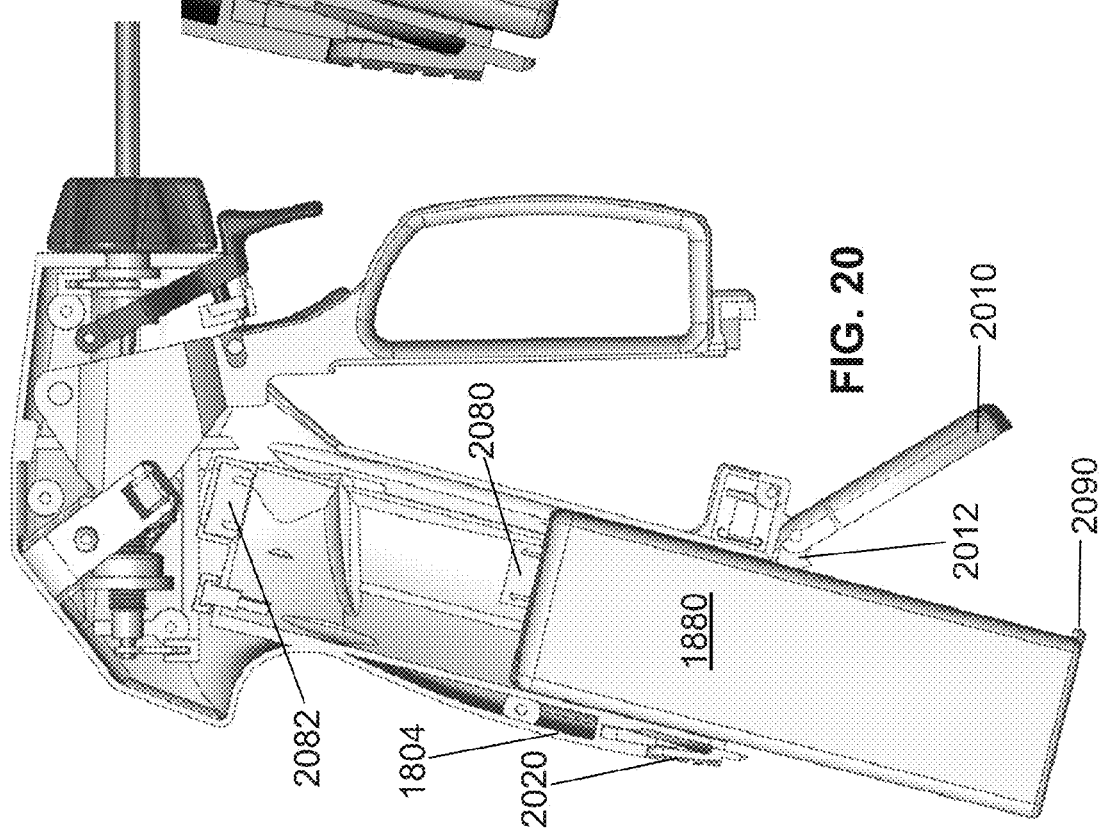

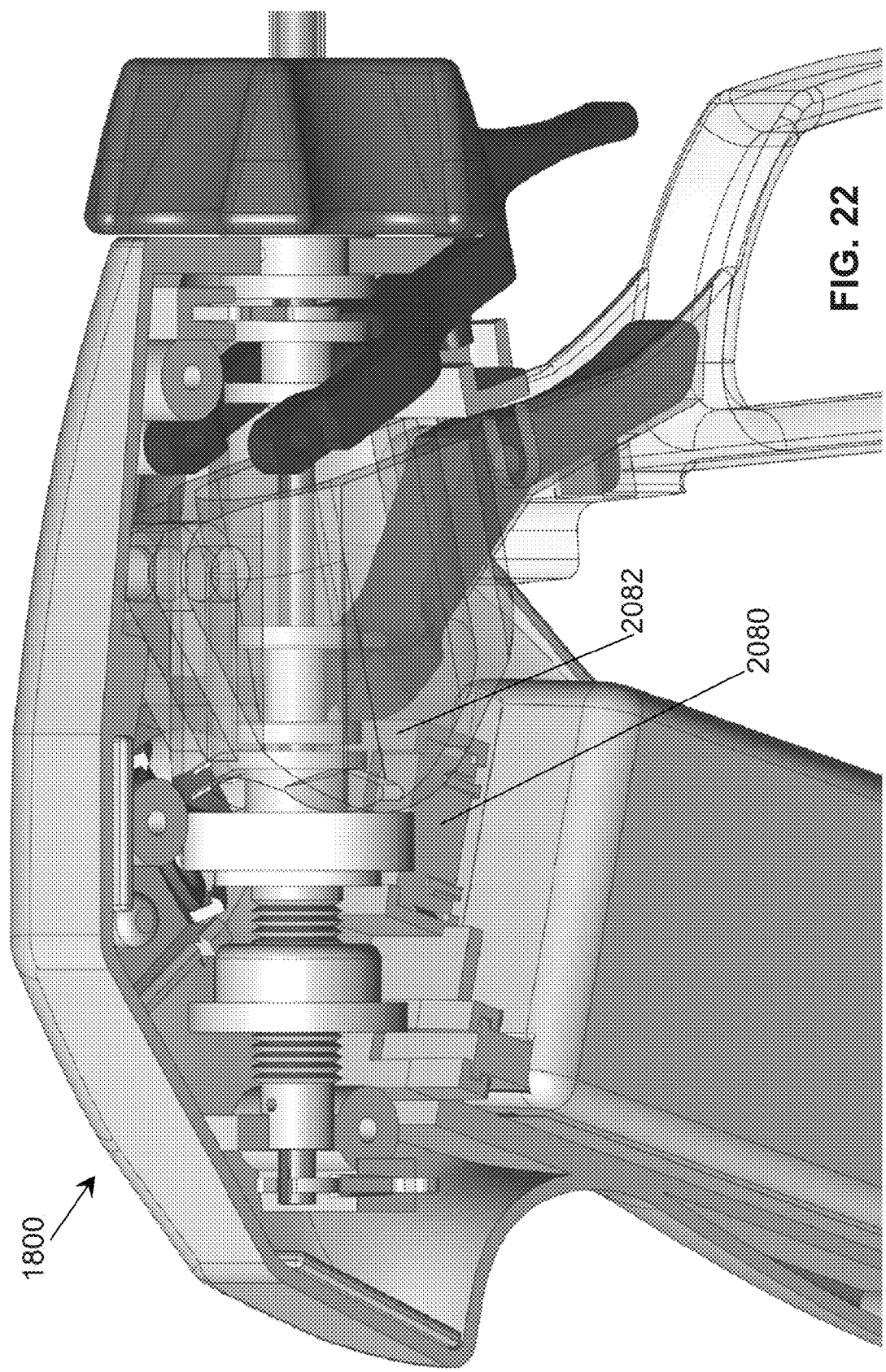

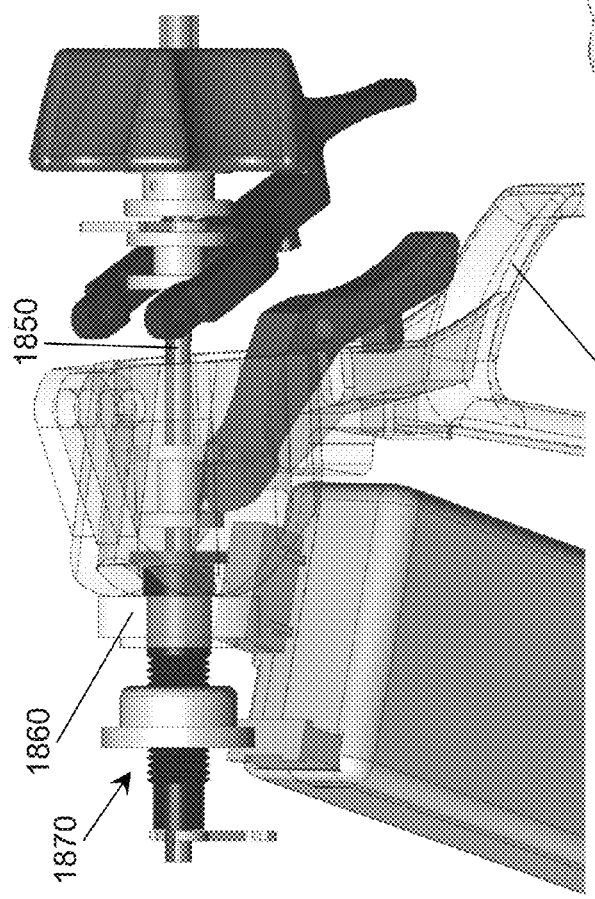
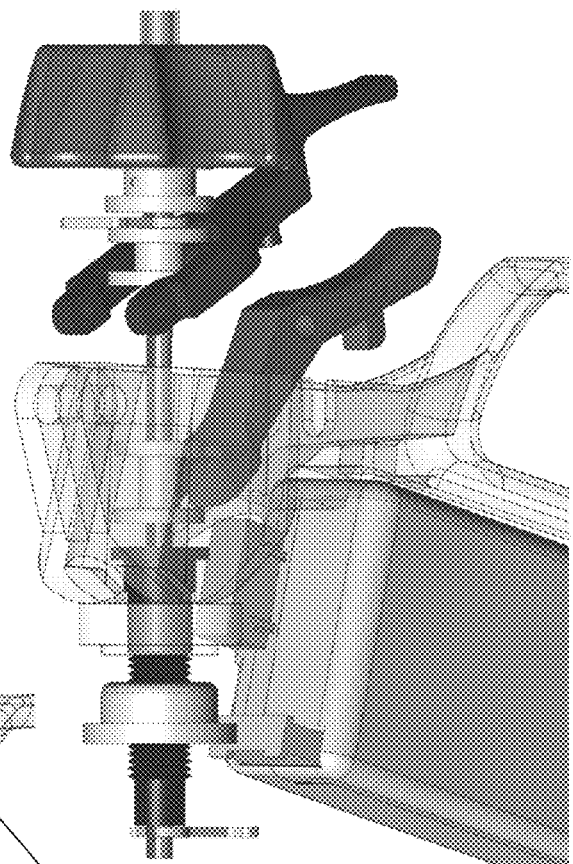

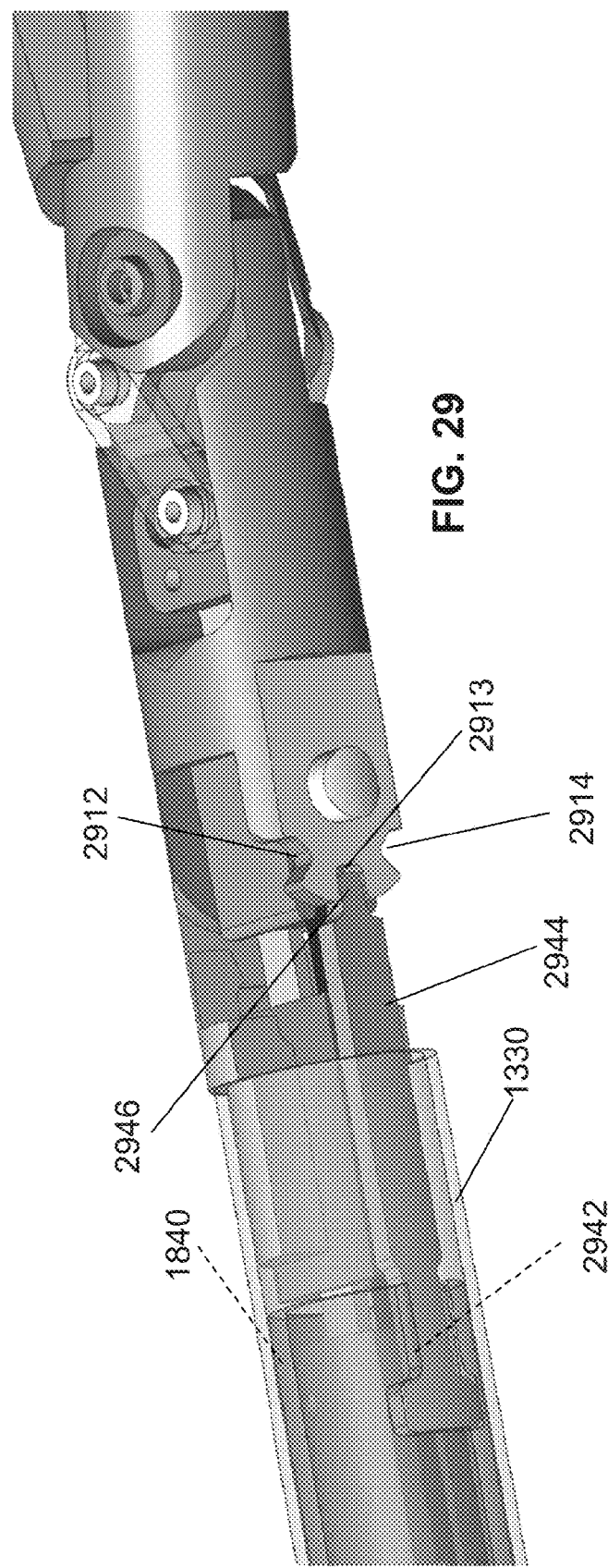

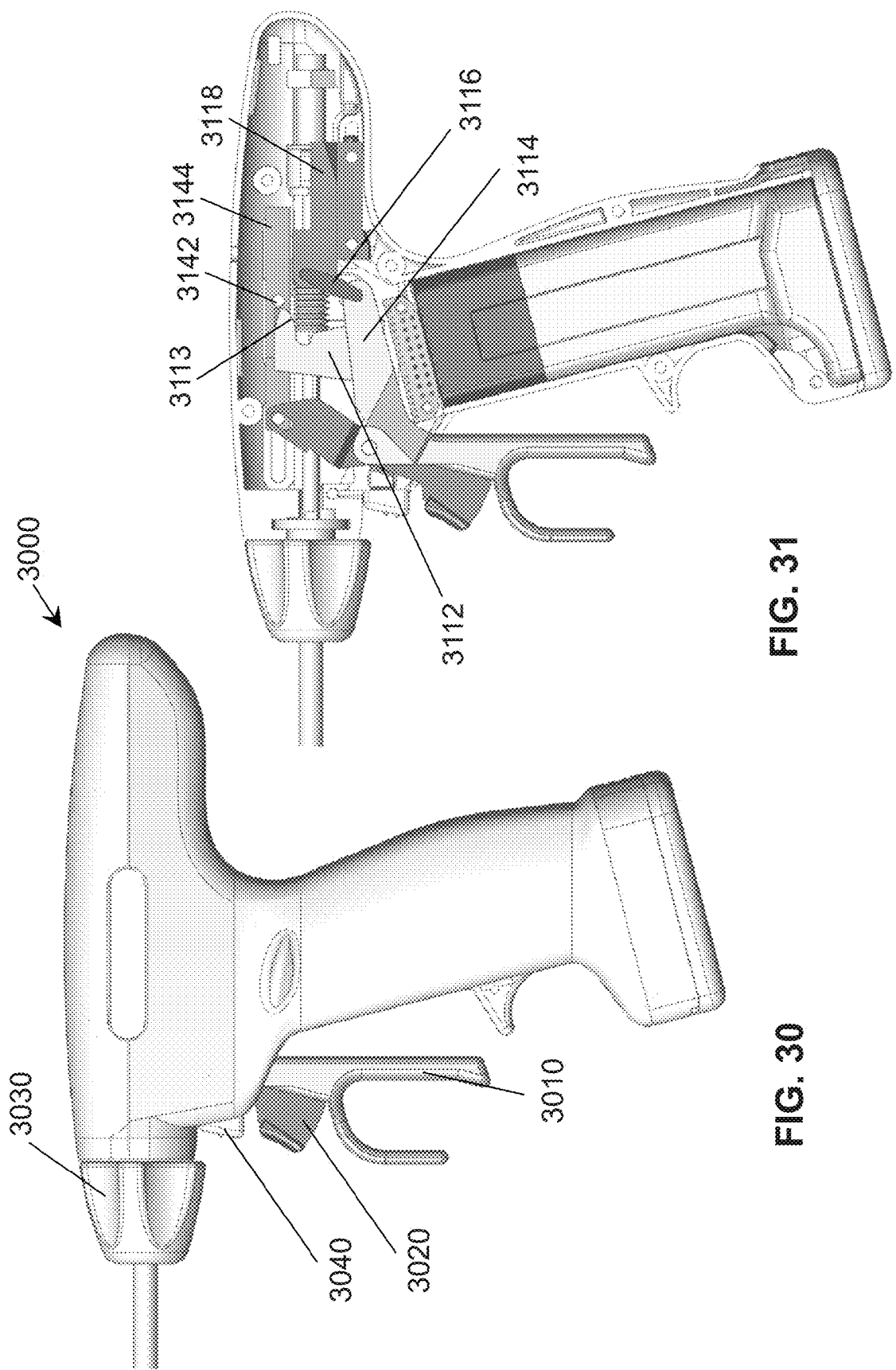

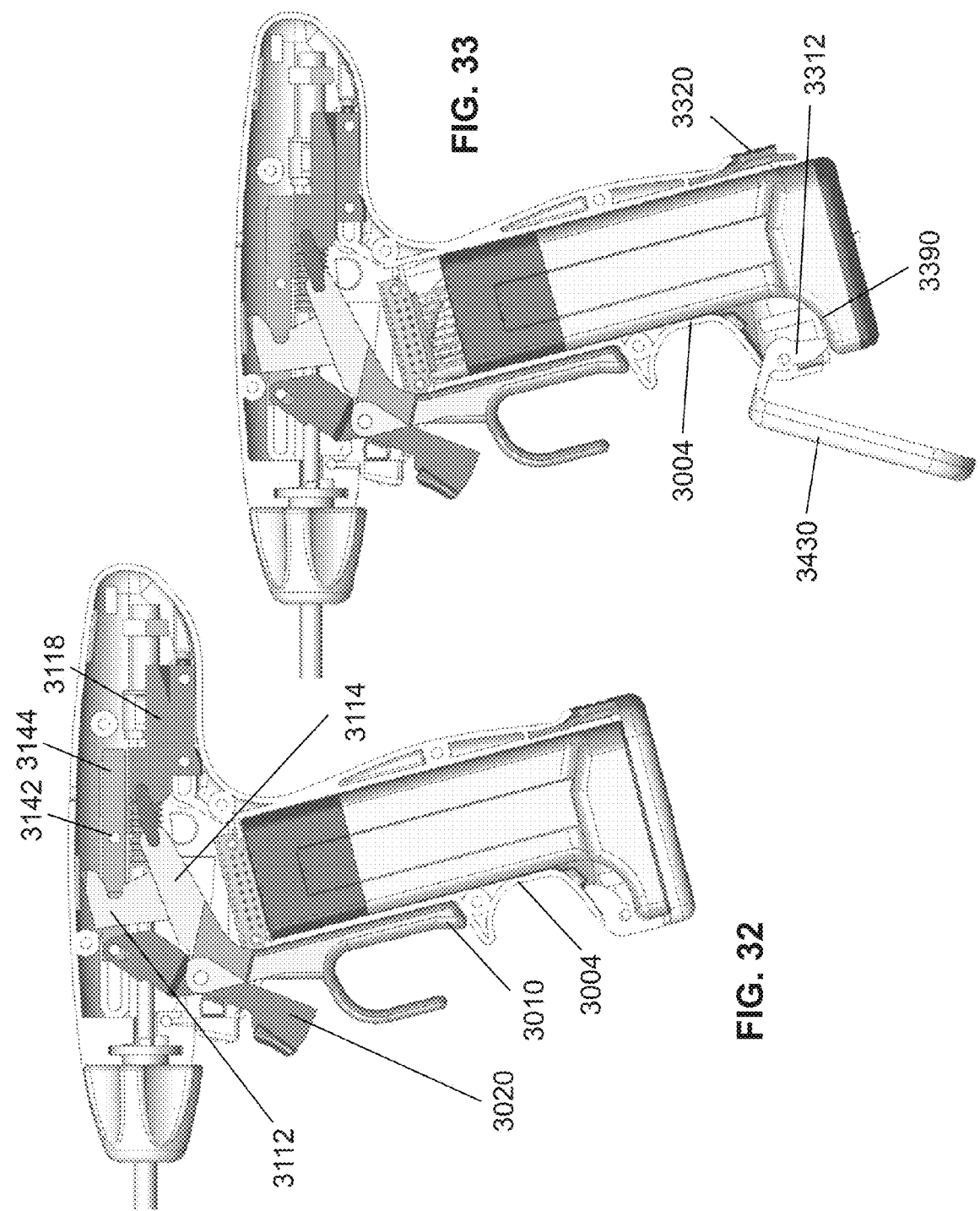

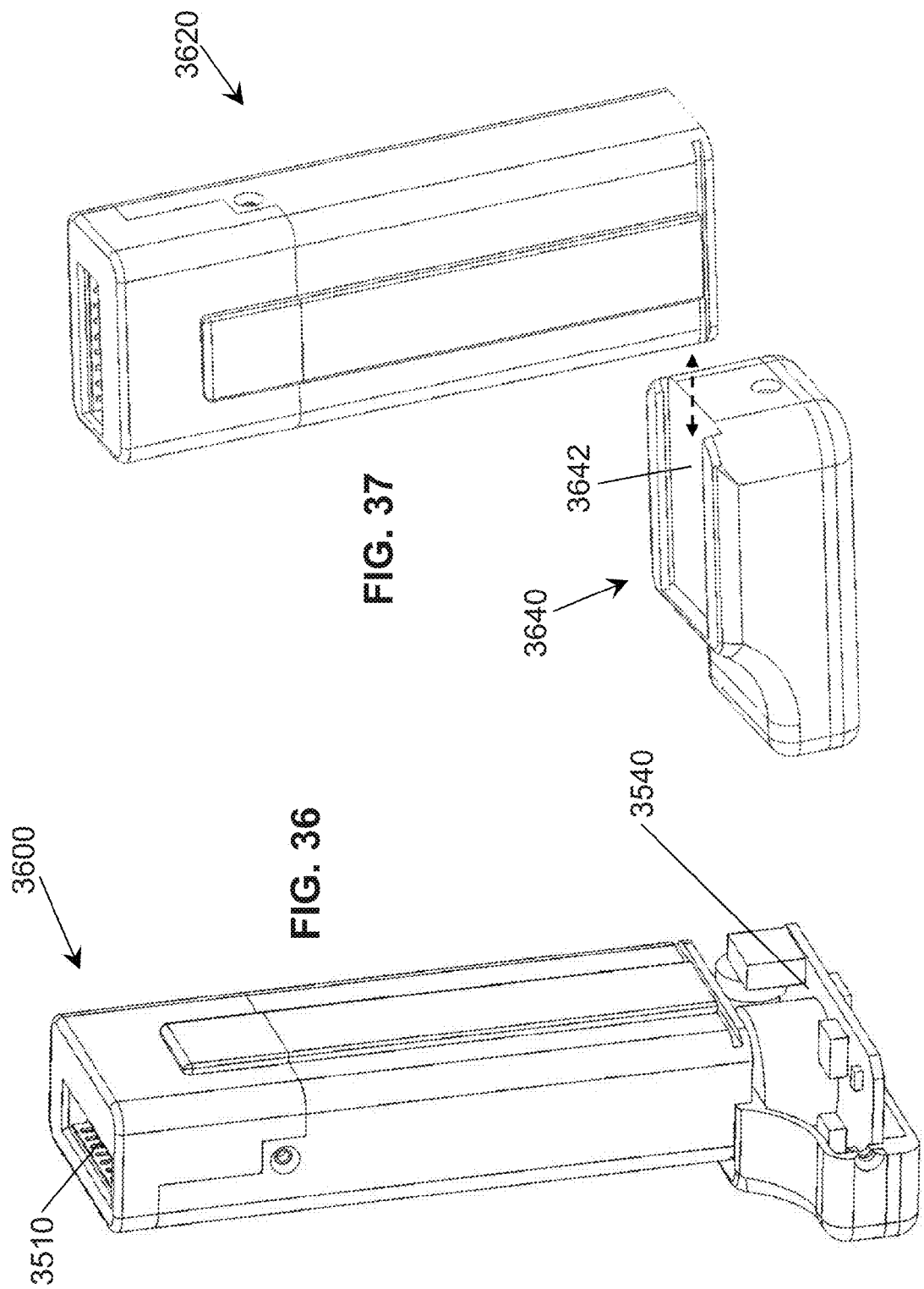

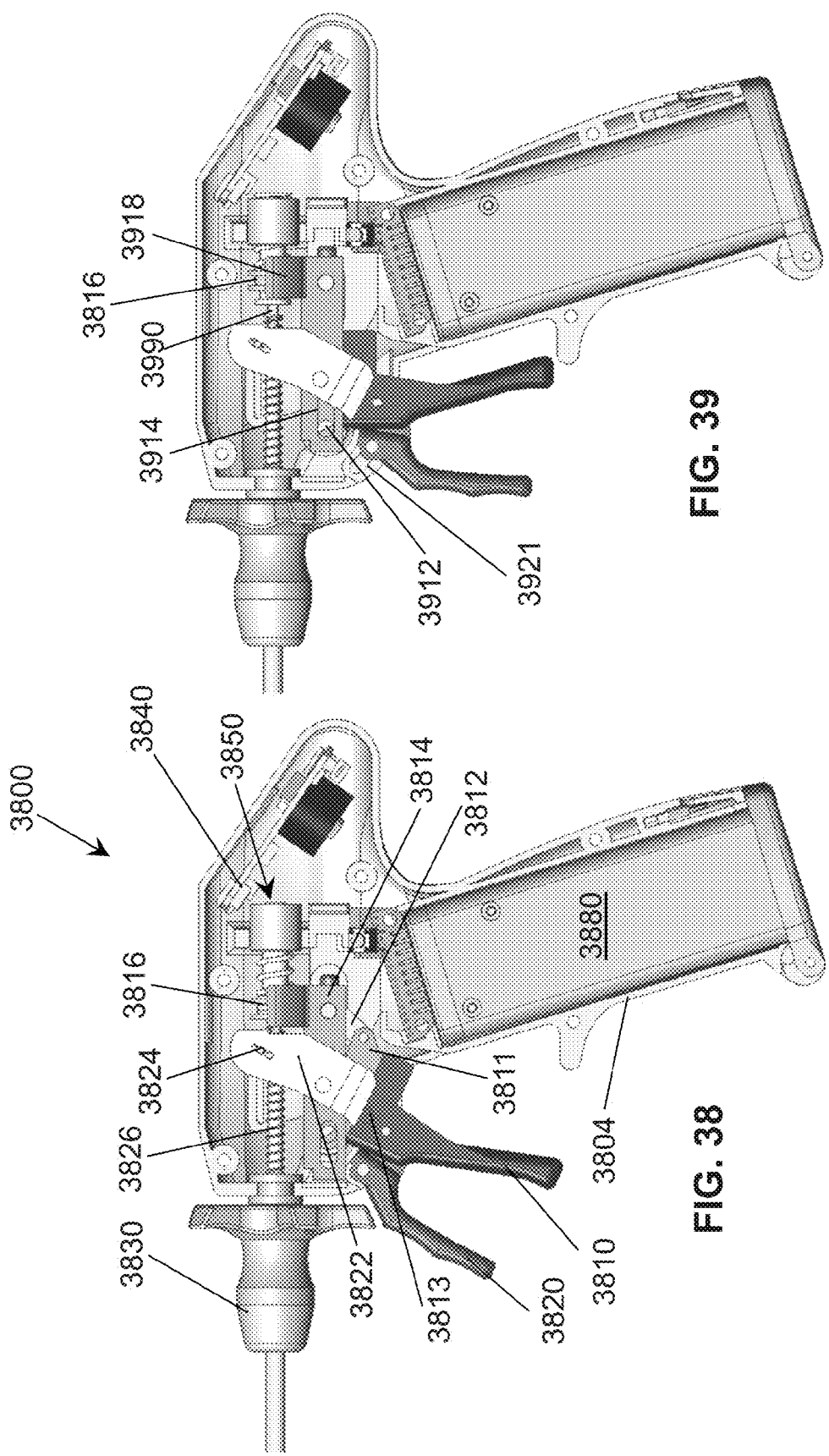

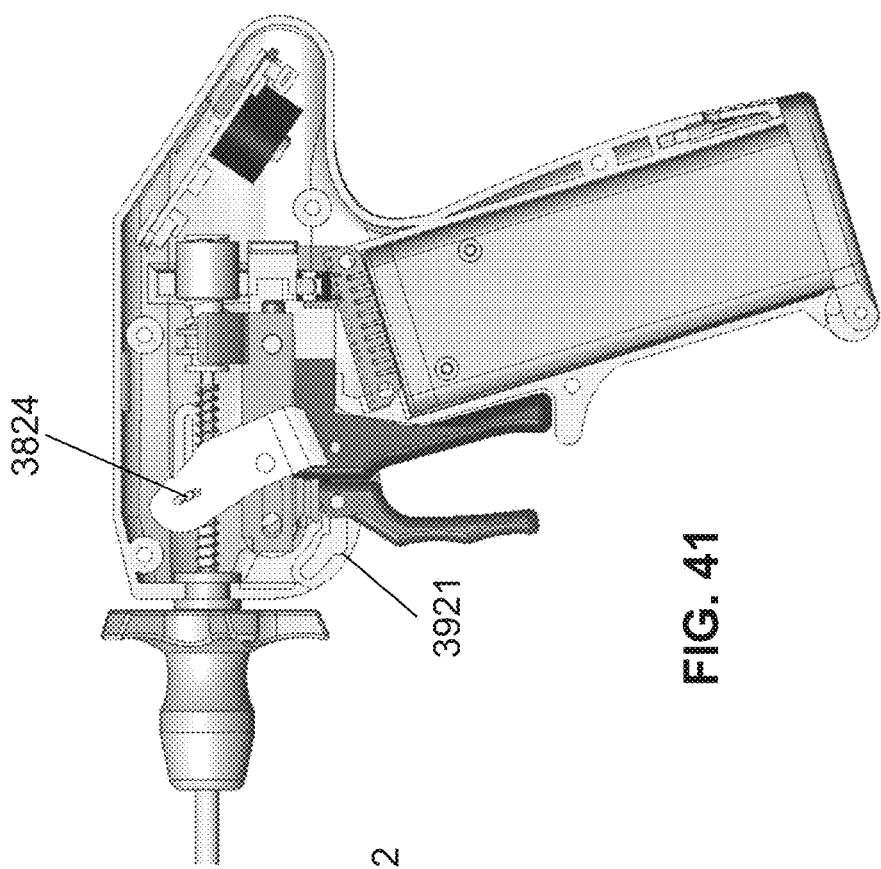
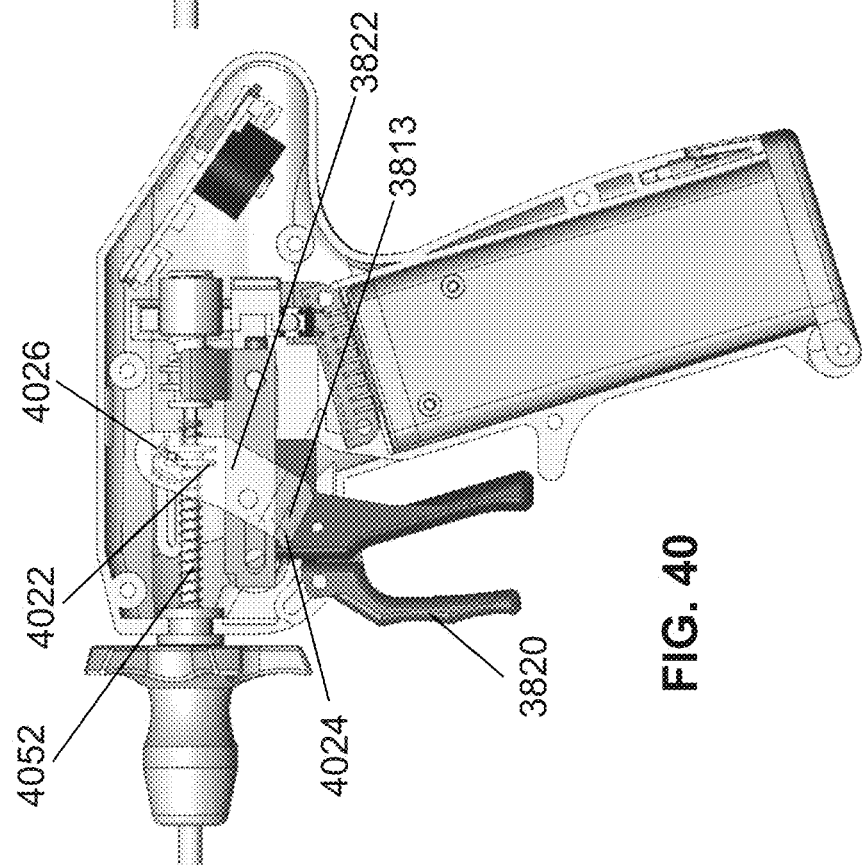

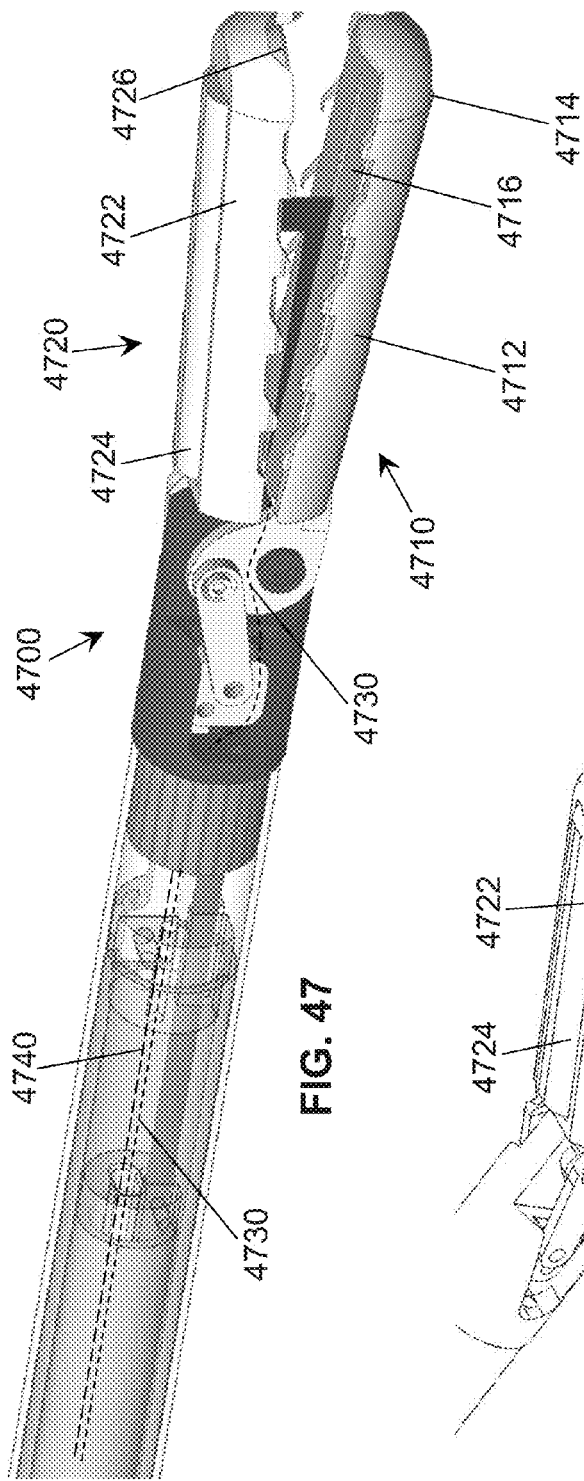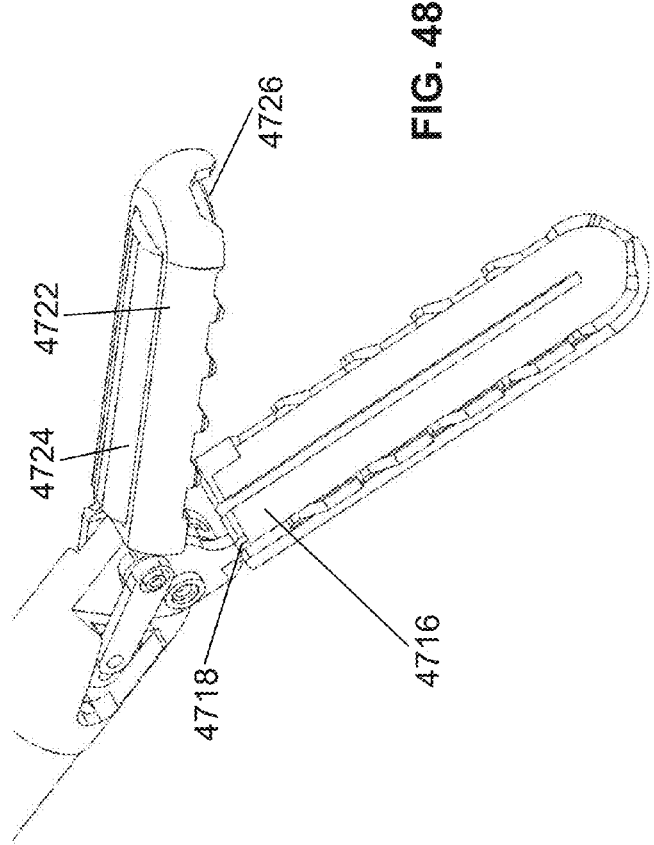

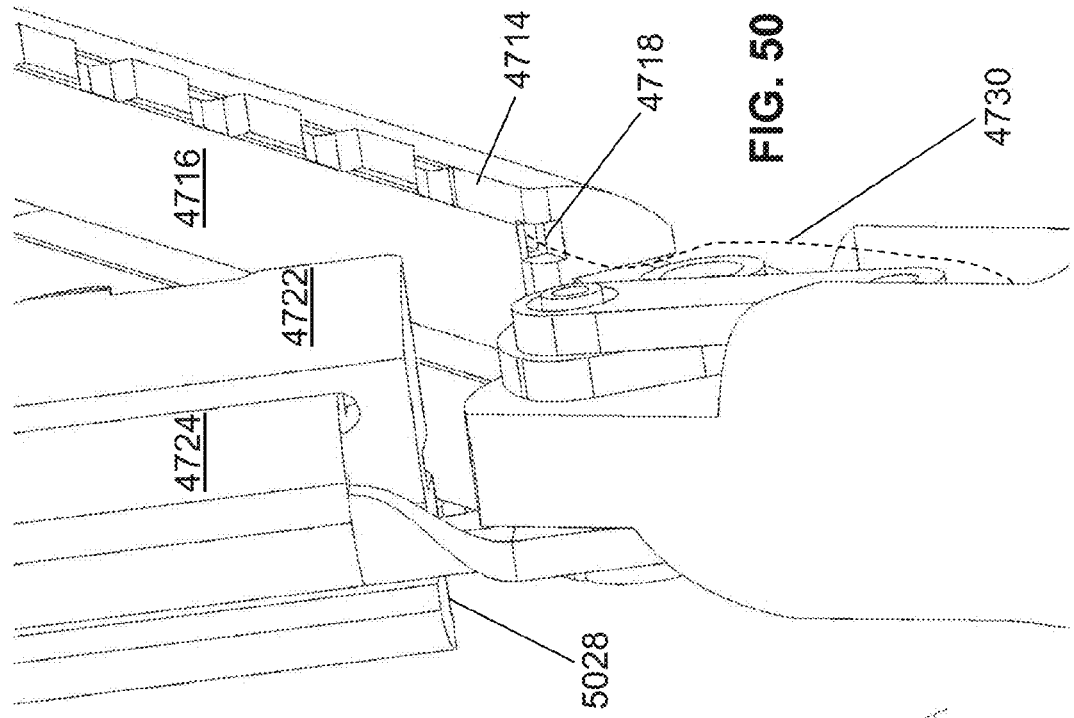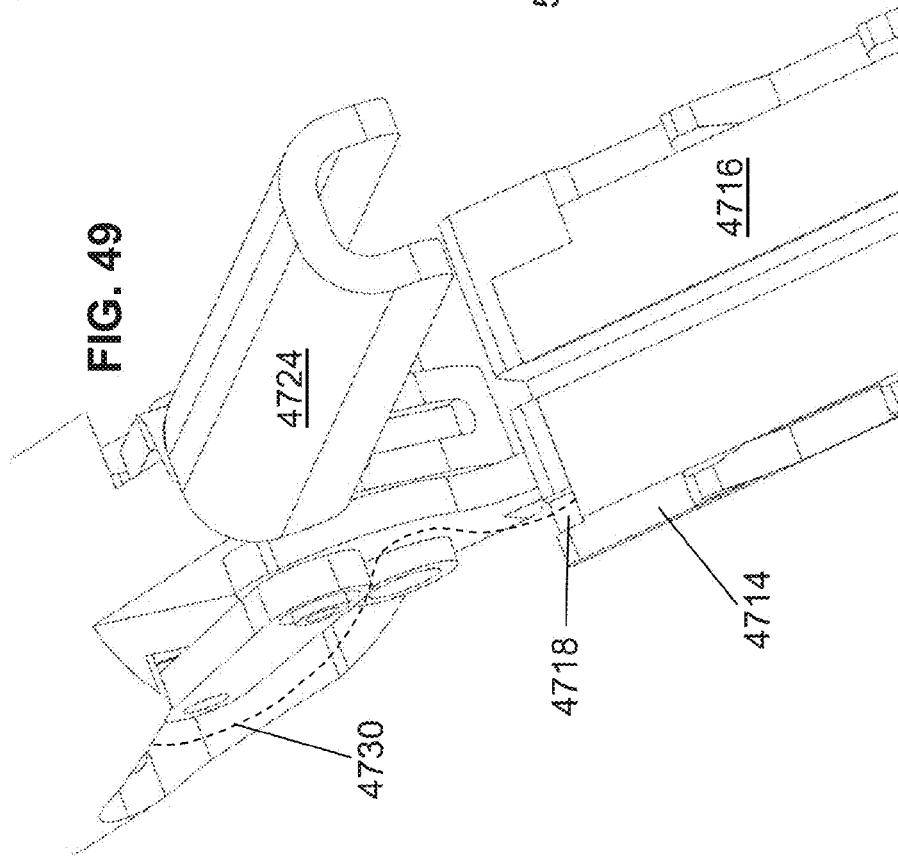

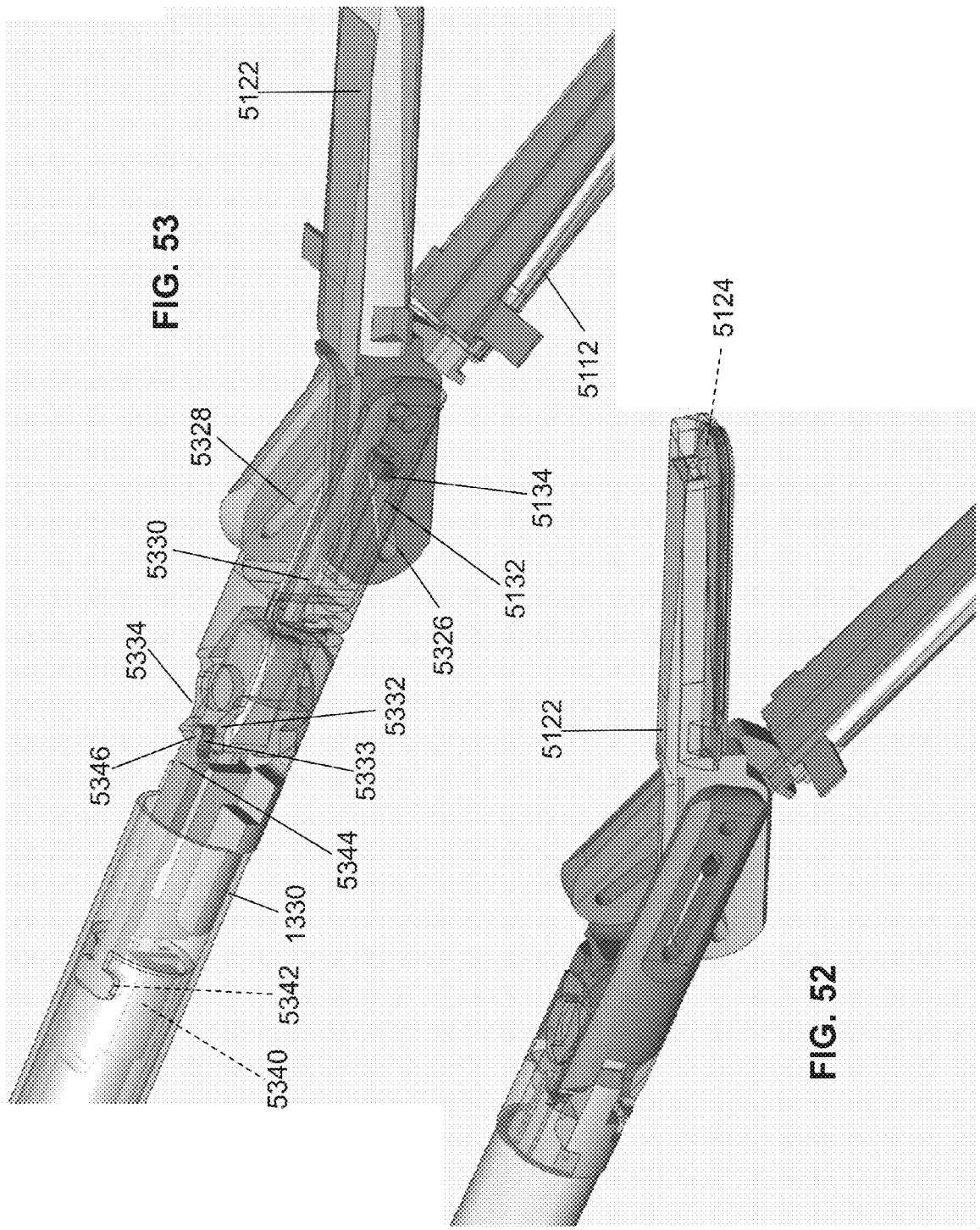

RADIO FREQUENCY GENERATOR AND METHOD FOR A CORDLESS MEDICAL CAUTERIZATION AND CUTTING DEVICE

CROSS-REFERENCE TO RELATED APPLICATIONS

This application:
claims priority to U.S. Provisional Application Ser. No. 61/792,859, filed on Mar. 15, 2013;
is a continuation-in-part of U.S. patent application Ser. No. 12/270,111, filed Nov. 13, 2008 (which claims the priority, under 35 U.S.C. §119, of U.S. Provisional Patent Application Ser. No. 60/990,784 filed Nov. 28, 2007, 61/030,748 filed Feb. 22, 2008, 61/037,788 filed Mar. 19, 2008, and 61/101,005 filed Sep. 29, 2008);
is a continuation-in-part of U.S. patent application Ser. No. 12/324,873, filed Nov. 27, 2008 (which claims the priority, under 35 U.S.C. §119, of U.S. Provisional Patent Application Ser. No. 60/990,784 filed Nov. 28, 2007, 61/030,748 filed Feb. 22, 2008, 61/037,788 filed Mar. 19, 2008, and 61/101,005 filed Sep. 29, 2008);
is a continuation-in-part of U.S. patent application Ser. No. 12/403,710, filed Mar. 13, 2009, now U.S. Pat. No. 8,491,581 (which claims the priority, under 35 U.S.C. §119, of U.S. Provisional Patent Application Ser. No. 61/037,788 filed Mar. 19, 2008, and 61/101,005 filed Sep. 29, 2008);
is a continuation-in-part of U.S. patent application Ser. No. 12/403,785, filed Mar. 13, 2009, now U.S. Pat. No. 8,377,059 (which claims the priority, under 35 U.S.C. §119, of U.S. Provisional Patent Application Ser. No. 61/037,788 filed Mar. 19, 2008, and 61/101,005 filed Sep. 29, 2008);
is a continuation-in-part of U.S. patent application Ser. No. 12/403,835, filed Mar. 13, 2009, now U.S. Pat. No. 8,328,802 (which claims the priority, under 35 U.S.C. §119, of U.S. Provisional Patent Application Ser. No. 61/037,788 filed Mar. 19, 2008, and 61/101,005 filed Sep. 29, 2008); and
is a continuation-in-part of U.S. patent application Ser. No. 13/397,484, filed Feb. 15, 2012,
the entire disclosures of which are all hereby incorporated herein by reference in their entireties.

STATEMENT REGARDING FEDERALLY SPONSORED RESEARCH OR DEVELOPMENT n/a

FIELD OF THE INVENTION

The present invention lies in the field of medical cauterization and cutting devices. The present disclosure relates to a cordless electrosurgical forceps for sealing and/or cutting tissue.

BACKGROUND OF THE INVENTION

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes, laparoscopes, and endoscopic/laparoscopic instruments for remotely accessing organs through body orifices or smaller, puncture-like incisions. As a direct result thereof, patients tend to benefit from less scarring and reduced healing time.

Laparoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make laparoscopic instruments that fit through the smaller cannulas.

Many surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an electrosurgical forceps, a surgeon can cauterize, coagulate/desiccate, and/or simply reduce or slow bleeding simply by controlling the intensity, frequency, and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different from electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to close them permanently, while larger vessels need to be sealed to assure permanent closure.

To seal larger vessels (or tissue) effectively two predominant mechanical parameters must be accurately controlled—the pressure applied to the vessel (tissue) and the gap distance between the electrodes—both of which are affected by the thickness of the sealed vessel (which term also refers to tissue when used hereinafter and vice versa). More particularly, accurate application of pressure is important to oppose the walls of the vessel, to reduce the tissue impedance to a low enough value that allows enough electrosurgical energy through the tissue, to overcome the forces of expansion during tissue heating, and to contribute to the end tissue thickness, which is an indication of a good seal. It has been determined that a typical fused vessel wall is optimum between 0.001 and 0.006 inches. Below this range, the seal may shred or tear and, above this range, the lumens may not be sealed properly or effectively.

With respect to effective sealing of smaller vessels, the pressure applied to the tissue tends to become less relevant, whereas the gap distance between the electrically conductive surfaces becomes more significant. In other words, the chances of the two electrically conductive surfaces touching during activation increases as vessels become smaller.

Many known instruments include blade members or shearing members that simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements, which are parameters that, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, the tissue may prematurely move prior to activation and sealing and/or a thicker, less reliable seal may be created.

As mentioned above, to seal larger vessels or tissue properly and effectively, a greater closure force between opposing jaw members is required. It is known that a large closure force between the jaws typically requires a large moment about the pivot for each jaw. This presents a design challenge because the jaw members are typically affixed with pins that are positioned to have small moment arms with respect to the pivot of each jaw member. A large force, coupled with a small moment arm, is undesirable because the large forces may shear the pivot pins. As a result, designers must compensate for these large closure forces by either designing instruments with metal pins and/or by designing instruments that at least partially offload these closure forces to reduce the chances of mechanical failure. As can be appreciated, if metal pivot pins are employed, the metal pins must be insulated to avoid the pin acting as an alternate current path between the jaw members, which may prove detrimental to effective sealing.

Increasing the closure forces between electrodes may have other undesirable effects, e.g., it may cause the opposing electrodes to come into close contact with one another, which may result in a short circuit, and a small closure force may cause premature movement of the tissue during compression and prior to activation. As a result thereof, providing an instrument that consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to seal the vessel uniformly, consistently, and effectively. In other words, the success of the seal would greatly depend upon the ultimate skill of the surgeon rather than the efficiency of the instrument.

The number of operations needed to uniformly, consistently, and effectively seal the vessel or tissue with such a device influences the procedure, for example, by increasingly relying on the skill of the surgeon. Typical actuation assemblies require the surgeon to perform at least four steps. With the device jaws in the normally open position, the surgeon closes the jaws by actuating a main lever. This lever can have a "ball-point pen" actuation, in that it is a push-to-lock and push-again-to-unlock (or pull-to-lock and pull-again-to-unlock) or it can just be a pull and release lever. With the main lever motion, the jaws close and impart the sealing force to the tissue or vessel. The surgeon, in a second step, presses a button to actuate the electrocautery (signal) and seal the tissue. With appropriate electronic measurements or indicators, the device informs the surgeon when sealing is complete. In a third step, the surgeon pulls a cutting trigger, which physically moves a blade distally to cut the sealed tissue. If the trigger is open-biased (for example, with a spring), it can retract the blade automatically from the tissue when released. If the blade does not stick in the tissue and does retract, the surgeon is required, in a fourth step, to unlock the main lever by pulling it, again, and letting it spring back to its original, open position through the force of a larger bias, such as another spring, or merely lets it return to the original un-actuated position. If the blade sticks in the extended position, which would prevent the jaws from opening thereafter, a safety device can exist to retract the blade and insure that the jaws can be opened after the surgical procedure is carried out.

It has been found that the pressure range for assuring a consistent and effective seal is between about 3 kg/cm$^2$ to about 16 kg/cm$^2$ and, preferably, within a working range of 7 kg/cm$^2$ to 13 kg/cm$^2$. Manufacturing an instrument that is capable of providing a closure pressure within this working range has been shown to be effective for sealing arteries, tissues, and other vascular bundles.

Various force-actuating assemblies have been developed in the past for providing the appropriate closure forces to effect vessel sealing. For example, one such actuating assembly has been developed by Valleylab Inc., a division of Tyco Healthcare LP, for use with Valleylab's vessel sealing and dividing instrument commonly sold under the registered trademark LIGASURE ATLAS®. This assembly includes a four-bar mechanical linkage, a spring, and a drive assembly that cooperate to consistently provide and maintain tissue pressures within the above working ranges. The LIGASURE ATLAS® is designed to fit through a 10 mm cannula and includes a bi-lateral jaw closure mechanism that is activated by a foot switch. A trigger assembly extends a knife distally to separate the tissue along the tissue seal. A rotating mechanism is associated with distal end of the handle to allow a surgeon to rotate the jaw members selectively to facilitate grasping tissue. Descriptions of such systems and various methods relating thereto can be found in U.S. Pat. Nos. 7,083,618, 7,101,371, and 7,150,749. The contents of all of these applications are hereby incorporated by reference herein.

All of the prior art RF vessel sealing devices require a table-top power-and-signal supply box connected to the electrodes of the jaws through a cumbersome power-and-signal supply line. The supply box takes up precious room within an operating suite. In addition, the supply box is expensive to produce, requiring the surgeon/hospital to expend significant amounts of capital to keep the unit on hand. Additionally, the supply line adds cost to produce and maintain. Importantly, the supply line commonly interferes with the surgeon's full freedom of movement during use.

It would be desirable to eliminate the need for large tabletop power supplies and controllers. In particular, it would be desirable to develop a vessel-sealing instrument that is entirely independent of the tabletop power-and-signal supply box and the supply line. It would be also desirable to miniaturize the power supply and controllers for the sealing instrument.

SUMMARY OF THE INVENTION

The device according to an exemplary embodiment of the invention is a surgical bipolar cauterization and cutting device (possibly power-assisted) that can be used, in particular, to seal and cut tissue when desired. In an embodiment of the device, measures for carrying out both the cauterization and cutting functions can be entirely contained within the device. The invention overcomes the above-noted and other deficiencies of the prior art by providing a smaller, simpler vessel-sealing instrument where power is supplied by one or more batteries. The invention entirely eliminates the need for large tabletop power supplies and controllers by miniaturizing the power supply and controllers for the sealing instrument. This miniaturization occurs in various embodiments and includes, in particular, a hand-held sealing instrument having no power or control cords; it is self-powered and all control circuitry and power supplies reside in the handle of instrument. The inventive instrument provides various configurations for locating the control and power-supply circuitry, some of which allow the circuitry to be entirely removed from the device and modularly exchanged with other circuitry. Significantly, the instrument of the invention improves upon the sealing end effector by incorporating a passively articulating end effector. Accordingly, sealing is easier to affect and becomes more reliable due to the customized placement now made possible.

The power-assisted actuation assembly of the present invention reduces the number of steps to effect the surgical procedure and, while doing so, provides additional benefits. With the jaws of the inventive device in the normally open position, the surgeon closes the jaws by actuating a main lever. Like the prior art, this lever can have the pull-to-lock and pull-again-to-unlock actuation assembly. With this first pulling motion, the jaws close and impart a first intermediate sealing force to the tissue or vessel. This force is not the final compressive force but is merely an intermediate stage that securely holds the tissue therebetween. Thereafter, in a second step, the surgeon merely presses a single button on the device and the entire procedure is carried out automatically—the procedure including, for example, a determination of Optimal Tissue Compression (OTC), an electrocautery process to cause sealing of the tissue, a cutting movement through the sealed tissue, and a release of the jaws back to the intermediate stage. The process is finalized in the third step by a second pulling motion on the main lever to open the jaws fully. It is noted that, in another exemplary embodiment of the invention, the electronic control assembly can be configured to automatically actuate the main lever and, thereby, open the jaws for release of the sealed/cut tissue, making it ready for the next sealing/cutting procedure. With the invention, therefore, the surgeon can effect a sealing and cutting procedure with only two or three steps, these steps not requiring the surgeon to provide any significant external force (such as physically moving a trigger) other than initiating the first closure of the main lever.

As set forth in the preceding paragraph, the device of the instant invention is able to automatically compress the tissue at a pre-defined force that allows beneficial healing without irretrievably harming the compressed tissue. It is known that, when tissue is being compressed (whether a single layer or multiple layers) and before cutting the tissue, it is desirable for the tissue to be at a certain compressive state (OTC) so that a desirous medical change can occur; at the same time, the tissue should not be compressed too far to cause tissue necrosis. Because there is no way to precisely control the exact kind of tissue that is being placed within the compressing jaws, it is not possible to ensure that the tissue is compressed within an Optimal Tissue Compression range, referred to as an OTC range. Therefore, ruling out of tissue necrosis is difficult or not possible for prior art electrocautery devices.

The OTC range of tissue is a compression range in which liquid is removed from the tissue (i.e., desiccates the tissue) without damaging or necrosing the tissue. As the liquid from the tissue exits the tissue however (due to compression exerted upon the tissue by the jaws), the compressive force that is being imposed upon the tissue naturally reduces—because the jaws are "locked" in position and less mass is present between the opposing jaws due to the desiccation. In some instances, this reduction can allow the imparted tissue compression to exit the OTC range. The device of the invention includes an OTC detection device that provides feedback actively to the motorized jaws compressing the tissue. This self-adjusting compression device keeps compression force on the interposed tissue within the OTC compression range even after being desiccated. More specifically, after the main lever is compressed and the automatic control switch is actuated, the device of the invention begins monitoring characteristics of either the jaws or the tissue or both to determine whether or not the tissue is compressed within the OTC range. When in that range, the device automatically starts the sealing and cutting procedure.

In one exemplary embodiment, as the jaw control lever is actuated, a force switch axially present in the jaw actuation mechanism determines if the force supplied to the tissue between the jaws is sufficient for desirable sealing and cutting. If not, then electronics of the switch prevent energy from being supplied to the end effector. Alternatively, the force switch can be used to determine if the force supplied to the tissue between the jaws is insufficient for desirable sealing and cutting. If so, then electronics of the switch prevent energy from being supplied to the end effector. Such an exemplary force switch can be found in U.S. Patent Publication No. US20070267281 and is incorporated herein by reference in its entirety. This force switch can be applied to any of the end effector embodiments described herein.

In an exemplary embodiment, the device/force switch can be configured to indicate to the surgeon (audibly, visually, or tactilely) that the tissue that is about to be sealed and cut is within a desirable OTC range. A delay can be pre-programmed in the indicator device to give the surgeon time to abort, if desired, before the surgeon applies energy for sealing and cutting. If the surgeon does not abort the procedure, electrocautery begins and the tissue is sealed. Without any further activation or movement by the surgeon, the device shifts the motorized blade distally to cut the already sealed tissue. When the blade arrives at a distal end of the cutting stroke, the device causes the blade to retract automatically from the tissue without any further actuation by the surgeon. In an exemplary embodiment, appropriately positioned limit switches can be used to activate the retraction. Powered retraction ensures that the blade does not stick in the tissue and that it retracts every time. At this point, the procedure is completed and, if appropriate motorized assemblies are included, the device can then automatically unlock the main lever, allowing it to spring back to its original open position (for example, through the force of a bias device). Thus, there is no need to include the redundant prior art safety device between the main lever and the trigger to retract the blade and insure that the jaws can be opened after the surgical procedure is carried out.

Consequently, the invention overcomes the above-noted and other deficiencies of the prior art by reducing the number of steps that the surgeon needs to undertake to effect tissue sealing and cutting. Simultaneously, the invention substantially decreases the amount of physical force needed heretofore needed to carry out such an operation. By relieving the surgeon of having to force the jaws closed and/or to extend and retract the blade, the surgeon has more physical energy to complete the overall surgical procedure, which can be many hours in length or which must be repeated for many different patients over the course of a day.

The invention overcomes the above-noted and other deficiencies of the prior art by entirely eliminating the need for large tabletop power supplies and controllers and does this by miniaturizing the power supply and controllers for the sealing instrument. This miniaturization occurs in various embodiments and includes, in particular, an entirely handheld sealing instrument having no power or control cords. Thus, all control circuitry and power supplies reside inside the handle of the instrument. In another embodiment, the power supply is self-contained but located at a distance from the instrument. In yet another embodiment, the power supply and the control electronics are located at a distance from the instrument.

Generally, endoscopic surgical control handles include a long shaft between an end effector and a handle portion manipulated by the surgeon. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. It is understood, however, that positioning of the end effector is constrained by the trocar. Thus, depending upon the nature of the operation to be carried out, it may be desirable to have adjustment in the positioning of the end effector in addition to the limited functional movements of insertion and rotation. In particular, it would be desirable to orient the end effector at an axis transverse to the longitudinal axis of the shaft of the instrument. While prior art non-articulating sealing instruments have great utility and may be successfully in many surgical procedures, they are limited to insertion and rotation movements. The present invention enhances such operation with the ability to move the end effector obliquely. In particular, the invention overcomes the above-noted and other deficiencies of the prior art by providing a passively articulating end effector to the sealing instrument.

As used in the art and as used herein, transverse movement of a medical end effector relative to an instrument shaft is referred to conventionally as "articulation." Articulated positioning permits the surgeon to more easily engage tissue in some instances. In prior art medical devices including control of articulation, the articulation movement is directed actively from the device handle. This active control can be mechanical and/or electrical. For example, some prior art devices have levers at the top of the control handle and, when pivoted left, the end effector articulates left and, when pivoted right, the end effector articulates right. Some operate with opposite movement. To effect such active articulation, it is very difficult for the operator to use only one hand. Thus, often, the operator must hold the handle with one hand and pivot the articulation lever with the other hand. As is known, the trend for laparoscopic and other similar medical devices is to make them operable with a single hand—this is because surgeons using two devices, one in each hand, often lose control of the second hand when it is necessary to remove their hand from that second device to operate an articulation lever of the first device. Loss of device control is undesirable and extends the surgical procedure if a device falls outside the view of the operating surgeon. One prior art device uses electrical measures to actively control articulation. In U.S. Pat. No. 7,213,736 to Wales et al., the disclosure argues that electrical power is supplied to an electrically actuated polymer to articulate the end effector actively in the desired direction. The device in U.S. Pat. No. 7,328,828 to Ortiz et al., requires the surgeon to control articulation by hand (see reference numeral 18). Such exemplary prior art devices can be characterized by referring to them as "active articulation" devices, in which an articulation control device is present on the handle and extends through the articulation joint to force the articulation in either articulation direction. In other words, the forces required to perform articulation are generated internally in the device.

The invention, in contrast, includes a passive articulation joint that permits the surgeon to orient the end effector along an axis transverse to the longitudinal axis of the shaft of the instrument without active articulation.

The articulation assembly of the present invention has no mechanical control device in the handle to effect direct control of articulating movement of the end effector. There is also no articulation control device present at the handle that extends through the articulation joint to force the end effector to articulate in a direction. Instead, articulation of the end effector is dependent upon pressure between a surface of the environment in which the end effector exists and an exterior surface of the end effector, for example, at a location distal of the articulation joint. A torque to pivot the inventive end effector about the articulation axis arises from forces external to the device. One force is present by the user holding the handle. The other force acts distal of the articulation joint and is imparted by the environment in which the end effector is present and against which the end effector is being held. In other words, the forces required to perform articulation are external to the device. This motion can be and is referred to herein as "passive articulation" and the "articulation joint" of the present invention operates with passive articulation—it requires a torque external to the device to articulate the end effector about the axis of the passive articulation joint.

Articulating surgical instruments generally use one or more firing bars that move longitudinally within the instrument shaft and through the articulation joint to carry out a function of the end effector. One common problem with these surgical instruments is control of the firing bar through the articulation joint. At the articulation joint, the end effector is longitudinally spaced away from the shaft so that the edges of the shaft and end effector do not collide during articulation. This gap must be filled with support material or structure to prevent the firing bar from buckling out of the joint when the single or multiple firing bars is subjected to longitudinal firing loads. What is needed is a support structure that guides and supports the single or multiple firing bars through the articulation joint and bends or curves as the end effector is articulated.

U.S. Pat. No. 5,673,840 to Schulze et al. describes a flexible articulation joint that is formed from an elastomeric or plastic material that bends at the flexible joint or "flex neck". The firing bars are supported and guided through a hollow tube within the flex neck. The flex neck is a portion of the jaw closure mechanism and moves longitudinally relative to the end effector, shaft, and firing bars when the jaws are closed on tissue. The firing bars then move longitudinally within the flex neck as the staples are fired and tissue is cut.

U.S. Pat. No. 5,797,537 to Oberlin et al. (assigned to Richard-Allan Medical Industries, Inc.) describes an articulation joint that pivots around a pin, rather than bends around a flex joint. In this instrument, firing bars are supported between a pair of spaced support plates connected at one end to the shaft and at another end to the end effector. At least one of those connections is a slidable connection. The support plates extend through the articulation joint adjacent to the flexible drive member in the plane of articulation such that the support plates bend through the gap in the plane of articulation and the flexible firing bar bends against the support when the tip is articulated in one direction from its aligned position. U.S. Pat. No. 6,330,965 to Milliman et al. from U.S. Surgical teaches the use of support plates that are fixedly attached to the shaft and slidably attached to the end effector.

Although these known support plates guide a firing bar through an articulation joint, it is believed that performance may be enhanced. For instance, it is often desirable for the firing bar to be accelerated rapidly during firing to ensure sufficient momentum for severing tissue effectively. Rigidly attached support plates may tend to dislodge in response, allowing the firing bar to blow out from the articulation joint. As a further example, it is desirable for the instrument to operate in the same manner whether articulated or not. Increased friction when articulated would be inconvenient and distracting to the clinician if required to exert a varying amount of firing force. Consequently, the present invention provides an improved articulation mechanism for the surgical instrument that enhances support to the firing bar through the articulation joint.

In one aspect of the invention, the surgical instrument has a handle portion that releases a lock to allow articulation of the end effector and to permit cutting while articulated. The articulating-release and cutting mechanisms are transferred through a shaft to the articulation mechanism. The articulation mechanism responds to forces that the user imparts to the end effector and allows articulation of the end effector out of line with the longitudinal axis of the shaft. The cutting mechanism responds to the cutting motion and is coupled for movement through the articulation mechanism and the end effector. A cutter support device allows the cutting mechanism to be supported and keep it in place as articulation occurs.

The movable distal end effector can be center-biased in an advantageous embodiment. This means that, after the distal end is passively moved into a new articulation position (by engaging the end effector with a feature of the environment, such as surrounding tissue), the next actuation of the articulation lock release will permit the end effector to return to a center position under the urging of a center-biasing device (if the end effector is free from contact with the environment). In one embodiment, the biasing device is at least one biasing spring and can be, for example, two biasing springs imparting a biasing force in opposing and, therefore, centering directions. Alternatively, the center-biasing device can be a set of spring-loaded plungers disposed on either side of the end effector at the clevis to urge the end effector independently towards the center position. These embodiments are explained in detail in U.S. Pat. Nos. 7,404,508 and 7,491,080 to Smith et al., which are hereby incorporated by reference herein in their entireties.

In one exemplary embodiment, the trigger that permits/inhibits passive movement is in a normally locked position. This lock is released by pulling in the trigger. Once the distal end effector is in a desired position, the user releases the trigger, thereby locking the distal end effector in its new position.

The device according to an exemplary embodiment of the invention is a surgical bipolar cauterization and cutting device that can be used, in particular, to seal and cut tissue when desired. In one embodiment of the device, measures for carrying out both the cauterization and cutting functions can be entirely contained within the device.

Actuation of the device is accomplished using at least one servo in an exemplary embodiment.

The device may also be actuated by multiple electric motors, by hydraulics or pneumatics, or by the transmission of energy through a flexible drive shaft in any way such that the actuation assembly can be contained primarily or entirely in the distal portion of the device.

The work accomplished by any of these measures can be converted into desirable motions through any single or combination of screw drive, gear drive, wedge, toggle, cam, belt, pulley, cable, bearing, or the like push rod. In particular, a screw drive is used to transmit the work of the electric motor into linear motion. In one embodiment, the motor for the screw drive resides in the handle. A flexible rotating cable is connected from the motor to a threaded shaft. Thus, when the motor turns in either direction, the rotation of the flexible cable is transmitted to the threaded drive shaft and, because the stapling actuator and cutting slide is disposed on the drive shaft, both functions are carried out by distal movement of the slide. In a second embodiment, the motor resides entirely in the end effector and has a shaft connected to the slide drive shaft, either directly or through transmission gears. In such a case, all that is needed in the handle is the on/off and drive shaft direction actuators, the former for turning the motor on and off and the latter determining which direction the motor will spin.

In one aspect of the invention, the instrument actuates an end effector with a longitudinally translating firing mechanism that is supported advantageously through an articulation mechanism by either flanking support plates or a rigid support channel. In the former embodiment, to better respond to firing loads on the firing mechanism, one or more ends of each support plate are resiliently or springedly engaged to one side of the articulation mechanism, and thus are better able to avoid buckling of the firing mechanism. For example, the pair of support plates flanks the firing mechanism across the articulation mechanism, each support plate including an end springedly engaged to a frame recess formed in the articulation mechanism to assist in preventing buckling of the firing mechanism within or out of the articulation mechanism. In the channel embodiment, the channel floats in the articulation mechanism and has surfaces that support either side of the firing mechanism as articulation occurs in either direction and, thus, avoid buckling of the firing mechanism. The channel has a floor and two sides. The support channel rests freely in a cavity inside the articulation mechanism. Ends of the channel are curved to match curves of the cavity. The support channel has various internal surfaces to contact and support the firing mechanism as it is bent within the articulation mechanism and, thereby, assists in preventing buckling of the firing mechanism within or out of the articulation mechanism.

With the foregoing and other objects in view, there is provided, in accordance with the invention, a circuit for generating a radio-frequency signal for a surgical device. The circuit has a voltage regulator that supplies direct current (DC) voltage, a first MOSFET, a second MOSFET, and a MOSFET driver. The MOSFET driver receives the DC voltage supplied from the voltage regulator and has a local oscillator. The local oscillator switches the first MOSFET and the second MOSFET on and off at a frequency generated by the local oscillator. The circuit further includes a transformer connected to the first and second MOSFETs, having a center tap and a main voltage applied at the center tap, and providing an alternating current (AC) output.

In accordance with a further feature of the invention, there is provided an interlock terminal that controls power to the circuit through the voltage regulator.

In accordance with an added feature of the invention, the voltage regulator supplies DC voltage to the local oscillator and to the MOSFET driver.

In accordance with an additional feature of the invention, the MOSFET driver is self-oscillating.

In accordance with yet another feature of the invention, the MOSFET driver is a dual MOSFET driver.

In accordance with yet a further feature of the invention, the MOSFET driver establishes the frequency of the local oscillator.

In accordance with yet an added feature of the invention, there is provided a capacitor and a resistor connected to the local oscillator and having respective capacitance and resistance values that set the frequency of the local oscillator.

In accordance with yet an additional feature of the invention, the MOSFET driver has a resistance for time delay port connected to the resistor.

In accordance with again another feature of the invention, the MOSFET driver has an oscillator timing capacitor port connected to the capacitor.

In accordance with again a further feature of the invention, the frequency is set to approximately 300 kHz.

In accordance with again an added feature of the invention, the transformer has a first input grounded by the first MOSFET.

In accordance with again an additional feature of the invention, the transformer has a second input grounded by the second MOSFET.

In accordance with still another feature of the invention, the output of the transformer is a product of a turns ratio of the transformer and the voltage supplied by the voltage regulator.

In accordance with still a further feature of the invention, the transformer has a secondary side and the output of the transformer is at the secondary side and comprises an output voltage.

In accordance with still an added feature of the invention, the output voltage on the secondary side of the transformer has a frequency of approximately 300 kHz.

With the objects of the invention in view, there is also provided a circuit for generating a radio-frequency signal for a surgical device. The circuit has a voltage regulator supplying direct current (DC) voltage, a first MOSFET, a second MOSFET, and a self-oscillating dual MOSFET driver. The self-oscillating dual MOSFET driver receives the DC voltage supplied from the voltage regulator and has a local oscillator. The local oscillator switches the first MOSFET and the second MOSFET on and off at a frequency generated by the local oscillator. The circuit further includes a transformer having a center tap and a main voltage applied at the center tap, a first input grounded by the first MOSFET, and a second input grounded by the second MOSFET, and providing an alternating current (AC) output.

In accordance with a further feature of the invention, the MOSFET driver establishes the frequency of the local oscillator.

In accordance with an added feature of the invention, there is provided a capacitor and a resistor connected to the local oscillator and having respective capacitance and resistance values that set the frequency of the local oscillator.

In accordance with an additional feature of the invention, the MOSFET driver has a resistance for time delay port connected to the resistor and the MOSFET driver has an oscillator timing capacitor port connected to the capacitor.

In accordance with a concomitant feature of the invention, the transformer has a secondary side and the output of the transformer is at the secondary side and comprises an output voltage having a frequency of approximately 300 kHz.

The invention overcomes the above-noted and other deficiencies of the prior art by improving wear resistance and lubricity of the working end of the sealing instrument by utilizing hard-coat anodizing at selected locations on the working area of the instrument.

In still a further aspect of the invention, a surgical instrument has a handle portion that includes a jaw closing device, a blade-firing device, and an articulation unlocking device, each operable through a shaft at the end of which is the end effector. The end effector includes, in one exemplary embodiment, a jaw fixedly coupled to the shaft and an anvil pivotally coupled to the shaft and controlled by the jaw closing device. Of course, both jaws can be pivotable, whether co-dependently or independently. The blade-firing device is connected from the handle to the end effector through the shaft and through the articulation mechanism or joint (when such joint is present). The blade-firing device carries out the cutting when actuated. The articulation mechanism allows movement of the end effector with respect to the shaft. The articulation mechanism is distally coupled to the shaft and permits passive articulation (also referred to as natural articulation) of the end effector after the articulation unlocking device is actuated (i.e., unlocked). With such actuation, the end effector is free to articulate in response to a force(s) that acts upon the end effector. In other words, when the articulation lock is unlocked, pressure of the environment against the end effector will cause articulation of the end effector with respect to the shaft.

With the foregoing and other objects in view, there is provided, in accordance with the invention, a surgical device including a radio-frequency-signal-generation assembly including a radio-frequency-signal-generation circuit operable to generate a radio-frequency signal at an output and adapted to couple to a switch-mode power supply; and a surgical handle including an end effector having at least one jaw with at least one electrical contact, the end effector including at least one signal input that electrically connects to the output to provide the radio-frequency signal at the at least one electrical contact.

The radio-frequency generation circuit is small, inexpensive, and the simplest radio-frequency unit for vessel sealing. The radio-frequency circuit uses a novel push/pull outlet with a center tap. In contrast, most prior art devices are regulated by pulse width modulation on the output. Also disclosed is a novel method created for the switch mode power supply that allows the device to provide better tissue sealing.

Endoscopic and laparoscopic surgery requires the physician to be able to use both hands independently. Prior art devices, with their active articulation controls, require both hands for using the single device. The prior art devices, therefore, make such surgeries extremely difficult or not possible. A significant advantage of the present invention is that the articulation of the end effector is passive and lockable without a need for a second hand. In other words, the end effector can be unlocked, subsequently moved into a desired articulated position, and, then, caused be retained in the new position—all of this being done with a one-handed operation.

A further advantage of the present invention is that the axial movement of the end effector is dynamically rotatable about the longitudinal axis of the device at any time by the user. A rotation device axially fixedly but rotationally freely connects the handle to the distal components including the shaft, the articulation mechanism, and the end effector. Rotation of the distal components occurs by applying a rotational force to the rotation device about the longitudinal axis of the shaft in the desired direction. In an embodiment where passive articulation is present, pulling the rotation device in a direction away from the end effector unlocks the end effector to permit passive articulation (in an exemplary embodiment, the rotation device is bell-shaped). This rotating movement, in combination with the off-axis articulation movement of the end effector creates a compound angle at the distal end of the device to aid in accurate positioning of the end effector.

To support the blade-firing mechanism, a pair of support plates can flank the firing mechanism across the articulation mechanism, each support plate including an end springedly engaged to a frame recess formed in the articulation mechanism, or a rigid channel can surround the firing mechanism across the articulation mechanism. Alternatively, a U-shaped or H-shaped rigid channel can be provided for such support (and for electrically isolating the cutting and jaw-moving controls from one another). Thereby, an improved sealing and cutting instrument may incorporate a blade-firing device that withstands high firing loads yet does not introduce significantly increased firing forces when articulated.

The device may be manufactured in different lengths and/or be manufactured in diameters appropriate for either laparoscopic or endoscopic use, or both. A replaceable end-effector cartridge can be used. In addition, the actuation device can be constructed to attach to a distal end of a flexible endoscope.

The Optimal Tissue Compression (OTC) range of tissue is a compression range in which liquid is removed from the tissue (i.e., desiccates the tissue) without damaging or necrosing the tissue. In one exemplary embodiment, as the jaw control lever is actuated, a force switch axially present in the jaw actuation mechanism determines if the force supplied to the tissue between the jaws is sufficient for desirable sealing and cutting. If not, then electronics of the switch prevent energy from being supplied to the end effector. Alternatively, the force switch can be used to determine if the force supplied to the tissue between the jaws is insufficient for desirable sealing and cutting. If so, then electronics of the switch prevent energy from being supplied to the end effector. Such a force switch can be found in U.S. Patent Publication No. US20070267281 and is incorporated herein by reference in its entirety. In an exemplary embodiment, the force switch can be configured to indicate to the surgeon (audibly, visually, or tactilely) that the tissue is within a desirable OTC range. A delay can be pre-programmed in the indicator device to give the surgeon time to abort, if desired, before the surgeon applies energy for sealing and cutting. This force switch can be applied to any of the end effector embodiments described herein.

Other features that are considered as characteristic for the invention are set forth in the appended claims.

Although the invention is illustrated and described herein as embodied in a cordless medical cauterization and cutting device, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the device between the end effector and the control handle. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

Advantages of embodiments of the present invention will be apparent from the following detailed description of the preferred embodiments thereof, which description should be considered in conjunction with the accompanying drawings in which:

FIG. 3 is a fragmentary, side elevational view of the end effector of FIG. 1 with the lower jaw removed and with the upper jaw is an open orientation past the max-open position;

FIG. 4 is a fragmentary, longitudinally cross-sectional view of the end effector of FIG. 1 in a first longitudinally cross-sectional plane parallel to a plane of the blade;

FIG. 5 is a fragmentary, longitudinally cross-sectional view of the end effector of FIG. 1 in a third longitudinally cross-sectional plane coplanar with the blade plane;

FIG. 6 is a colored, fragmentary, partially transparent, side elevational view of the end effector of FIG. 1 with the upper jaw removed and the lower jaw in a closed orientation;

FIG. 7 is a colored, fragmentary, partially transparent, side elevational view of the end effector of FIG. 1 with the upper jaw removed, the lower jaw in a partially open orientation, and the blade in a retracted position;

FIG. 8 is a colored, fragmentary, partially transparent, side elevational view of the end effector of FIG. 7 with the blade in an extended position;

FIG. 9 is a colored, fragmentary, partially transparent, side elevational view of the end effector of FIG. 7 with the lower jaw in an extended open position to restrict movement of the blade body and the blade control device;

FIG. 10 is a fragmentary, transverse cross-sectional view of the end effector of FIG. 1 in a second transverse cross-sectional plane transverse to the linear extent of the blade and through the blade body and the pivot bosses of the jaws;

FIG. 14 is a fragmentary perspective and partially transparent view of the passive articulating electrocautery sealing and cutting surgical device of FIG. 13 with a distal joint portion removed, an upper proximal joint portion removed, a transparent lower proximal joint portion, and a transparent outer shaft portion;

FIG. 15 is a fragmentary perspective and partially transparent view of the passive articulating electrocautery sealing and cutting surgical device of FIG. 14 with the jaws in a closed orientation and the lower proximal joint portion removed;

FIG. 18 is a fragmentary elevational and partially transparent side view of a passive articulating electrocautery sealing and cutting surgical device of with a right side cover of the handle removed and a battery assembly inserted within the handle;

FIG. 19 is a perspective view of the underside of the passive articulating electrocautery sealing and cutting surgical device of FIG. 18 showing a switch disposed on an underside of the first trigger;

FIG. 20 is a fragmentary elevational side view of the passive articulating electrocautery sealing and cutting surgical device of FIG. 18 with the battery assembly partially inserted within the handle;

FIG. 21 is an enlarged fragmentary elevational side view of the battery compartment of the handle of FIG. 18 with the right side cover of the handle removed and a door in an intermediate position partially ejecting the battery assembly from the battery compartment;

FIG. 22 is a fragmentary perspective and partially transparent view of the passive articulating electrocautery sealing and cutting surgical device of FIG. 18;

FIG. 23 is a fragmentary perspective and partially transparent view of the passive articulating electrocautery sealing and cutting surgical device of FIG. 18 with both halves of the handle removed and the first trigger partially depressed;

FIG. 24 is a fragmentary perspective and partially transparent view of the passive articulating electrocautery sealing and cutting surgical device of FIG. 23 with the first trigger fully depressed;

FIG. 29 is a fragmentary enlarged perspective and partially transparent view of the passive articulating electrocautery sealing and cutting surgical device of FIGS. 13 to 17 with the jaws open;

FIG. 30 is an elevational side view of an electrocautery sealing and cutting surgical device according to the present invention;

FIG. 31 is a fragmentary elevational side view of the electrocautery sealing and cutting surgical device of FIG. 30 with a left side cover of the handle removed and a battery assembly inserted within the handle;

FIG. 32 is a fragmentary elevational side view of the electrocautery sealing and cutting surgical device of FIG. 30 with a left side cover of the handle removed and a first trigger depressed;

FIG. 33 is a fragmentary elevational side view of the electrocautery sealing and cutting surgical device of FIG. 30 with a left side cover of the handle removed and the battery door opened and automatically ejecting the battery assembly from the battery chamber;

FIG. 36 is a perspective and partially cut-away view of an alternative embodiment of the inventive battery assembly according to the present invention;

FIG. 37 is an exploded perspective view of the battery assembly of FIG. 36;

FIG. 38 is a fragmentary elevational side view of an alternative embodiment of the passive articulating electrocautery sealing and cutting surgical device according to the present invention with a left side cover of the handle removed and a battery inserted within the handle;

FIG. 39 is a fragmentary elevational side view of the passive articulating electrocautery sealing and cutting surgical device of FIG. 38 with first and second triggers depressed to a first position;

FIG. 40 is a fragmentary elevational side view of the passive articulating electrocautery sealing and cutting surgical device of FIG. 38 with the first trigger depressed to the first position and the second trigger depressed to a second position;

FIG. 41 is a fragmentary elevational side view of the passive articulating electrocautery sealing and cutting surgical device of FIG. 40 with the first trigger depressed to the first position and the second trigger depressed to a third position;

FIG. 47 is a fragmentary enlarged perspective and partially transparent view of another exemplary embodiment of an electrocautery sealing and cutting surgical end effector according to the present invention with serrated jaws in a max-open position;

FIG. 48 is a fragmentary perspective view of the electrocautery sealing and cutting surgical end effector of FIG. 47 with the jaws open past the max-open position;

FIG. 49 is a fragmentary enlarged perspective view from a distal end of the electrocautery sealing and cutting surgical end effector of FIG. 48 with an outer portion of the upper jaw removed;

FIG. 50 is a fragmentary enlarged perspective view from a proximal side of the electrocautery sealing and cutting surgical end effector of FIG. 47;

FIG. 52 is a fragmentary enlarged perspective and partially transparent view from a distal side of the passive articulating electrocautery sealing and cutting surgical end effector of FIG. 51;

FIG. 53 is a fragmentary enlarged perspective and partially transparent view from a distal side of the passive articulating electrocautery sealing and cutting surgical end effector of FIG. 52 with an upper part of a two-part proximal articulation joint portion removed;

DETAILED DESCRIPTION OF THE INVENTION

Figure 1:
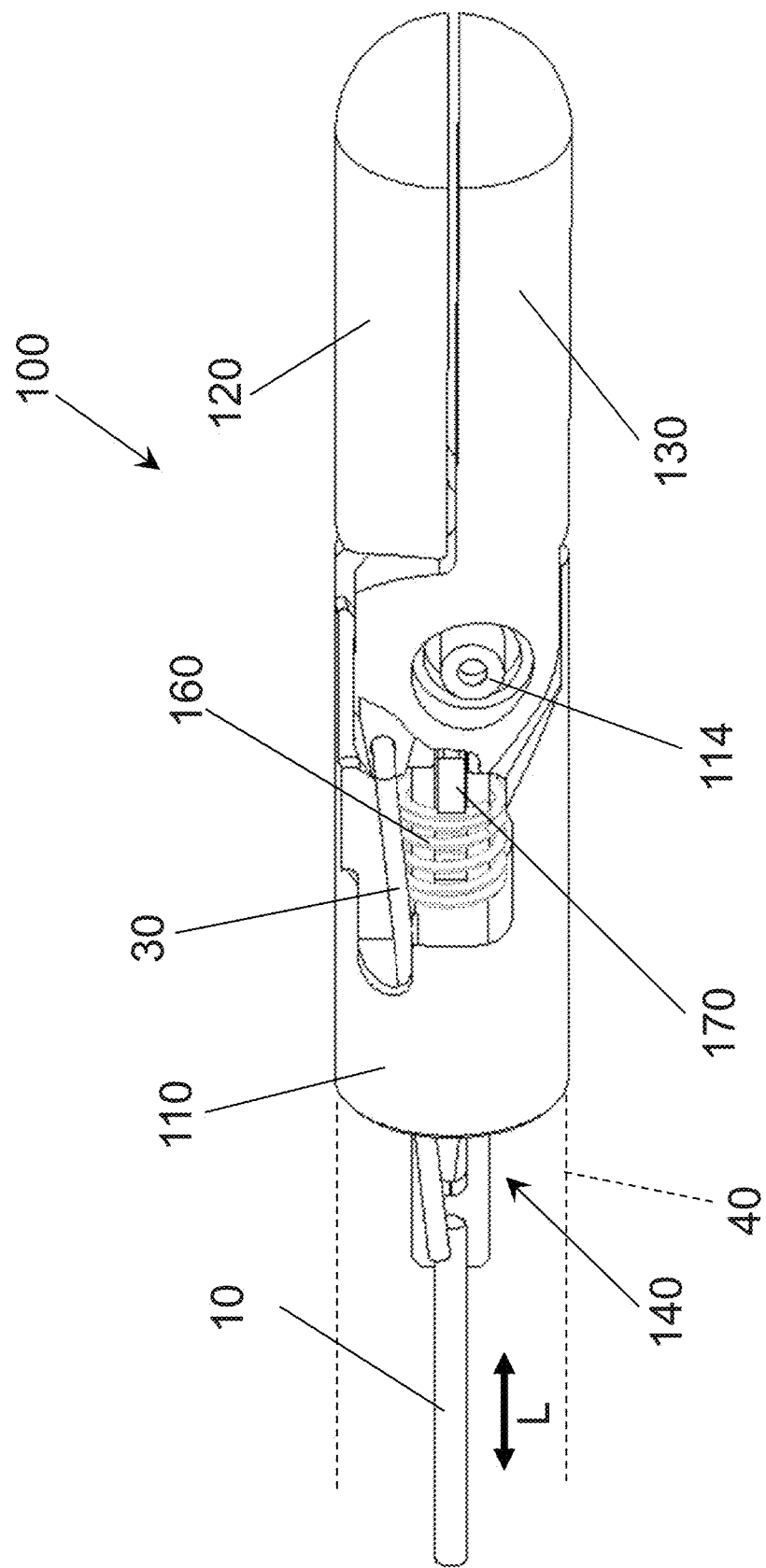
FIG. 1 is a fragmentary, perspective and partially cut away view of the end effector of the present invention with the shaft removed and with the jaws in a closed orientation.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Referring now to the figures of the drawings in detail and first, particularly to FIG. 1 thereof, there is shown an exemplary embodiment of a bipolar cautery and cutting end effector 100 of the present invention. In many of the figures of the drawings, the proximal portion of the device (e.g., the handle) is not shown or is illustrated only diagrammatically, for example, the exemplary embodiment shown in FIGS. 1 to 11. In the figures, a cutting actuation wire 10 extends a distance proximally to a non-illustrated cutting actuation assembly that is capable of moving the cutting actuation wire 10 in the longitudinal direction (L). Similarly, a pair of jaw actuation wires 20, 30 extends proximally towards the non-illustrated jaw actuation assembly, which is capable of moving the jaw actuation wires 20, 30 in the longitudinal direction (L). The wires 20, 30 can extend all of the way back to the actuation assembly and can be individually actuatable or separately actuatable. Alternatively, the wires 20, 30 can meet at an intermediate point and, thereafter, a single actuator can extend proximally back to the actuation assembly.

The bipolar cautery and cutting end effector 100 of this embodiment of the present invention is shown only to its proximal end in these figures. Between this proximal end and the non-illustrated actuation assembly is an outer sheath 40 (illustrated only diagrammatically by dashed lines) having an outer shape that is substantially similar or identical to an outer shape of the clevis 110 or that transitions from a first shape smoothly to the outer shape of the clevis 110. For example, in a flexible embodiment of the outer sheath 40, the outer sheath 40 can be comprised of a flexible inner coil (e.g., of stainless steel) with an outer coating of a polymer that is, for example, heat-shrunken upon the coil. In a non-flexible exemplary embodiment of the outer sheath 40, the sheath 40 can be a one-piece tube-shaped cannula of stainless steel. Other similar embodiments for flexible and non-flexible end effector extensions are also envisioned.

Figure 2:
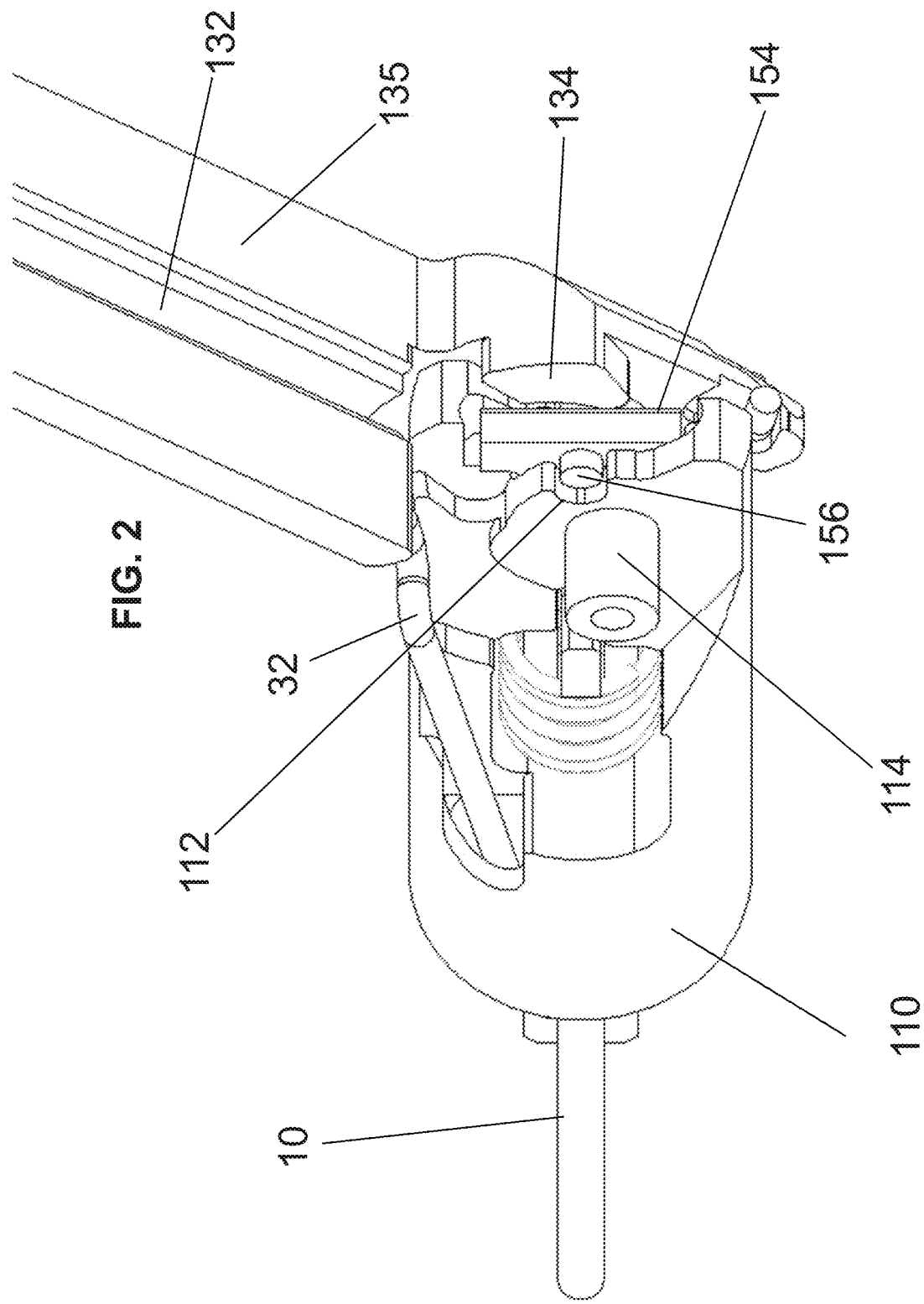
FIG. 2 is a fragmentary, perspective view of the end effector of FIG. 1 with one jaw in an open orientation past a max-open position and with the lower jaw removed.

The end effector 100 has a pair of opposing jaws 120, 130, each pivotally connected to the clevis 110. FIG. 1 shows the jaws in the clevis-aligned, closed position and FIG. 2 shows one jaw in a clevis-aligned, extended open position. As will be describe below in more detail, this particular open position is referred to as "extended" because it is exaggerated from a desired fully-open position of the jaws 120, 130.

The cutting actuation wire 10 is connected at its distal end to a cutting assembly 140, which is best seen in FIG. 5 and includes a blade body 150, a blade lock bias device 160, and a blade control device 170. More specifically, the distal end of the cutting actuation wire 10 is connected to the proximal end of the blade body 150. An intermediate portion of the blade body 150 defines a control slot 152, which will be described in further detail below. The blade body 150 has a distal end at which is a cutting blade 154. Here, the blade 154 is perpendicular to the longitudinal axis of the blade body 150 but, in other exemplary embodiments, can be at an angle thereto. Extending from the blade body 150 is at least one blade boss 156. See, e.g., FIG. 2. In one exemplary embodiment, there are two opposing and identical blade bosses 156, one on either side of the blade body 150.

The blade 154 is positioned within the jaws 120, 130 to cut tissue therebetween and, in particular, before, during, and/or after the cautery jaws 120, 130 have sealed the tissue on either side of the cut. To insure that the blade 154 does not extend distally until the user desires such extension, a non-illustrated bias device in the actuation handle imparts a proximally directed bias at all times. When the user desires to extend the blade 154 distally, the user actuates the blade extension control and overcomes the proximally directed bias of this actuation handle bias device. The proximally directed bias is a force sufficient to keep the blade body 150 in the proximal-most position within the end effector 100 but not enough to cause damage to the blade assembly or to the end effector 100.

The cutting assembly 140 includes its own bias device 160 for locking the blade body 150 dependent upon a current position of the jaws 120, 130, and which is explained along with the blade control device 170. As shown in FIG. 3, the blade control device 170 resides within the control slot 152 of the blade body 150. The blade control device 170 has a proximal surface 172 oriented orthogonal to the longitudinal axis of the blade body 150, and, in this exemplary embodiment, also orthogonal to the longitudinal axis of the end effector 100. This orientation of the proximal surface 172 provides a bearing surface for the distal end 162 of the blade lock bias device 160, which, in this exemplary embodiment, is a compression spring. The blade control device 170 also has a distal end with a distal bearing surface 174 having a shape corresponding with the interior shape of the distal end of the control slot 152. Here, the two shapes are curved, in particular, semi-circular. These shapes can take any form, even angular or pointed, and can even be different. All that is needed in this cooperative engagement is for the distal end of the control slot 152 to be able to impart a force on the distal bearing surface 174 when the blade body 150 is moved proximally to, thereby, correspondingly move the blade control device 170 along with the blade body 150. The blade lock bias device 160 is positioned and pre-tensioned to force the blade control device 170 towards and/or into the distal end of the control slot 152.

Because the size of the end effector 100 is about 3.2 mm in diameter or less, the end effector parts are very small. A blade 154 having few millimeters in length and less for its height can be easily forced from between the jaws 120, 130 and/or bent if it is not properly protected. To prevent undesirable orientations and/or conditions from occurring, each of the jaws 120, 130 is provided with an internal blade control trough 132, shown in FIG. 2, for example. This trough 132 provides a guiding surface along which the blade body 150 can move and between which the blade 154 travels. It is desirable for the blade body 150 and blade 154 to travel in the respective troughs of the jaws 120, 130 substantially without friction. It is not necessary for a part of the blade body 150 to touch the control trough 132 so long as the trough 132 provides a position-limiting area for the blade body 150 in the longitudinal and transverse directions. If the blade body 150 and/or blade 154 is permitted to move distally while the jaws 120, 130 are open to such an extent that the blade 154 is no longer within the troughs, then forces from the environment, for example, imparted from tissue present between the jaws 120, 130, can cause undesirable lateral movement of the blade 154 or blade body 150. With such small dimensions, even a small amount of lateral movement could damage the blade body 150 and/or the blade 154 and, if plastically bent in the lateral direction, could prevent the jaws 120, 130 from closing—which would prevent the end effector 100 from being removed, for example, from a channel in which the control shaft is present, such as when in a lumen of a trocar or a multi-channel endoscope. The bosses 156 and the blade control device 170 are present for this desired control.

FIG. 2 shows the end effector 100 with the lower jaw 120 removed. In this figure, it is possible to see the distal shape of the clevis 110, especially near the bosses 156 at the distal end of the blade body 150 near the blade 154. It can be seen that a boss stop cavity 112 is present and has an interior shape corresponding to the exterior shape of the boss 156. If a boss 156 is present on both sides of the blade 154, then a corresponding boss stop cavity 112 is present in a manner corresponding to the configuration illustrated in FIG. 5, for example, but on the other side of the blade 154. The boss stop cavities 112 provide a secure position for the blade 154 and blade body 150 when the blade body 150 is biased in the proximal direction. As can be seen, the cavities 112 prevent the blade from moving up or down in the plane of the blade 154 and the cavity in which the blade 154 is present in the clevis 110 prevents rotation of the blade 154 or blade body 150 therein.

As stated above, it is desirable for the blade 154 to be disposed within the troughs of the jaws 120, 130 at all times when it is extended from the retracted position shown in FIG. 2, for example. In order to provide this control, reference is made to FIGS. 6 to 9. As can be seen in FIG. 6, a blade-extension control boss 134 on the interior side of each jaw 120, 130 provides a blocking surface 136 that is absent from the travel line of the blade boss 156 as the blade 154 is extended because the jaws 120, 130 are substantially closed and in-line with the outer surface of the clevis 110. In this closed orientation, if it is desired to extend the blade body 150 between the jaws, the bosses 134 would not prevent such movement. As shown in FIG. 6, the blade-extension control boss 134 has a jaw-max-open control surface 138 at a distance from the bottom of the boss cavity 112. As such, the jaw 130 can be moved from the closed position of FIG. 6 to the max-open position of FIG. 7 and still permit distal movement of the blade 154. As used herein, the "max-open position" of the jaws is a position where the jaws are open and the blade 154 is still protected within the troughs of the jaws 120, 130. So, if the jaw(s) is (are) open at the max-open position of FIGS. 7 and 8, then the blade 154 can be extended to its fully distal position shown in FIG. 8. As is clearly shown, the blade 154 still resides within the control trough 132. In this distal-most position, it becomes apparent that the jaw 130 has a second proximal control device 139 (see FIG. 8) extending proximally from the proximal end of the jaw 130. In any extended position of the blade 154, the second proximal control device 139 is in a position where it does not block distal movement of the blade control device 170. In other words, from the closed position of the jaws 120, 130 to the max-open position of the jaws 120, 130, the second proximal control device 139 remains below (as viewed in FIG. 8) the blade control device 170.

In contrast to the above, when the jaws 120, 130 are open past the max-open position, the blade 154 should not be allowed to extend out from the clevis 110. The feature of the end effector 100 that prevents such extension from occurring is, for example, the blade-extension control boss 134. As the jaws 120, 130 open past the max-open position, the blade-extension control boss 134 necessarily moves directly distal (in front of) the blade boss 156 as shown in FIG. 9. In this orientation, the blade 154 is prevented from distal movement by the blade-extension control boss 134.

Figure 11:
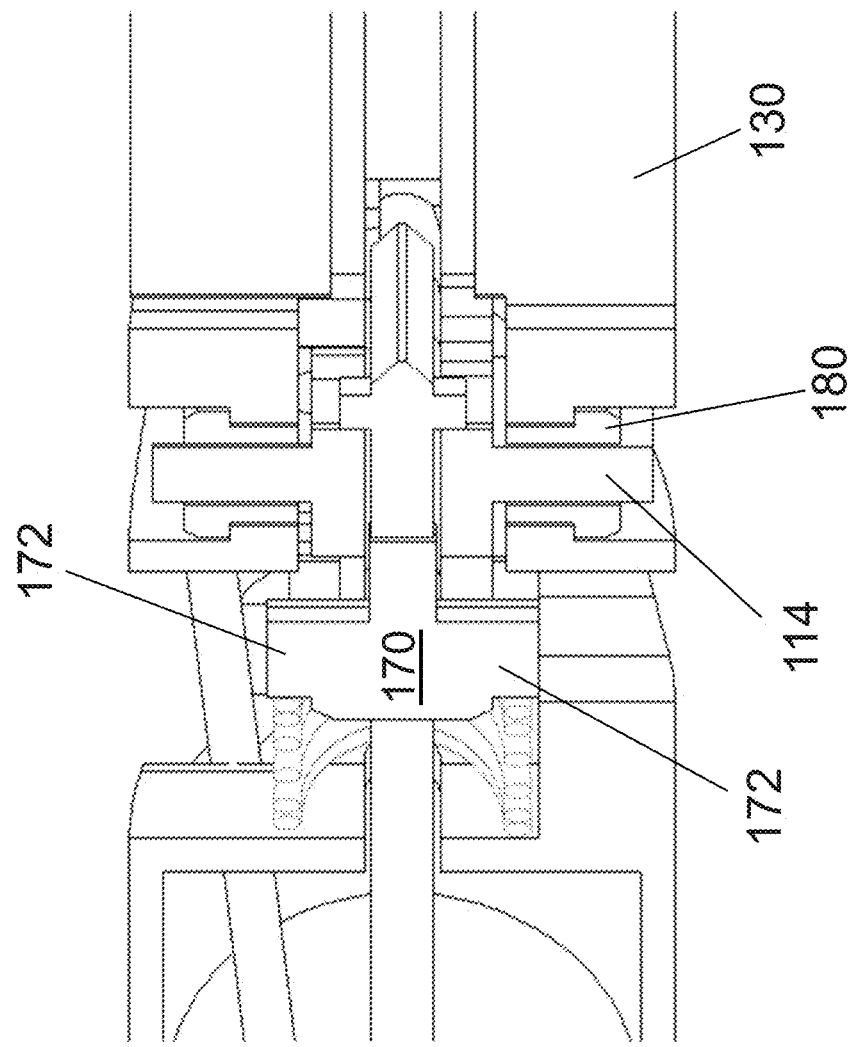
FIG. 11 is a fragmentary, longitudinally cross-sectional view of the end effector of FIG. 1 in a third longitudinally cross-sectional plane transverse to the blade plane and through a blade control device.
Figure 13:
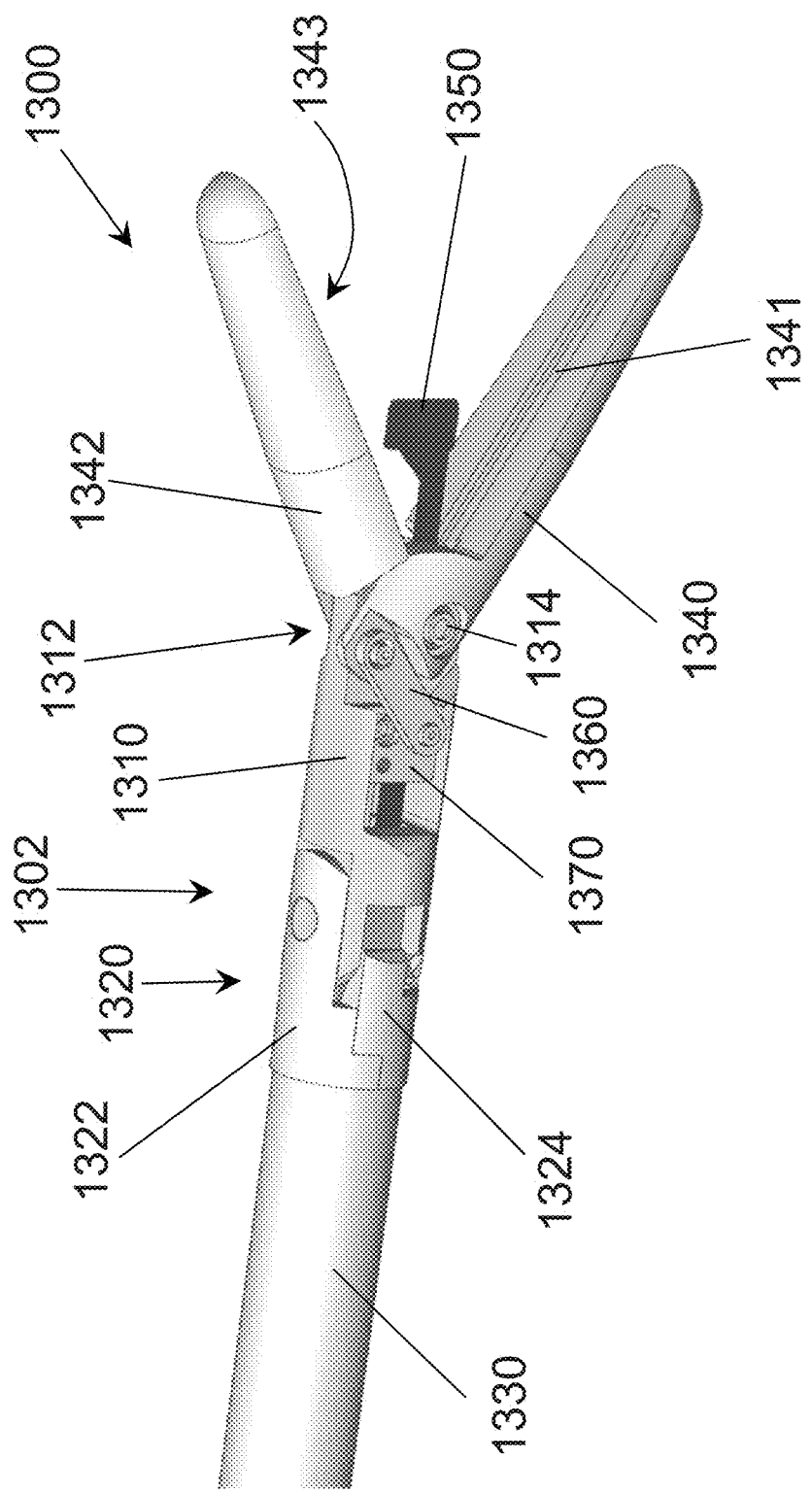
FIG. 13 is a fragmentary perspective view of an exemplary embodiment of a passive articulating electrocautery sealing and cutting surgical device according to the invention with the jaws in an open orientation past a max-open position, a blade in a partially extended position, and an articulation joint in an aligned articulation position.

As the blade body 150 moves distally, the blade control device 170, forced distally by the blade lock bias device 160, moves distally along with the position of the distal end of the control slot 152. As best shown in FIGS. 4 and 11, the blade control device 170 has at least one transverse portion 172 extending orthogonal to the longitudinal axis of the end effector 100, for example, in the same direction as the blade boss 156. As such, the blade control device 170 can move distally forward along with the blade body 150, but only for a limited distance. Each of the jaws 120, 130 has the second proximal control device 139 as shown in FIG. 9. Therefore, with the second proximal control device 139 directly distal of the transverse portion 172, the blade control device 170 is not permitted to move distal of the position shown in FIG. 9. When both of the jaws 120, 130 are within their respective max-open positions, the blade body 150 can move distally. See FIG. 8, for example. More specifically, when the blade control device 170 moves forward from the disengaged position, for example, shown in FIG. 7, to the engaged position, for example, shown in FIG. 8, each jaw 120, 130 is prevented from opening any further than the max-open position. The advantageous feature allowing the blade body 150 to extend distally when the jaws 120, 130 are open less than the max-open position is presented by balancing the relative positions of the blade bosses 156 and the radial location of the second proximal control devices 139 on each of the jaws 120, 130.

Another advantageous feature of the end effector 100 is that the jaws 120, 130 can pivot, in the plane of the blade 154, while the blade 154 is extended. As apparent in FIG. 8, the jaw 130 can "rock" upwards from the down-most position until it is prevented from further upward movement by the interior surface 137 of the tang of jaw 130. This permitted rocking movement is especially advantageous for tracking within a channel of an endoscope, for example. The second proximal control device 139 also acts to limit the opening extent of each jaw when the blade body 150 is extended in any amount.

The end effector 100 described herein can be used as a medical cauterization device, in addition to a cutting device. This means that, to cauterize tissue between the jaws 120, 130, it is desired to pass current between the two opposing tissue-contacting inner jaw faces 135. If the parts touching the jaws 120, 130 were not appropriately insulated, then current would pass between the jaws 120, 130 in a short circuit. To prevent such short-circuiting from occurring, in this exemplary embodiment, various end effector parts are insulated. First, with respect to the embodiment illustrated in FIGS. 1 to 11, it is noted that each of the two jaw actuation wires 20, 30 is used to pass current to the respective connecting jaw 120, 130. To prevent electrical short circuiting of these wires 20, 30 from the non-illustrated proximal control handle to the end effector 100, the wires 20, 30 are provided with an electrical insulator over their entire extent except for the non-illustrated connections at the control handle and the electrical connection portions 32 adjacent the tangs of the jaws 120, 130. The insulator can be of any appropriate electrically insulating material, for example, a coating or a deposition. The clevis 110 is also provided with an electrical insulator on all or part of its exterior surface. If the entire clevis 110 is so coated, there is no chance of short-circuiting the electrical current passing through the wires 20, 30. Similarly, at least the blade body 150 is provided with the electrical insulation. With such insulation, the possibility of passing current through the cutting actuation wire 10 is prevented, or substantially eliminated. If desired, the bias device 160 can be electrically insulated as well. At this point, electrical current can be presented to the entirety of the jaws 120, 130. By selective placement of an electrical insulator, the electrical current can be made to pass only through the inner faces 135 of the jaws 120, 130. More specifically, if the entirety of the jaws 120, 130 except for the inner jaw faces 135 is provided with an electrical insulator, then any electrical current passing between the wires 20, 30 will only pass between the two opposing faces 135. To insure that current does not pass from either jaw 120, 130 to the clevis 110 at the jaw pivot bosses 114, especially where the jaws 120, 130 have frictional contact with the pivot bosses 114, a jaw pivot bushing 180 made of an electrical insulating material or covered with such a material is provided between the respective jaw 120, 130 and pivot boss 114. See, e.g., FIG. 10.

One exemplary embodiment for insulating the wires 20, 30 includes a polyamide coating. An exemplary embodiment for providing insulated jaws 120, 130, includes an anodized hardcoat of polytetrafluoroethylene (PTFE) with the inner jaw faces 135 having the coating removed or with the jaws 120, 130 coated everywhere except the faces 135. Another exemplary embodiment for such a coating is a hard-coat anodization, which will provide wear resistance and lubricity where present.

Figure 12:
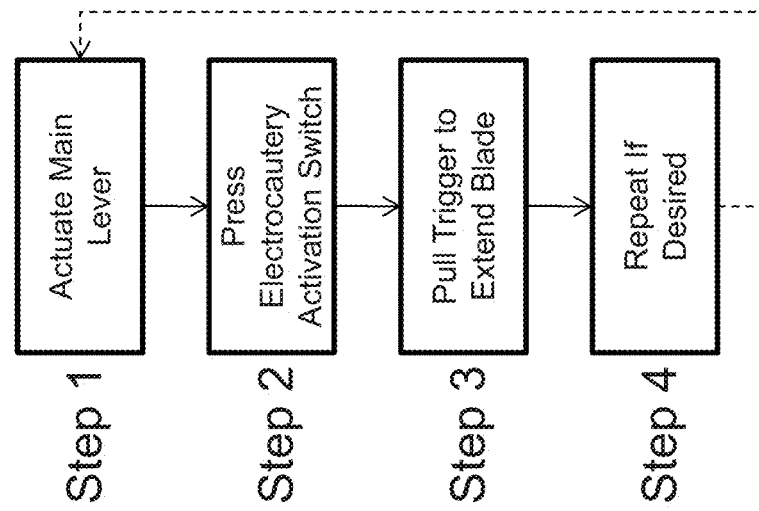
FIG. 12 is a process flow diagram illustrating the steps for operating a prior art electrocautery sealing and cutting surgical device.

The actuation assemblies of the present invention reduce the number of steps to effect the sealing and cutting surgical procedure. This improvement is illustrated and explained with respect to FIG. 12, in which four steps are illustrated to perform an electrocautery sealing and cutting procedure with the invention. With the device jaws in the normally open position, in Step 1, the surgeon closes the jaws by actuating a main lever. With the first pulling motion, the jaws close and impart the sealing force to the tissue or vessel. In Step 2, the surgeon actuates electrocautery and seals the tissue. In Step 3, the surgeon pulls a trigger to move the cutting blade distally and the sealed tissue is cut. Typically, the blade is retracted upon release of the trigger. The surgeon, in Step 4, if desired, repeats the process (dashed line).

It is beneficial if electrocautery is effected when tissue is at an optimal state for a desirable medical change to occur after the sealing and cutting procedure. Therefore, within the steps of compressing the tissue and carrying out electrocautery for sealing (but before cutting), the device can be configured to carry out an OTC-determination step. This determination can be carried out in various ways. In one exemplary embodiment according to the invention, electrodes on either side of the tissue sense an impedance of the tissue disposed between the jaws (e.g., at the jaw mouth surfaces). OTC can be determined by comparing the measured impedance to a known range of impedances value corresponding to an OTC state of the tissue. As the tissue desiccates, the impedance of the tissue changes. Therefore, the active feedback circuitry can be provided to continuously monitor the impedance and to indicate to the surgeon to open or close the jaws accordingly (with appropriate indicators at the control handle, e.g., ↑=open or ↓=close) so that the OTC state is maintained up to and including the time that sealing and cutting is performed.

The OTC feedback device performs particularly well when coupled to a mechanism for closing and opening the jaws. Passing an upper OTC value in a positive direction means that too much pressure is being imparted on the tissue and the motorized jaws are opened to an extent that brings the measured value back within the OTC range. In contrast, passing the lower OTC value in a negative direction means that too little pressure is being imparted on the tissue and the motorized jaws are closed to an extent that brings the measured value back within the OTC range. This self-adjusting compression device keeps compression force on the interposed tissue within the OTC compression range during and after desiccation. When in the OTC range after desiccation, the device notifies the surgeon of this fact, referred to as a "procedure-ready state." With this information, a delay can be pre-programmed in the device so that the sealing does not occur until after a time period expires, for example, any amount of time up to 5 seconds. In one exemplary embodiment, if the actuation device is pressed again, then the procedure is aborted and the surgeon can reposition the jaws or entirely abort the operation. If the surgeon does nothing during the delay period, then the device automatically starts the sealing procedure. Indicating information for the procedure-ready state can be conveyed to the surgeon audibly (e.g., with a speaker), visually (e.g., with an LED), or tactilely (e.g., with a vibration device).

In another exemplary embodiment of the device, the end effector is passively articulated with respect to the shaft/handle of the device as described in U.S. Pat. Nos. 7,404,508 and 7,491,080, previously incorporated by reference. FIGS. 13 to 16 illustrate a first exemplary embodiment of a distal end of a passive articulating electrocautery sealing and cutting surgical end effector 1300 of the present invention. The end effector 1300 has an articulation joint 1302 in an aligned or centered articulation position (as compared to FIG. 17, which shows the articulation joint of the invention in a left-articulated position).

In this exemplary embodiment of the articulation device, a distal articulation joint portion 1310 also acts as a jaw clevis 1312 and a proximal articulation joint portion 1320 is formed from upper and lower proximal articulation parts 1322, 1324. These parts 1322 and 1324 are fixed to the distal end of an outer shaft or sleeve 1330, which connects a non-illustrated control handle to the end effector 1300. Electrocautery jaws 1340, 1342 are attached rotatably to the jaw clevis 1312. A cutting blade 1350 is disposed between the jaws 1340, 1342 and rides within blade control troughs 1341, 1343 similar to trough 132 of the embodiment of FIGS. 1 to 11 to prevent the blade 1350 from being displaced laterally to an impermissible extent. Control of each of the jaws 1340, 1342 is effected, first (in a proximal direction) by a respective link 1360, 1562 rotatably connected to each of the jaws 1340, 1342. The link connection point is located offset from the pivot point 1314 or, in the embodiment show, the pivot boss. The boss 1314 extends from the clevis 1312 and through or inside a pivot hole of the respective jaw 1340, 1342. With appropriate fastening, the jaw 1340, 1342 remains pivotally connected about the pivot point 1314. A similar jaw boss extends, parallel to the axis of the pivot hole, from the jaw 1340, 1342. A distal end of the link 1360, 1562 is mounted pivotally about this jaw boss. In such a configuration, force exerted upon the proximal end of the link 1360, 1562 will pivot a respective jaw about its own pivot point 1314.

The proximal end of the link 1360, 1562 is pivotally connected to a jaw drive block 1370 disposed slidably within the distal articulation joint portion 1310. Like the jaws 1340, 1342, the block 1370 has a drive boss extending therefrom through a proximal boss hole of the link 1360, 1562. With the link 1360, 1562 secured in this manner, any longitudinal movement of the block 1370 within the distal articulation joint portion 1310 will cause a pivoting motion of each the jaws 1340, 1342, thereby causing jaw opening and closing movements. The exemplary boss-and-hole connections mentioned above are only included as example connections and any similar kind of connection, including reversal of the connection is envisioned for the invention.

With the distal articulation joint portion 1310 removed, it is apparent in FIG. 14 that the jaw drive block 1370 is connected at its proximal end to a jaw actuator 1390 that, in this illustration is a rectangular-cross-sectioned drive band. This band 1390 is flexible, at least in the distal portion including the articulation joint, so that articulation of the end effector 1300 can occur. Also apparent in FIG. 14 is the control portion 1352 of the blade 1350, which, like the jaw actuator 1390, is flexible, at least in the distal portion including the articulation joint, and extends proximally back to the respective actuator at the device's control handle.

To support both the band 1390 and the control portion 1352 of the blade 1350 within the proximal articulation joint portion 1320 (partially removed and partially transparent in FIG. 14), a support block 1426 is provided. This support block 1426 can have one groove in which to support the controls 1352, 1390 (in which it would have a cross-sectional H-shape), two grooves in which to support the controls 1352, 1390 (in which it would have a cross-sectional H-shape), two holes in which to support the controls 1352, 1390 (in which it would have a bisected vertically disposed rectangular cross-sectional shape), or any other similarly functioning configuration. In the illustration shown, the support block 1426 is the first exemplary shape.

To support both the band 1390 and the control portion 1352 of the blade 1350 within the articulating portion of the joint 1302, an articulation support 1480 is provided. The articulation support 1480, in a preferred embodiment, is similar to the dogbone 1080 present in the articulation joint of the devices shown in U.S. Pat. Nos. 7,404,508 and 7,491,080 (see, e.g., FIGS. 62 and 66 therein), in that it has a groove to support rods/bands passing therethrough but is different, at least, in that the articulation support 1480 is H-shaped to define separate upper and lower supporting chambers for each of the two controls 1352, 1390 to electrically insulate the bands from one another. Functioning of the articulation support 1480 is best shown with respect to FIGS. 16 and 17.

Figure 16:
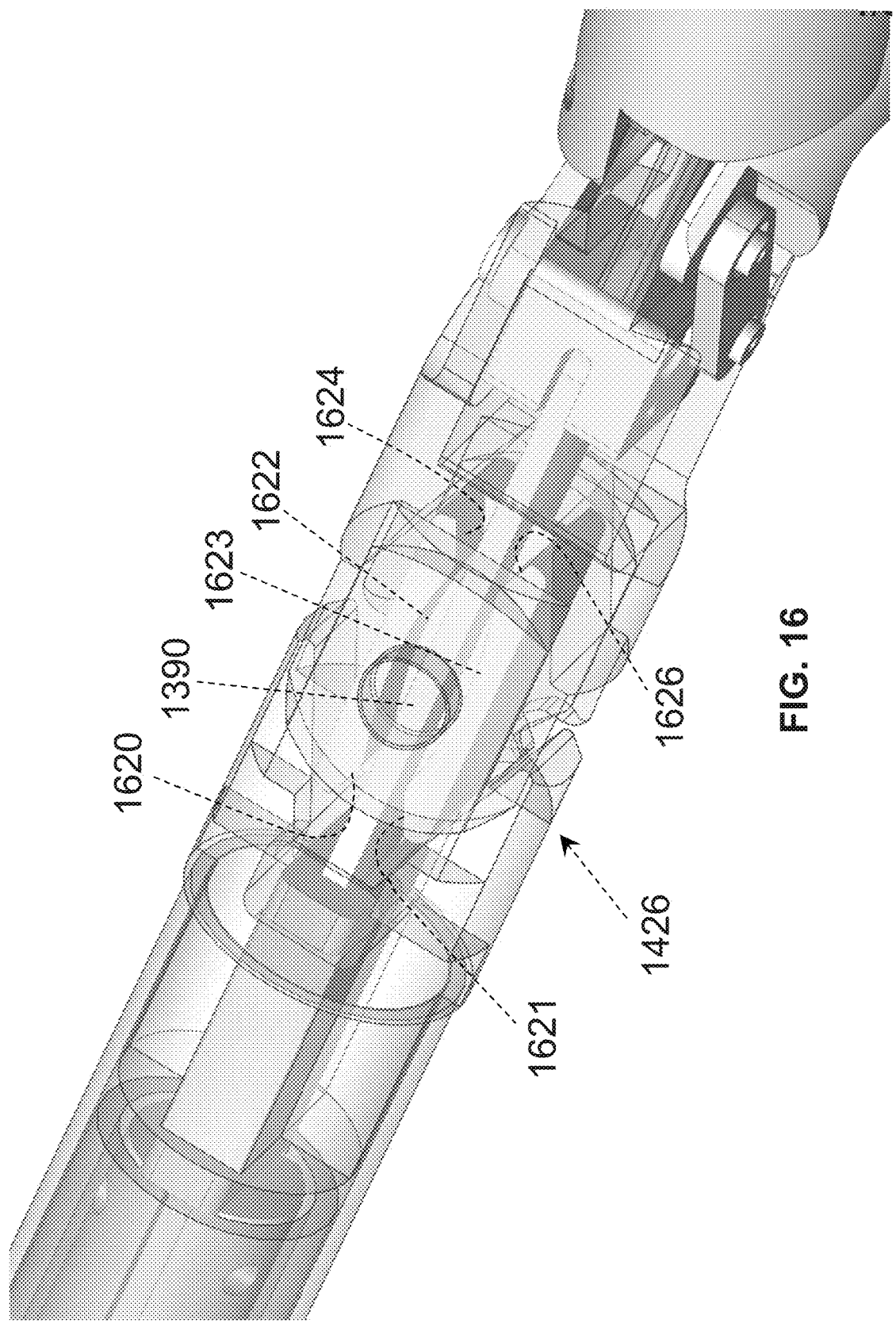
FIG. 16 is a fragmentary enlarged perspective and partially transparent view from above the passive articulating electrocautery sealing and cutting surgical device of FIG. 13 with a transparent articulation joint and a transparent outer shaft portion.
Figure 17:
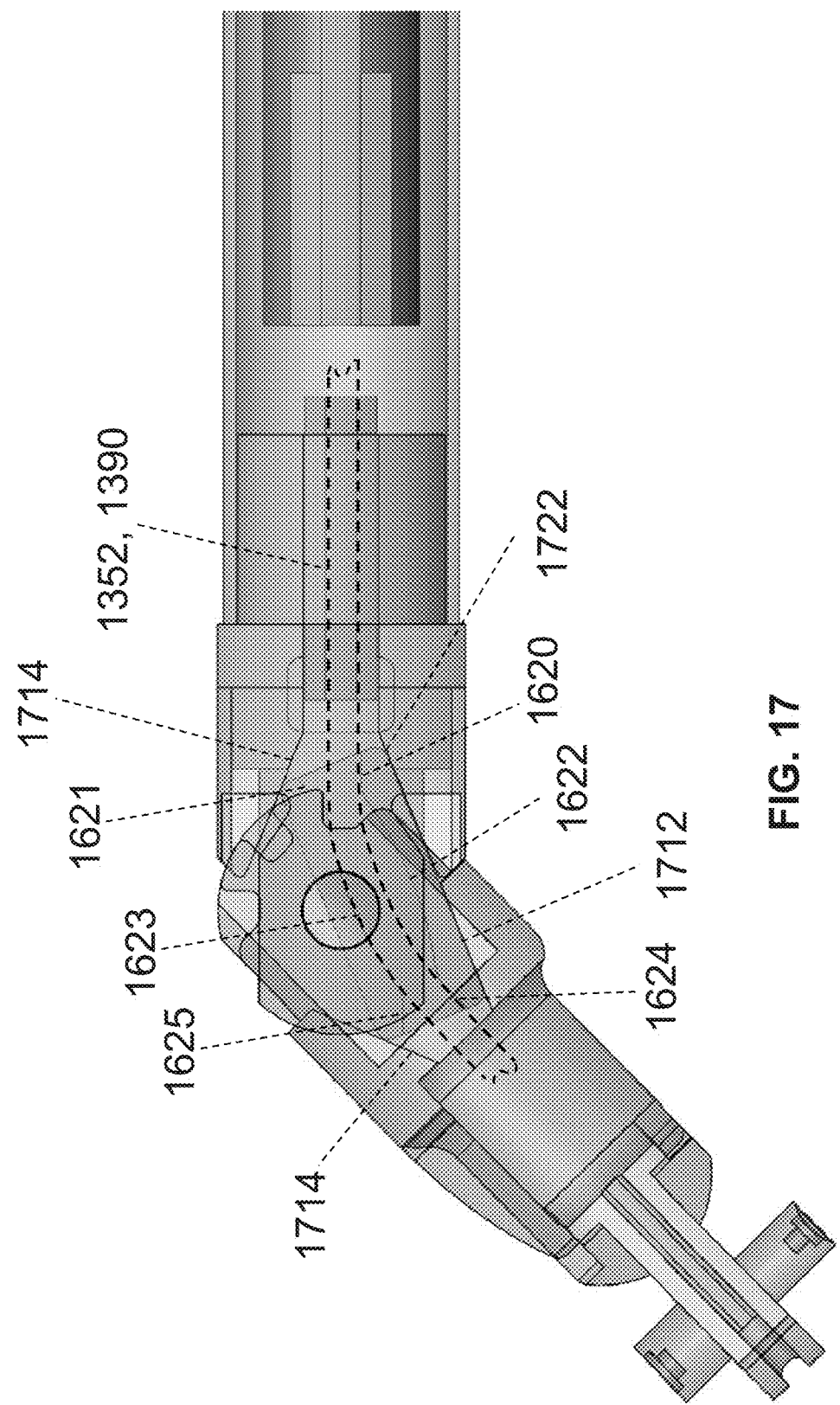
FIG. 17 is a fragmentary elevational and partially transparent view of a joint of the passive articulating electrocautery sealing and cutting surgical device of FIG. 13.

When the articulation joint 1302 is aligned or straight, the controls 1352, 1390 are also straight within the articulation joint 1302, as shown in FIGS. 14 to 16. In this orientation, the portions of the controls within the articulation joint 1302 do not touch any of the inner bearing surfaces of the articulation support 1480. These bearing surfaces include left and right proximal surfaces 1620, 1621, left and right intermediate surfaces 1622, 1623, and left and right distal surfaces 1624, 1625. When the articulation joint 1302 is articulated as shown in FIG. 17, for example, each of the controls 1352, 1390 touches at least one of these surfaces 1620-1625. One of the controls 1352, 1390 is shown diagrammatically with dashed lines in FIG. 17. When articulated, the outer surface of the control 1352, 1390 touches approximately up to the entire outer intermediate surface 1622, 1623, which, in this illustration is the right intermediate surface 1623. The left intermediate surface 1622 is free from the touch of the control 1352, 1390. In contrast, the control 1352, 1390 does not touch either of the outer proximal and distal surfaces 1621, 1625 (right in this case) but touches both of the inner proximal and distal surfaces 1620, 1624. The position shown in FIG. 17 is the far left articulated position of articulation joint 1302.

The proximal articulation joint portion 1320 and the distal articulation joint portion 1310 define a chamber in which the support block 1426 is contained. This chamber is best shown in FIGS. 16 and 17 and will be explained with regard to FIG. 17. The distal articulation joint portion 1310 define two opposing interior surfaces 1712, 1714 each at a similar acute angle with respect to the centerline of the distal articulation joint portion 1310 and opening in the proximal direction. Likewise, together, the two portions 1322, 1324 of the proximal articulation joint portion 1320 define two similar opposing interior surfaces 1722, 1724 each at a similar acute angle with respect to the centerline of the proximal articulation joint portion 1320 but opening in the distal direction.

In the configuration of FIGS. 13 to 17, electrical conduction through the two jaws 1340, 1342 is accomplished by connecting one electrical pole to the proximal end of the jaw control band 1390 at the non-illustrated control handle. In one exemplary embodiment, the control band 1390 is insulated over its entire exterior surface with the exception of the proximal connection described and a portion at the jaw drive block 1370 where the control band 1390 is connected. In an alternative exemplary embodiment, the control band 1390 is bare and all other surfaces are insulated. Electrical conduction through the link 1360 is accomplished by electrically insulating the jaw drive block 1370 all over its exterior surface except for the band 1390 connection and the surface of the jaw drive block 1370 touching the proximal pivot of the link 1360. In one exemplary configuration, the outer surface of the jaw drive block 1370 boss and the proximal borehole inner surface of the link 1360 are both be free from insulation. In the exemplary configuration of the drawings, on the other hand, the jaw drive block 1370 and the proximal borehole inner surface of the link 1360 are both insulated. In a similar manner, electrical conduction to the jaw 1340 from the link 1360 can occur by, for example, by having an insulative coating all over the lower jaw 1340 except for the inner surface of the jaw pivot hole and by not having insulative coating on the exterior of the jaw boss 1314. With an insulating sleeve 1442 electrically separating the jaw 1340 from the clevis 1312, electricity can be conducted to the jaw 1340. To insure that electricity from the jaw 1340 does not conduct to anywhere other than the mouth surface 1444 of the jaw 1340, insulation is not present at least on a portion of the mouth surface 1444.

In one exemplary embodiment of the second pole electrical conduction path, the second electrical pole is connected electrically to the proximal end of a wire 1450 (illustrated diagrammatically by a dotted line in FIG. 14). The wire 1450 extends through the sleeve 1330 and through the articulation joint 1302 by any appropriate lumen present in either part of the proximal articulation joint portion 1320 and in the distal articulation joint portion 1310. By exiting at the clevis 1312 near the pivot point of the jaw 1342, a small contact area can be left free from insulation and the wire 1450 connected there. Like jaw 1340, to insure that electricity from the jaw 1342 does not conduct to anywhere other than the mouth surface 1446 of the jaw 1342, insulation is not present at least on a portion of the mouth surface 1446.

In another exemplary embodiment of the second pole electrical conduction path, the second electrical pole is connected electrically to the proximal end of the sleeve 1330, which is insulated from the jaw control band 1390. The sleeve 1330 is electrically conductively connected to at least one part 1322, 1324 of the proximal articulation joint portion 1320. Next, the at least one part 1322, 1324 has a non-insulated surface electrically conductively connected to a non-insulated surface of the distal articulation joint portion 1310. For example, the lower surface of the upper part 1322 that slides on the upper surface of the distal articulation joint portion 1310 can both be free from insulation and remain in electrical contact as the joint articulates. If the jaw 1340 is insulated from the distal articulation joint portion 1310, then the surface facing the proximal tang of the jaw 1342 and the proximal tang can both be free from an insulating surface layer and, due to the direct sliding connection therebetween, the jaw 1342 becomes electrically conductively connected to the second pole. By insulating the remainder of the exterior surface of the jaw 1342 except for the mouth surface, the mouth surface becomes the only place that electricity can conduct from jaw 1342 to jaw 1340. One exemplary embodiment of the insulative coating for the above configuration is a TEFLON® hardcoat anodization.

FIGS. 18 to 28 show a first exemplary embodiment of a control handle 1800 of the bipolar cautery and cutting device of the present invention. Within the first control handle housing 1802, is a jaw control trigger 1810, a blade control trigger 1820, a blade-firing spool 1822, and a passive articulation lock control trigger 1830. A number of lumens/devices extend from the control handle 1800 to the end effector of the invention. The outermost hollow lumen is the sleeve 1330. Coaxially disposed within the sleeve 1330 is a hollow passive articulation lock lumen 1840. Coaxially disposed within the passive articulation lock lumen 1840 is a hollow jaw control lumen 1850 and coaxially disposed within the jaw control lumen 1850 is the distal end of the control portion 1352 of the blade 1350. Each of these devices can be in any alternative form (e.g., rod, band, hollow lumen) as desired.

The jaw control trigger 1810 is pivotally connected inside the handle 1800. The jaw control trigger 1810 has a cam surface 1812 against which a jaw cam follower 1860 moves. The jaw cam follower 1860 is fixedly connected to the jaw control lumen 1850 in the longitudinal direction of the sleeve 1330 to cause the close/open movement of the jaws as the jaw control trigger 1810 is squeezed/released. An overforce protection device 1870 is provided in the handle 1800 and limits the amount of force that is imparted upon the jaw control lumen 1850 when closing the jaws. The overforce protection device 1870, in the exemplary embodiment shown, is disposed within the jaw cam follower 1860. Not illustrated in FIG. 18 is an overforce compression spring disposed between the jaw cam follower 1860 and an overforce adjustment knob 1872. The jaw control trigger 1810 can be a simple squeeze trigger or a click-on/click-off device. FIG. 19 is an illustration of an exemplary embodiment of the latter configuration.

FIG. 18 also illustrates a battery assembly 1880 contained within the grip portion 1804 of the control handle 1800. FIGS. 20 and 21 illustrate one exemplary configuration of how the battery is placed within and removed from the grip portion 1804. A trapdoor 2010 is mounted pivotally at the bottom of the grip portion 1804 of the handle 1800. By pressing a trapdoor release button 2020, the trapdoor 2010 springs open, for example, with the assistance of a non-illustrated torsion spring. At a side of the battery assembly 1880 (for example, the upper side) is a first part 2080 of a connector assembly for removably securing the battery assembly 1880 within the grip portion 1804 of the handle 1800. Within the handle 1800 is a second part 2082 of the connector assembly that, together with the first part 2080, removably secures the battery assembly 1880 within the grip portion 1804 and electrical connects circuitry within the battery assembly 1880 to the jaws of the end effector for supplying the radio-frequency signal thereto.

As shown in FIGS. 20 and 21, the battery assembly 1880 has a trapdoor flange 2090 that operatively interacts with a battery eject flange 2012 at the pivoting end of the trapdoor 2010. In this configuration, when the trapdoor 2010 is released from its closed and locked position, the torsion spring, depending on the magnitude of its spring constant, will automatically eject the battery assembly 1880 from the handle grip 1804 to a small or large distance. In the former configuration, it is desirable for the battery to be ejected only partially so that the operating room staff can easily grab the ejected battery from the handle 1800 without touching the handle 1800 itself. In the latter configuration, the surgeon can place the handle grip 1804 over a battery disposal container and, by pressing the trapdoor release button 2020, the battery assembly 1880 will be ejected from the handle 1800 completely and will fall into the disposal container. As such, the operating room staff can easily and quickly install a replacement battery assembly 1880.

It is noted here that the handle 1800 and its internal components are entirely free from electronic circuitry. This is a unique and significant aspect of the invention. By placing all of the power generation, regulation, and control circuitry of the cautery device of the invention within the battery assembly 1880, the handle 1800 and end effector 100, 1300 can be made with entirely low-cost and disposable components. With such a configuration, all of the expensive circuitry can be reused repeatedly, at least until the circuitry or battery fails. Under expected normal conditions, the life of the battery assembly 1880 will extend to hundreds of uses.

FIGS. 22 to 28 illustrate operation of the handle 1800. In FIG. 22, the handle 1800 is in its rest state with no triggers actuated. FIGS. 23 and 24 show the jaw-closing trigger 1810 in intermediate and fully closed positions, respectively. As can be seen from FIG. 22, the jaw cam follower 1860 moves back with the jaw control lumen 1850. The jaws are fully closed when the jaw cam follower 1860 is at the position shown in FIG. 23. The remaining distance travelled by the jaw-closing trigger 1810 does not pull the jaw control lumen 1850 further proximally. Instead, the overforce protection device 1870 begins to actuate by compressing the non-illustrated compression spring disposed between the jaw cam follower 1860 and the overforce adjustment knob 1872. This configuration insures that sufficient force is employed against tissue disposed between the jaws of the end effector.

Figure 26:
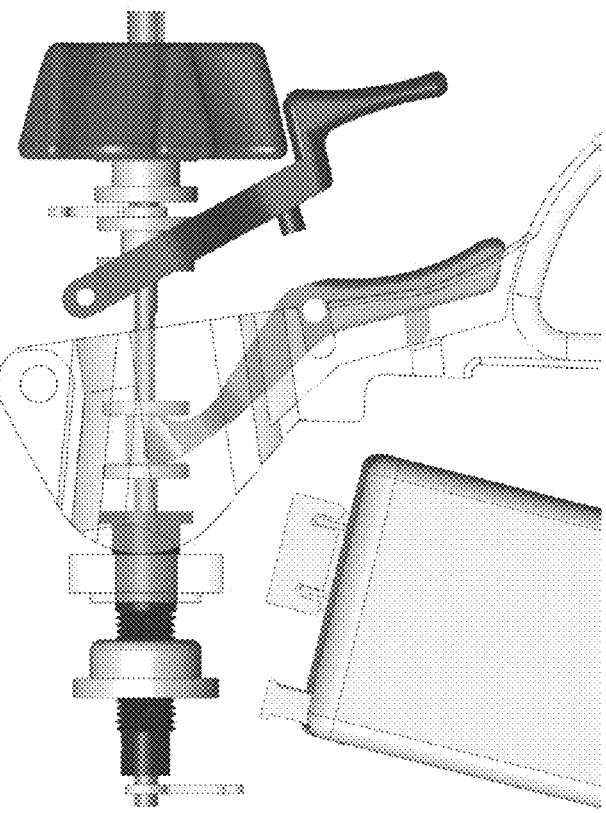
FIG. 26 is a fragmentary elevational and partially transparent view of the passive articulating electrocautery sealing and cutting surgical device of FIG. 25 with the first and second triggers partially released from the depressed position of FIG. 25.
Figure 25:
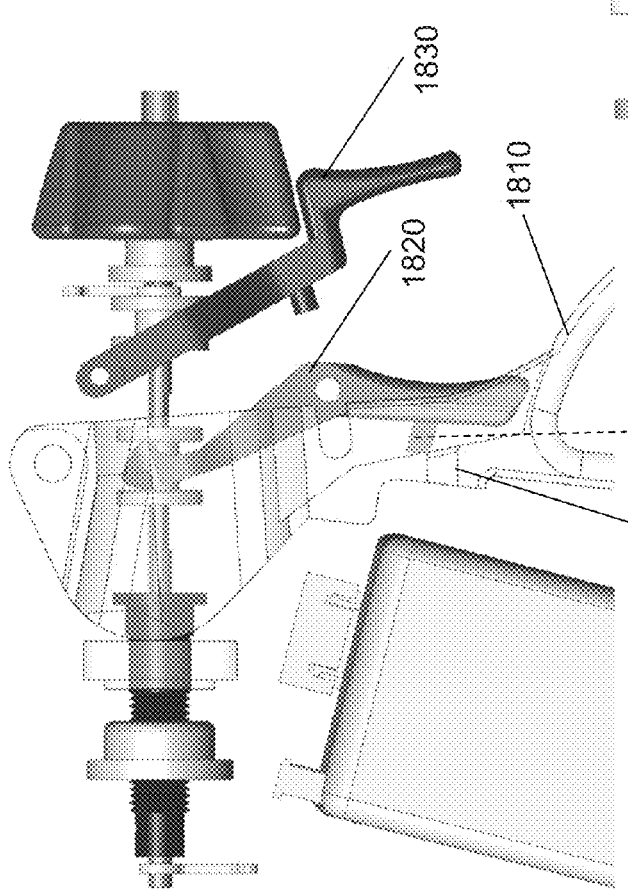
FIG. 25 is a fragmentary elevational and partially transparent view of the passive articulating electrocautery sealing and cutting surgical device of FIG. 24 with the first and second triggers depressed.

The view of FIG. 25 shows the jaw-closing trigger 1810 in the almost fully depressed position (locked by the device of FIG. 19, for example) and the blade control trigger 1820 also in the fully depressed position. When the blade control trigger 1820 is depressed, the uppermost end of the trigger 1820, resting inside a blade control spool 1822, moves distally to carry the spool 1822 distally along the jaw control lumen 1850. The spool 1822 is fixedly connected to the control portion 1352 of the blade 1350 through, for example, a pin 1824 that passes through the spool 1822 orthogonal to the spool axis and through the control portion 1352. In this way, any movement of the spool 1822 is translated into a corresponding movement of the blade 1350. A clearance for the pin 1824 is cut out of the bottom of the jaw control lumen 1850 as shown in FIGS. 18, 25 and 26, for example. An exemplary embodiment of the jaw control lumen 1850 has the lumen in the shape of a rod from the proximal end (shown in FIGS. 25 and 26) all the way to the articulation joint, at which point it can be shaped as shown in FIGS. 14 to 17, for example. A vertical slot can be formed all the way along the bottom of the jaw control lumen 1850 to allow for slidable translation of the control portion 1352 of the blade 1350 with respect to the jaw control lumen 1850 and to the sleeve 1330. The vertical slot also adds lateral support to the band-shaped control portion 1352 all along the extent of the jaw control lumen 1850.

Figure 27:
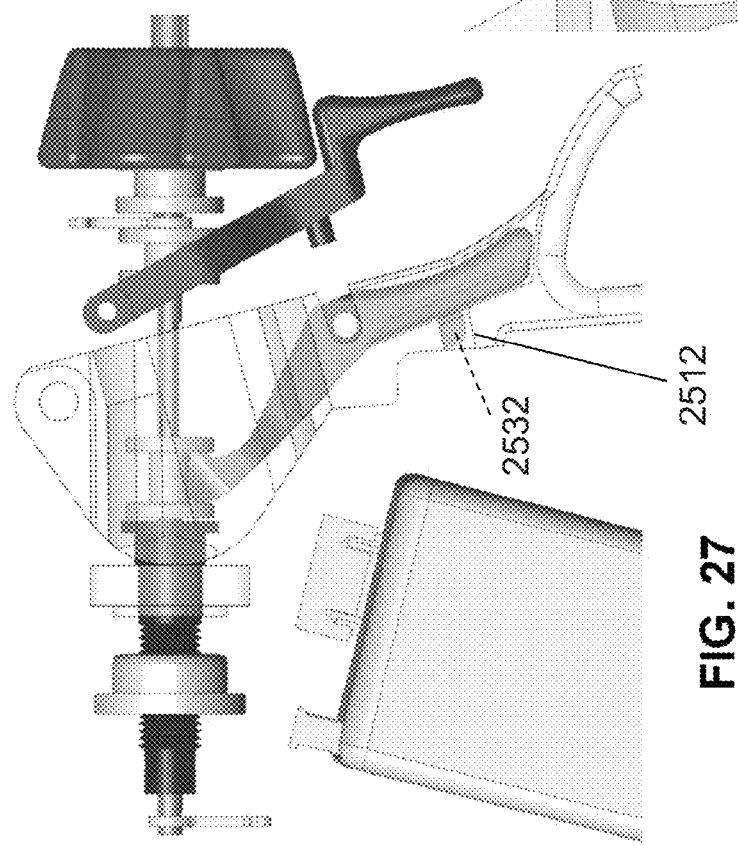
FIG. 27 is a fragmentary elevational and partially transparent view of the passive articulating electrocautery sealing and cutting surgical device of FIG. 26 with the first trigger partially released from the depressed position of FIG. 26, and the second trigger fully released.

As can be seen in FIG. 25, the blade control trigger 1820 has a proximal cam surface 2532 that fits into a cam recess 2512 when both triggers 1810, 1820 are in their rest state as shown in FIGS. 18 and 27. However, when the jaw-closing trigger 1810 is depressed, as shown in FIG. 25, the cam surface 2532 cannot reside within the cam recess 2512. This configuration is advantageous to assist with retraction of the blade 1350. If, for example, the blade 1350 were to stick inside tissue between the jaws after cutting, a proximally directed force on the control portion 1352 would be needed to remove the blade 1350. To eliminate the need for a separate blade return bias device, the invention takes advantage of the relatively strong return bias device (non-illustrated) present for the jaw-closing trigger 1810. This designed "mis-alignment" of the cam surface 2532 and the cam recess 2512 permits the jaw closing return bias device to retract the blade 1350 automatically when the jaw-closing trigger 1810 is allowed to return to its rest position. As shown in the progression of FIGS. 25 to 26, return of the depressed jaw-closing trigger 1810 presses the trigger 1810 against the cam surface 2532 up until the cam surface 2532 returns, once again, into the cam recess 2512, as shown in FIG. 27.

Figure 28:
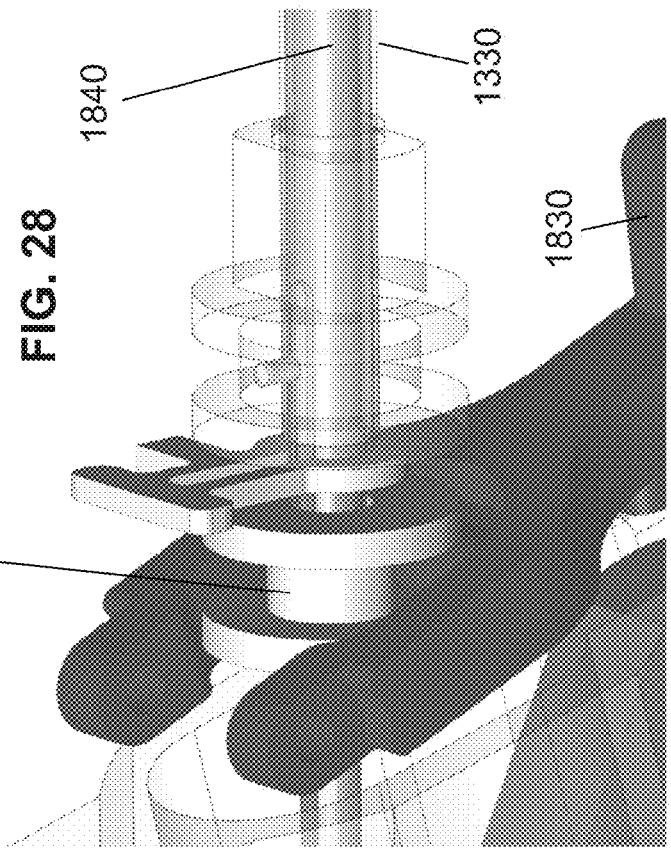
FIG. 28 is an enlarged fragmentary perspective and partially transparent view of the upper portion of the second articulation trigger of the passive articulating electrocautery sealing and cutting surgical device of FIG. 18 with the left and right side covers of the handle removed.

At any time during the steps of tissue clamping, tissue cutting, and trigger returning with the cautery/cutting device of the invention, the surgeon is able to articulate the end effector 100, 1300 as desired. FIG. 28 illustrates an exemplary configuration for unlocking the articulation joint to, thereafter, permit passive articulation of the end effector 100, 1300. The passive articulation lock control trigger 1830 is operatively connected to a hollow articulation spool 2832, which articulation spool 2832 is longitudinally fixedly connected to the passive articulation lock lumen 1840 and coaxial disposed and longitudinally slidable with respect to the jaw control lumen 1850. When the passive articulation lock control trigger 1830 is depressed, the articulation spool 2832 translates proximally and moves the passive articulation lock lumen 1840 correspondingly to remove an obstruction to passive articulation. An exemplary embodiment of such obstruction is depicted in FIG. 29. There, the passive articulation lock lumen 1840 is shown within the sleeve 1330. The distal end of the passive articulation lock lumen 1840 defines an articulation lock cutout 2942 shaped to correspond to a proximal end of an articulation locking key 2944. The locking key 2944 can be press-fitted in the cutout 2942 or attached therein in any similar manner. With the locking key 2944 attached to the end of the passive articulation lock lumen 1840, any translation of the passive articulation lock lumen 1840 will move the locking key 2944 correspondingly. In the exemplary embodiment shown, the distal end of the locking key 2944 is formed with a protrusion 2946 shaped to interlock with at least one keyhole located on the proximal end of the distal articulation joint portion 1310. In this embodiment, there are three keyholes 2912, 2913, 2914 to allow the end effector 100, 1300 to be locked in one of three orientations. Of course, this number is not limiting and neither is the placement of the keyholes 2912, 2913, 2914. Further, the key-keyhole configuration can be reversed as desired.

FIGS. 30 to 37 illustrate other exemplary configurations of a cordless, entirely self-contained cautery and cutting device of the invention. The second control handle 3000, like the first control handle 1800, has a jaw control trigger 3010 and a blade control trigger 3020. This exemplary embodiment of the control handle 3000 has a shaft rotation knob 3030, which allows the surgeon to rotate the shaft and, thereby, the entire end effector assembly at the distal end of the device. Further, this exemplary embodiment is shown without a passive articulation end effector but can include one as described herein. In such an embodiment, the knob 3030 can be pulled proximally sufficiently far to disengage the passive articulation lock, such as the locking key 2944 described above. (The mechanism is described in detail in U.S. Pat. No. 7,491,080 to Smith et al., already incorporated herein by reference, and, therefore, it is not necessary to set forth, again, this disclosure.) Simply put, a small proximal movement of the knob 3030, retracts the locking key 2944 to permit passive articulation of the articulation joint 1302 and release of the knob 3030 will allow the knob 3030 to spring distally (under the force of a return bias device, e.g., a compression spring) and re-engage the locking key 2944 with the distal articulation joint portion 1310 to prevent further passive articulation.

Also present on this handle 3000 is a cautery firing trigger 3040. With the cautery firing trigger 3040 immediately above the blade control trigger 3020, operation of the device is significantly simplified and ergonomic. When operating this handle 3000, the surgeon depresses the jaw control trigger 3010, as shown in FIG. 32, to compress the tissue between the jaws. The jaw control trigger 3010 has a blade cam flange 3112 and a proximal lever 3114. As shown in the progression from FIGS. 31 to 32, depression of the jaw control trigger 3010 causes the blade cam flange 3112 to pivot counter-clockwise away from a blade shuttle post 3142 of the blade shuttle 3144. Depression also causes the proximal lever 3114 to pivot counter-clockwise and, via a link 3146, cause a trigger sled 3118 to move proximally. Without the blade cam flange 3112 being moved from the rest position shown in FIG. 31, the cam surface 3113 is in a position preventing the blade shuttle 3144 from moving distally, thereby preventing any movement of the end effector blade until the jaw control trigger 3010 is depressed.

Figure 34:
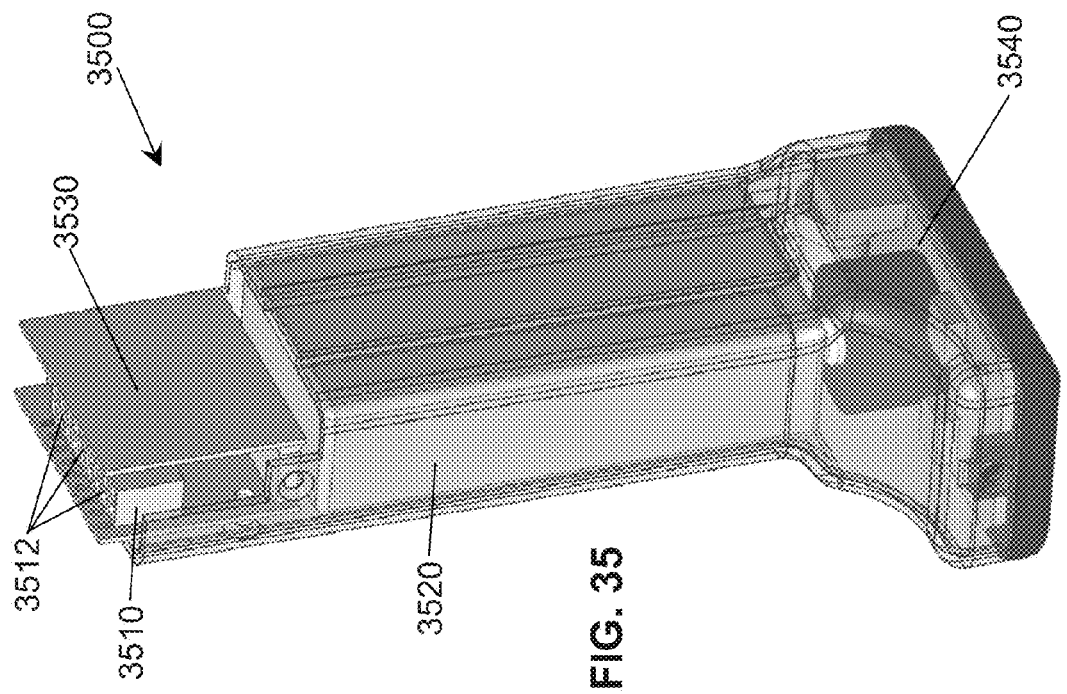
FIG. 34 is a fragmentary elevational side view of the electrocautery sealing and cutting surgical device of FIG. 30 with a left side cover of the handle removed and the battery assembly separated from the handle.
Figure 35:
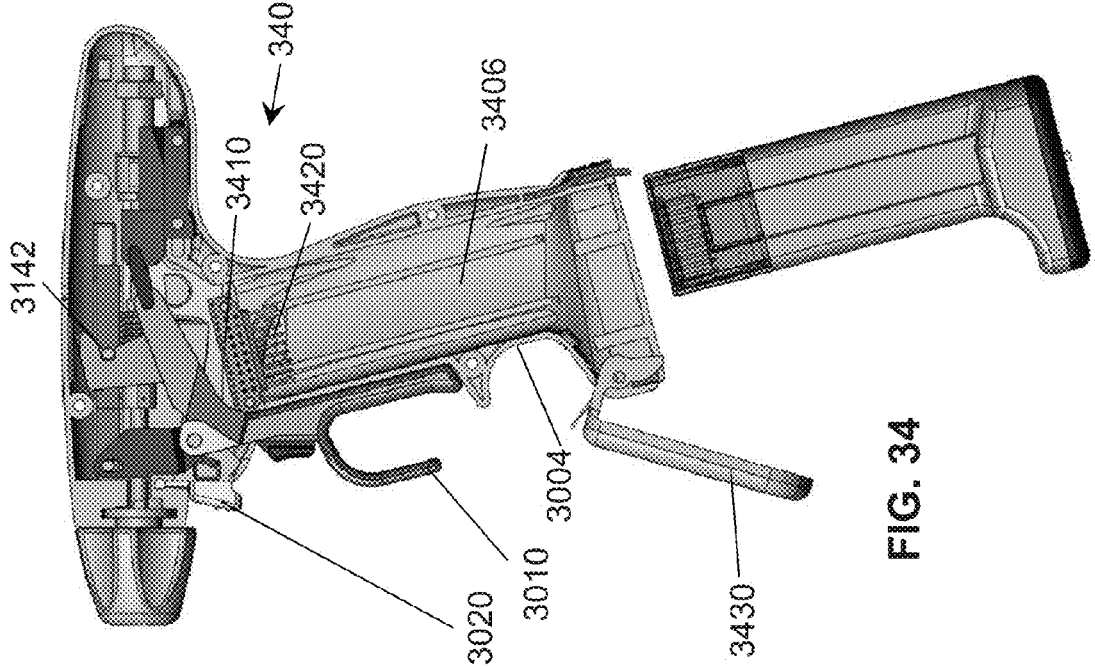
FIG. 35 is a perspective and partially transparent view of the battery assembly of FIG. 30.
Figure 43:
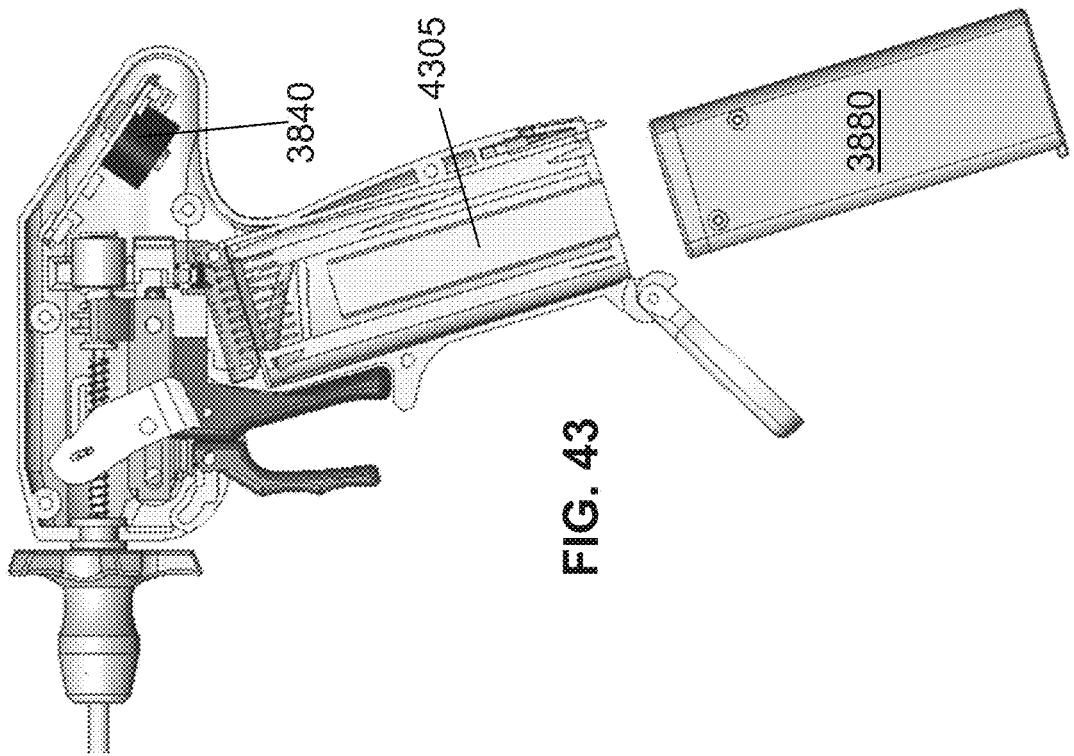
FIG. 43 is a fragmentary and partially exploded elevational side view of the passive articulating electrocautery sealing and cutting surgical device of FIG. 38 with the left side cover of the handle removed, a battery door opened, and the battery outside a battery chamber.
Figure 42:
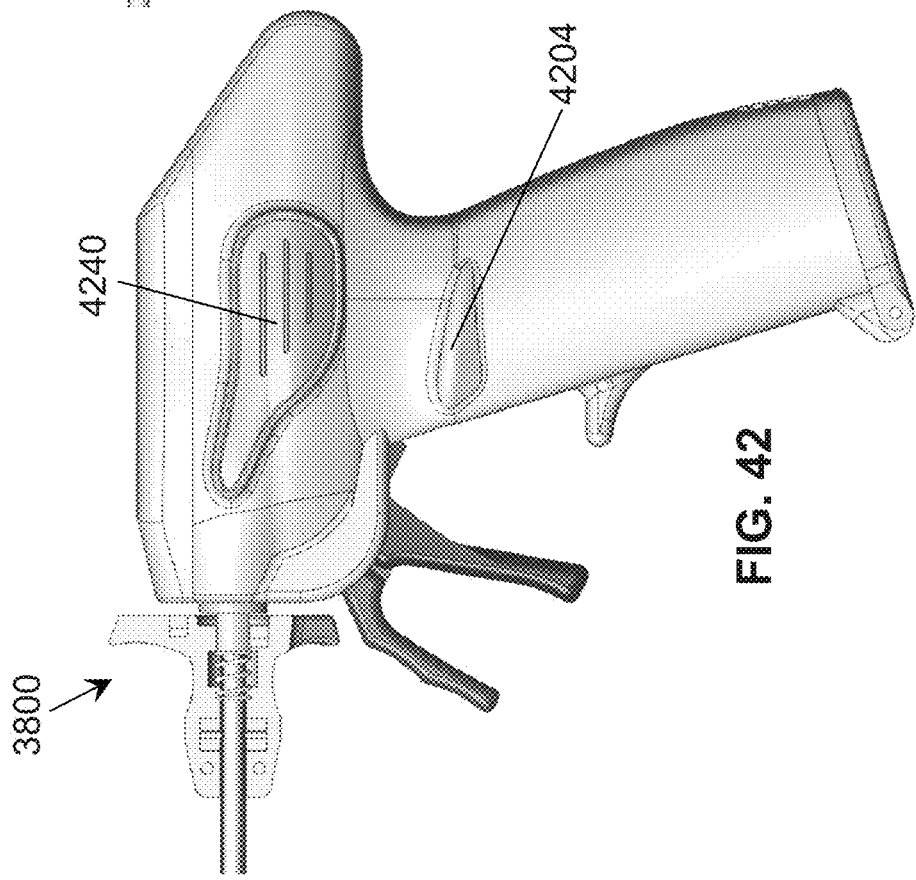
FIG. 42 is an elevational side view of the passive articulating electrocautery sealing and cutting surgical device of FIG. 38.
Figure 45:
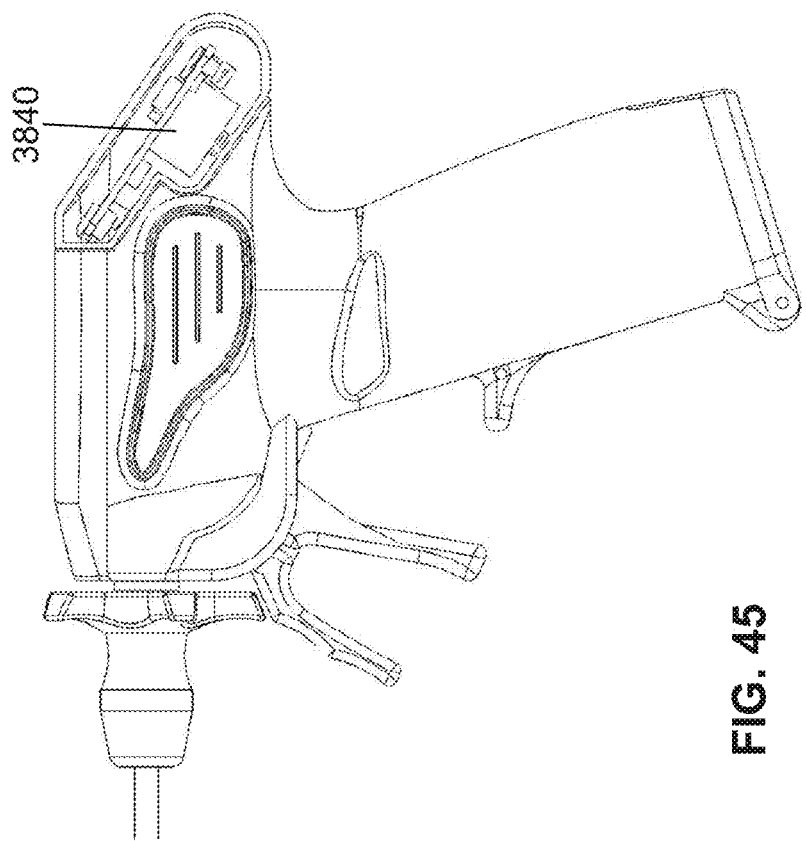
FIG. 45 is a fragmentary elevational side view and partially cross-sectional view of the passive articulating electrocautery sealing and cutting surgical device of FIG. 44.
Figure 44:
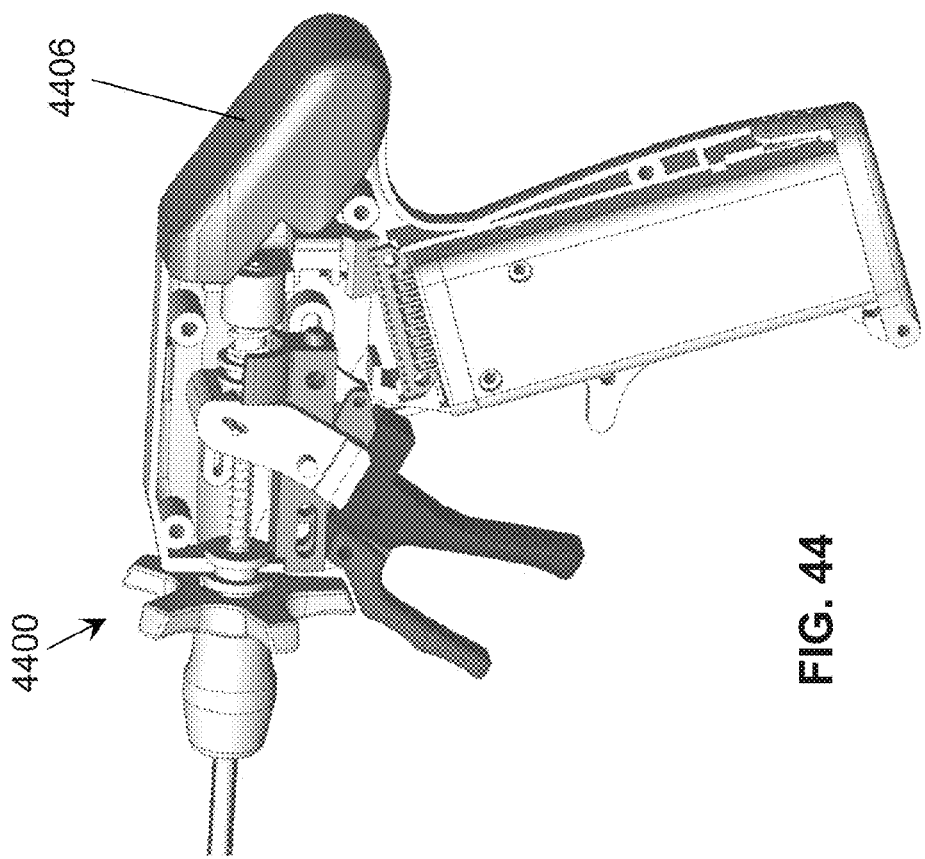
FIG. 44 is a fragmentary side perspective view of another exemplary embodiment of a passive articulating electrocautery sealing and cutting surgical device according to the present invention with a left side cover of the handle removed, a battery assembly inserted within the handle, and a removable, sealed proximal signal generation circuitry assembly.
Figure 46:
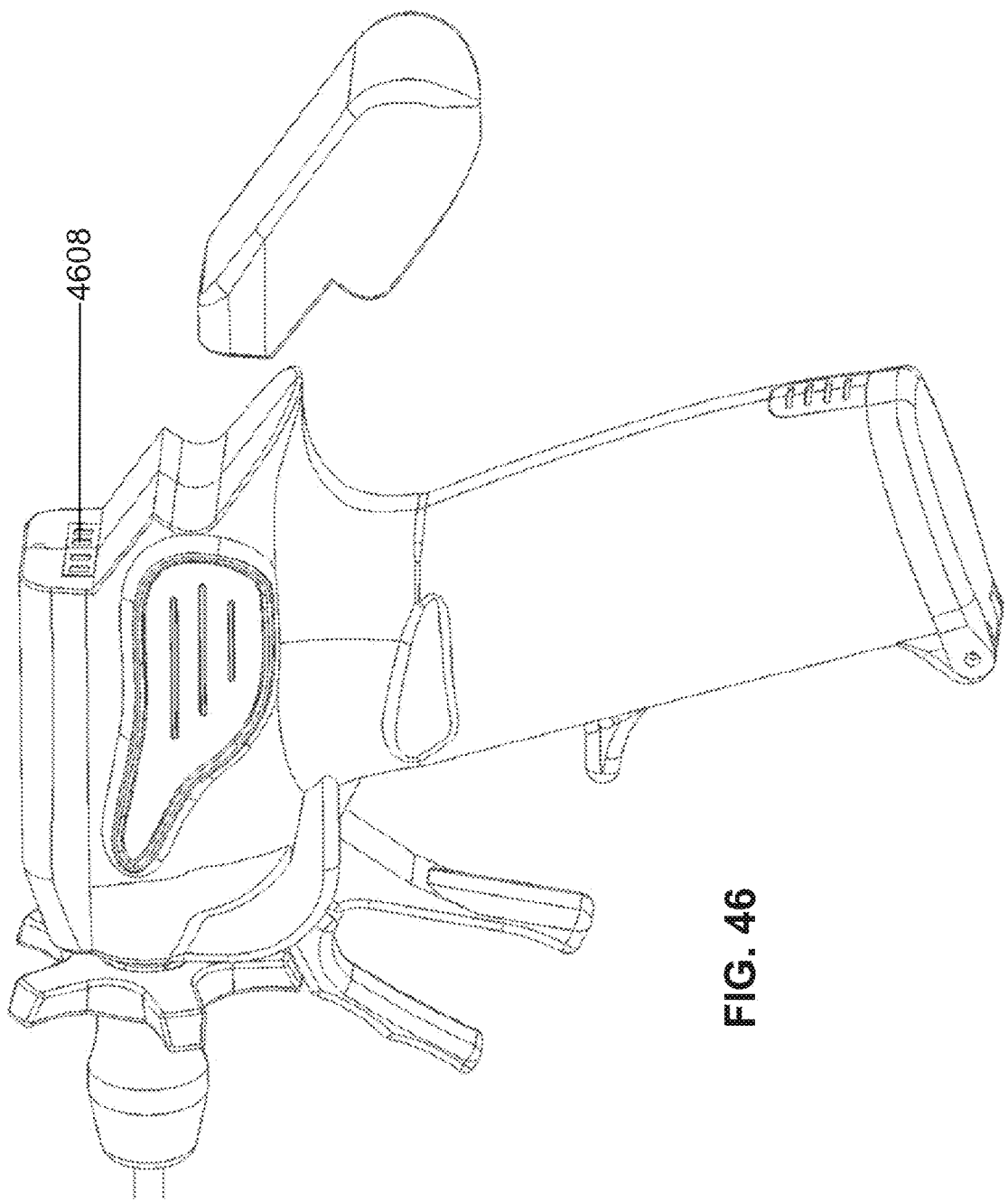
FIG. 46 is a fragmentary side perspective and exploded view of the passive articulating electrocautery sealing and cutting surgical device of FIG. 44 with the left side cover present and with the proximal signal generation circuitry assembly in a removed position.

With the jaw control trigger 3010 depressed, however, the blade shuttle 3144 is free to move distally, such depression and movement being shown in FIG. 34. In this position, the blade shuttle post 3142 rests within a slot formed by the cam surface 3113 and is prevented from moving any further distally. The distal end of the blade shuttle 3144 also has a pin within a groove that limits distal movement of the blade shuttle 3144 past the position shown in FIG. 34. A non-illustrated compression spring is disposed to move the blade control trigger 3020 distally when pressure is removed therefrom. If the blade is stuck in any way, proximal movement of the blade and blade shuttle 3144 may be halted before returning to the rest position shown in FIG. 32, for example. The cam surface 3113, however, is shaped to force the blade shuttle post 3142 proximally any time the jaw control trigger 3010 returns to the rest position shown, for example, in FIG. 30. This means that the jaw control trigger 3010 acts as a return assist for the blade and its movement assembly.

With the jaws compressing the tissue therebetween, cautery occurs by presenting the index finger (for example) at the cautery-firing trigger 3040 and depressing the cautery-firing trigger 3040. Without further movement of any part of the surgeon's single hand, the index finger can be slid downward along the cautery-firing trigger 3040 and immediately contact the surface of the blade control trigger 3020. This sliding movement of the finger can be quickly translated into a depression movement of the blade control trigger 3020 to cut the now-cauterized tissue between the jaws, which is shown in FIG. 34. At this point, the surgeon's fingers are relatively aligned with one another and are grasping the blade-firing trigger 3020, the jaw control trigger 3010, and the grip portion 3004. To restart the process again, all that the surgeon needs to do is to release the fingers holding the blade-firing trigger 3020 and the jaw control trigger 3010 and to reposition the jaws about the new tissue to be cauterized and cut. The process is, then, repeated as desired.

The battery assembly of the present invention is not simply a bipolar cauterization power supply. In prior art bipolar cautery devices, all of the power generation and regulation circuitry exists in expensive counter-top boxes, each of which is required to be plugged into an electric mains to function. A power distribution cord connects the prior art cautery device to the counter-top box, which cord limits the range of movement of the surgeon and adds cost to those devices. The invention, in contrast, entirely eliminates the need for the cord and the counter-top box by providing a self-contained power supply and regulation device 1880, 3500, also referred to herein as the battery assembly, which is explained with regard to FIGS. 34 and 35.

FIG. 34 shows a battery connection assembly with non-illustrated conductive traces connecting regulated power lines from a distribution panel 3410 to the two electrical poles for each of end effector jaws. The distribution panel 3410 has a set of conductors 3420 to be connected electrically to individual supply ports 3512 of a supply array 3510. At least one power cell 3520 (e.g., a set of 2 to 6 lithium polymer cells having a high discharge current capacity on the order of 10-15 times the rated storage capacity (known as 10-15 C) is electrically connected to voltage control circuitry 3530, which can be, for example, a buck power supply controlling the output signal voltage. Radio-frequency signal generating circuitry 3540 receives the output signal and converts it into a high-frequency alternating-current signal, which AC signal is supplied to the end effector jaws through the conductive supply ports 3512 and the distribution panel 3410.

With such a configuration, the control handle 3000 becomes entirely free from any power supply or power circuitry. This means that the relatively expensive supply and circuitry can be reused in the inventive interchangeable battery assembly 3500 and the relatively cheap handle parts of the mechanical control handle 3000 with its shaft and end effector can be thrown away after the single operative use. If desired, the relatively expensive parts can be even further subdivided as shown in FIGS. 36 and 37. The battery assembly 3600 of these figures is similar in function and shape to the battery assembly 3500. However, the radio-frequency signal generating circuitry 3540 is contained within a separable signal processing sub-assembly 3640 having a set of non-illustrated circuit connection leads on a signal connection surface(s) 3642, which leads are connected to and from the radio-frequency signal generating circuitry 3540. If the two sub-assemblies 3620, 3640 of the battery assembly 3600 are each provided with an appropriate part of a connection device, such as the tongue-and-groove configuration shown in FIG. 37, then the user has the ability to replace either the battery/boost sub-assembly 3620 or the signal processing sub-assembly 3640 as desired.

Even though it might be beneficial if the battery assembly 3500 is hermetically sealed for medical use (because the control handle defines an internal battery chamber 3406 that can be shut off from the aseptic operating environment), the battery assembly 3500 need not be autoclavable. An "aseptic seal" or "aseptically sealed," as used herein, means a seal that sufficiently isolates a compartment (e.g., inside a handle) and components disposed therein from a sterile field of an operating environment into which the handle has been introduced so that no microbiological organisms from one side of the seal are able to transfer to the other side of the seal. Further, "hermetic" or "hermetically sealed" means a seal or container that is substantially air tight and prevents microorganisms from passing across the seal or into or out of the container.

With the control handle 3000 in the operating suite, operating staff can request circulating staff outside the aseptic field to insert the battery assembly 3500 into the chamber 3406. The aseptic control handle 3000 with the inserted battery assembly can be made entirely aseptic for use in the operating room after operating staff closes the battery door 3430, which door has a hermetic seal. Of course, the battery assembly 3500 can be made to autoclave and, therefore, the battery assembly can be brought into the sterile file as desired.

Like the first control handle 1800, the second control handle 3400 also can be provided with a battery assembly ejection device. As shown in FIGS. 33 and 34, the battery door 3430 is mounted pivotally to a lower part of the grip portion 3004 of the control handle 3400. By pressing a trapdoor release button 3320, the battery door 3430 springs open, for example, with the assistance of a non-illustrated torsion spring. As shown in FIGS. 33 and 34, the battery assembly 3500 has a door cam surface 3390 that operatively interacts with a battery eject flange 3312 at the pivoting end of the battery door 3430. In this configuration, when the battery door 3430 is released from its closed and locked position, the torsion spring, depending on the magnitude of its spring constant, will automatically eject the battery assembly 3500 from the handle grip 3004 to a small or large distance. As above, the battery assembly 3500 can be ejected only partially so that the circulating staff can easily grab the ejected battery from the handle 1800 without touching the handle 1800 itself. Alternatively, any of the operating staff can place the handle grip 3004 over a battery disposal container and, by pressing the trapdoor release button 3320, eject the battery assembly 3500 from the handle 3000 completely, permitting it to fall into the disposal container. As such, the operating/circulating room staff can easily and quickly install a replacement battery assembly 3500.

The functional components of the embodiment of the third control handle 3800 in FIGS. 38 to 43 are similar to the second control handle 3000. In this embodiment, however, the trigger mechanisms operate in a different way and the radio-frequency signal generating circuitry 3840 is located in the disposable control handle 3800 and not within the battery assembly 3880.

The third control handle 3800, like the first control handle 1800, has a jaw control trigger 3810, a blade control trigger 3820, and a grip portion 3804. Here, a blade return spring 3826 provides a distally directed bias to keep a blade control spool 4022 in a proximal position (shown in FIG. 40, for example) and, thereby, the blade in a retracted position.

Instead of an articulation lock trigger 1830, this embodiment has a rotatable knob 3830. The shaft rotation knob 3830 allows the surgeon to rotate the shaft and, thereby, the entire end effector assembly at the distal end of the device. This exemplary embodiment is shown without a passive articulation end effector but can include one as described herein.

Also present on this handle 3800 is a cautery-firing trigger 4240. In this embodiment, the cautery-firing trigger 4240 is immediately above a thumb rest 4204 on the side of the grip portion 3804 of the control handle 3800. The cautery-firing trigger 4240 and the thumb rest 4204 can be mirror symmetrical on both sides of the grip portion 3804.

The progression from FIGS. 38 to 41 reveals a novel multi-safety-trigger assembly that prevents the blade from firing unless and until the jaws are closed. This safety-trigger assembly includes the jaw control trigger 3810, the blade control trigger 3820, a jaw trigger link 3812, a jaw trigger slide 3814, a jaw spool 3816, a blade control pivot 3822, a blade control pin 3824, a blade control spool 4022, and a jaw overforce protection device 3850. This exemplary embodiment is shown without a passive articulation end effector but can include one as described herein.

The jaw control trigger 3810 has an upper flange 3811 and a pivot 3912 about which the jaw control trigger 3810 can be rotated. The proximal end of the upper flange 3811 is connected pivotally to a proximal end of the jaw trigger link 3812. The distal end of the jaw trigger link 3812 is pivotally connected to a proximal portion of the jaw trigger slide 3814. The jaw trigger slide 3814 has a guide track 3914 in which the pivot 3912 is disposed. The proximal end of the jaw trigger slide 3814 has an upwardly projecting spool control flange 3918 engaged with the jaw spool 3816 to translate the jaw spool 3816 longitudinally as the jaw trigger slide 3814 translates longitudinally. To carry out the jaw movement motion (open/close), the surgeon exerts pressure upon the jaw control trigger 3810 towards the grip 3804 to pivot the jaw control trigger 3810 about the pivot 3912 to the position shown in FIG. 39. At the same time, the jaw link 3812 pivots and exerts a proximally directed force to the jaw trigger slide 3814 to move the jaw trigger slide 3814 to the proximal position, also shown in FIG. 39. At the end of the jaw link 3812 movement, the distal end of the jaw link 3812 is higher than the proximal end of the jaw link 3812. This movement of the jaw trigger slide 3814 causes the jaw spool 3816 to translate proximately a corresponding amount. Closing movement of the jaws is effected because the jaw spool 3816 is longitudinally connected to a jaw movement lumen 3990. With respect to the configuration shown in FIGS. 1 to 11, the jaw movement lumen 3990 is the jaw actuation wires 20, 30, and, with respect to the configuration shown in FIGS. 13 to 17, the jaw movement lumen 3900 is the jaw actuator 1390.

The blade control trigger 3820 moves, initially, with the FIGS. 38 to 39 movement of the jaw control trigger 3810 but does not cause any blade movement. A guide groove 3921 is present to prevent firing of the knife while the jaws remain open and the blade control trigger 3820 needs to be moved out of the distal vertical portion of the guide groove 3921. As can be seen best in FIG. 41, the guide groove 3921 does not allow the blade control trigger 3820 to move proximally until it enters a lower horizontal portion of the guide groove 3921, and entry cannot occur until the jaw control trigger 3810 is also in the horizontal position shown in FIGS. 39 to 41; thus, the invention ensures that the jaws are closed when the blade is required to move. Actuation of the blade control trigger 3820 from the position shown in FIG. 39 to the position shown in FIG. 40 removes the safety that prevents firing of the blade. When in the position of FIG. 40, the blade control trigger 3820 can now be translated longitudinally proximally (i.e., not in a circular motion about its pivot) from the position shown in FIG. 40 to the position shown in FIG. 41.

Present on the jaw control trigger 3810 is a blade actuation boss 3813 (which is shown within a boss groove 4024 hidden behind a lower portion of the blade control pivot 3822 in FIG. 40). As the blade control trigger 3820 (along with jaw control trigger 3810) is moved proximally, the blade actuation boss 3813 carries/transports/moves the lower end of the blade control pivot 3822 about its pivot point in a counter-clockwise direction. Correspondingly, the upper portion of the blade control pivot 3822, with its pin groove 4026 carrying the blade control pin 3824, is moved counter-clockwise about the pivot point of the blade control pivot 3822. The blade control pivot 3822 is forked at the upper portion to accommodate the blade control spool 4022 therein and to capture the blade control spool 4022 so that the blade control spool 4022 moves distally when the blade control pin 3824 is moved. The blade control spool 4022 is connected longitudinally to the blade movement lumen 4052 that causes the distal/proximal movement of the blade. With respect to the configuration shown in FIGS. 1 to 11, the blade movement lumen 4052 is the cutting actuation wire 10 and, with respect to the configuration shown in FIGS. 13 to 17, the blade movement lumen 4052 is the control portion 1352 of the blade 1350.

Operation of the device is significantly simplified and ergonomic. When operating this handle 3800, the surgeon depresses the jaw control trigger 3810 as shown in FIG. 39. The blade control trigger 3820 follows the movement of the jaw control trigger 3810 without actuating the blade. With the jaws compressing the tissue therebetween, cautery occurs by presenting the thumb (for example) at the cautery-firing trigger 4240 and depressing the cautery-firing trigger 4240. Next, as shown from the transition from FIG. 39 to FIG. 40, the blade control trigger 3820 is depressed. This action does not move the blade, however. Instead, it merely acts to unlock an ability to move the blade; in essence, it is a safety release. With the blade control trigger 3820 in the depressed position, the combined sub-assembly of the jaw control trigger 3810 and the blade control trigger 3820 can be moved proximally, as shown by the transition from FIG. 40 to FIG. 41. Such movement is not circular (as are the other embodiments described above). Rather, the movement is linear. With such linear movement, a corresponding movement of the blade and cutting of the now-cauterized tissue between the jaws is carried out. At this point, the surgeon's fingers are relatively aligned with one another and are grasping the blade-firing trigger 3020, the jaw control trigger 3010, and the grip portion 3004. To restart the process again, all that the surgeon needs to do is to release the fingers holding the blade firing and jaw control triggers 3020, 3010 (or push the fingers holding the triggers 3020, 3010 distally) and reposition the jaws about the new tissue to be cauterized and cut. The process is, then, repeated as desired.

Like the configuration of FIGS. 30 to 34, the battery assembly 3880 is removable from a compartment 4305 within the grip portion 3804 of the control handle 3800 and is interchangeable with other similar battery assemblies 3880. Ejection of the battery assembly 3880 can be carried out, for example, with a battery ejection assembly similar to the battery ejection assembly 2010, 2012, 2090 shown in FIGS. 20 and 21, but other similarly functioning assemblies can be employed as well. Unlike the configuration of FIGS. 30 to 34, the radio-frequency signal generating circuitry 3840 is not contained within the battery assembly 3880. Instead, it is located in a proximal location within the upper portion of the control handle 3800. (Of course, the circuitry 3840 can be located anywhere in the control handle 3800 in this embodiment.) In such a configuration, the radio-frequency signal generating circuitry 3840 can be disposed when the control handle 3800 is discarded.

In an advantageous alternative exemplary embodiment of the radio-frequency signal generating circuitry 3840 and disposable control handle 3800, the control handle 4400 has a removable and interchangeable circuit casing 4406, which is hermetically sealed and autoclavable. The circuit casing 4406 houses the radio-frequency signal generating circuitry 3840 and, therefore, enables the reuse of this circuitry 3840. Electrical connection of the radio-frequency signal generating circuitry 3840 can be effected with leads 4608, for example, made of gold-plated copper. Removable connection of the circuit casing 4406 can be made by many mechanical configurations. For example, a T-slide connection, a tongue-and-groove connection, a press-fit connection, and even a magnetic connection.

FIGS. 47 to 50 illustrate another exemplary embodiment of a distal end of an electrocautery sealing and cutting surgical end effector 4700 of the present invention. This end effector 4700 is not shown with an articulation joint although the articulation joint of the invention can be employed here equally. This embodiment acknowledges characteristics of forming the jaws 4710, 4720 from a solid piece of material and, based thereupon, forms each of the jaws 4710, 4720 from two pieces of different materials—the outer piece 4712, 4722 being of a material having good heat insulating properties and the inner piece 4714, 4724 being of a material having good strength properties. Each of the inner pieces 4714, 4724 has a mouth surface 4716, 4726 coated with an electrically conductive material to provide the radio-frequency signal to tissue disposed between the jaws 4710, 4720. For example, the conductor material can be plates of stainless steel or gold-coated copper. Electricity is presented to the mouth surfaces 4716, 4726 through portions of the end effector 4700 as in the previously described embodiments or, in the exemplary embodiment shown, through two insulated wires 4730, 4740 shown, respectively with differently dashed lines. Each of the wires 4730, 4740 terminates at a jaw connection 4718, 5028 and the wire is electrically connected to the conductive coating of the mouth surfaces 4716, 4726.

Figure 51:
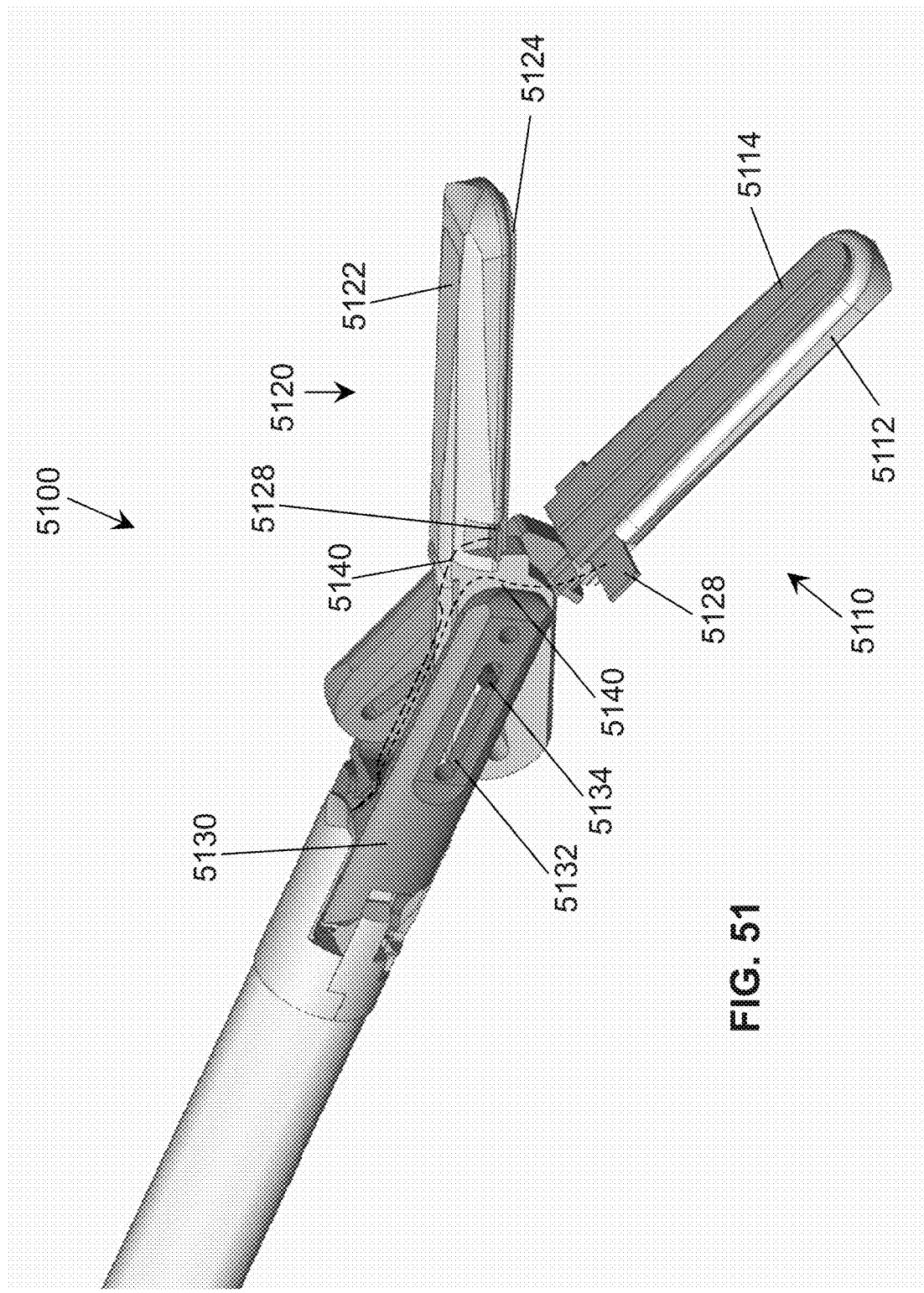
FIG. 51 is a fragmentary enlarged perspective view from a distal side of a passive articulating electrocautery sealing and cutting surgical end effector according to the present invention with the jaws past a max-open position and with the blade removed.
Figure 54:
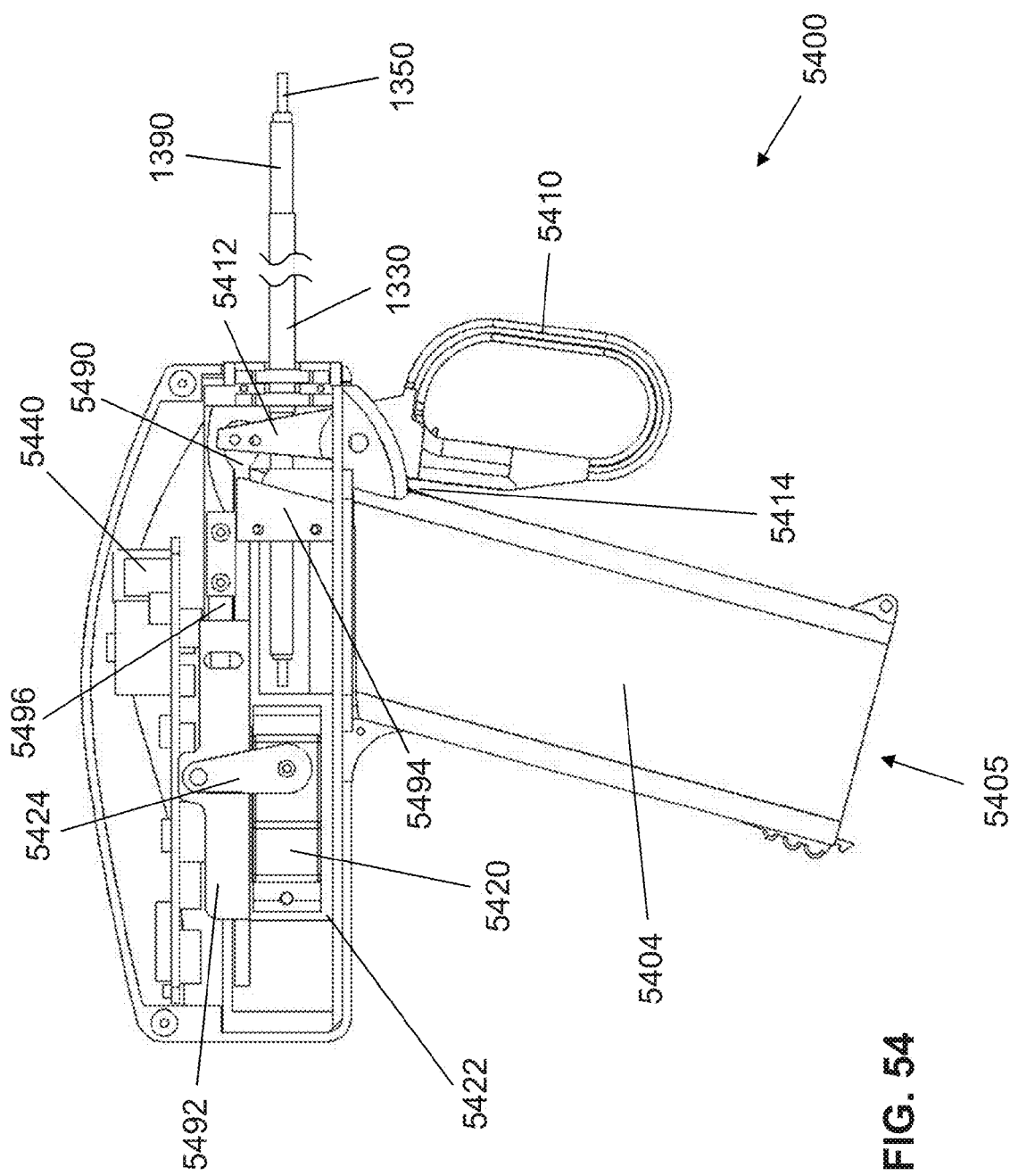
FIG. 54 is a fragmentary, side elevational view of an exemplary embodiment of a powered-blade electrocautery and cutting device according to the present invention with a right side cover and end effector removed.

FIGS. 51 to 53 illustrate another exemplary embodiment of a distal end of a passively articulating electrocautery sealing and cutting surgical end effector 5100 of the present invention. This end effector 5100 is shown with an articulation joint but the articulation joint can be removed if desired. Like the embodiment of FIGS. 47 to 50, this embodiment acknowledges the characteristics of forming the jaws 5110, 5120 from a solid piece of material and, instead, forms each of the jaws 5110, 5120 from two pieces of different materials with the outer piece 5112, 5122 being of a material having good heat insulating properties and the inner piece 5114, 5124 being of a material having good strength properties. Each of the inner pieces 5114, 5124 has a conductive mouth surface providing the radio-frequency signal to tissue disposed between the jaws 5110, 5120. For example, the conductor material can be plates of stainless steel and the outer piece 5112, 5122 can be stainless steel with an insulating covering. Electricity is presented to the mouth surfaces through portions of the end effector 5100 as in the previously described embodiments or, in the exemplary embodiment shown, through two insulated wires 5140 illustrated, respectively, with differently dashed lines. Each of the wires 5140 terminates at a jaw connection 5118, 5128 and is electrically connected to the conductive coating of the mouth surfaces of the inner pieces 5114, 5124.

In contrast to the previous end effector embodiments where the jaws have independent pivoting devices, the end effector 5100 includes a single jaw pivoting assembly. In this embodiment, each side of the clevis 5130 has a jaw pivot slot 5132 in which slides a jaw pivot rod 5134. As best shown in FIG. 53, the proximal portion of each of the jaws 5110, 5120 defines a control slot 5326, 5328 in which the jaw pivot rod 5134 slides. A jaw control rod 5330 is connected longitudinally to the jaw pivot rod 5134 and longitudinal movement of the jaw control rod 5330 causes the jaw pivot rod 5134 to slide along the jaw pivot slot 5132 and move correspondingly within the control slots 5326, 5328 of the jaws 5110, 5120. As shown in FIGS. 51 to 53, distal movement of the jaw control rod 5330 opens the jaws 5110, 5120 and proximal movement of the jaw control rod 5330 closes the jaws 5110, 5120.

Articulation of the end effector 5100 is carried out at a control handle. When a passive articulation lock control trigger is actuated, a passive articulation lock lumen 5340 is moved proximally to remove an obstruction to passive articulation. An exemplary embodiment of such obstruction is depicted in FIGS. 52 and 53. There, the passive articulation lock lumen 5340 is shown within the sleeve 1330. The distal end of the passive articulation lock lumen 5340 defines an articulation lock cutout 5342 shaped to correspond to a proximal end of an articulation locking key 5344. The locking key 5344 can be press-fitted in the cutout 5342 or attached therein in any similar manner. With the locking key 5344 attached to the end of the passive articulation lock lumen 5340, any translation of the passive articulation lock lumen 5340 will move the locking key 5344 correspondingly. In the exemplary embodiment shown, the distal end of the locking key 5344 is formed with a protrusion 5346 shaped to interlock with at least one keyhole located on the proximal end of the clevis 5130. In this embodiment, there are three keyholes 5332, 5333, 5334 to allow the end effector 5100 to be locked in one of three orientations. Of course, this number is not limiting and neither is the placement of the keyholes 5332, 5333, 5334. Further, the key-keyhole configuration can be reversed as desired.

Figure 65:
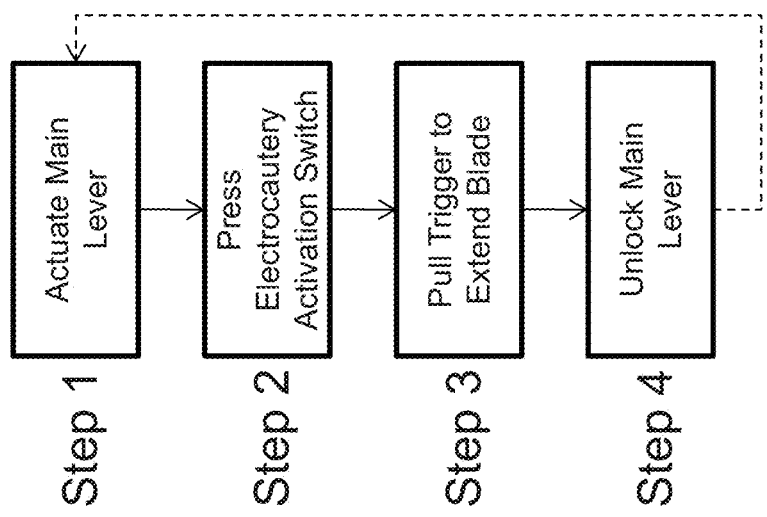
FIG. 65 is a process flow diagram illustrating the steps for operating a prior art electrocautery sealing and cutting surgical device.
Figure 66:
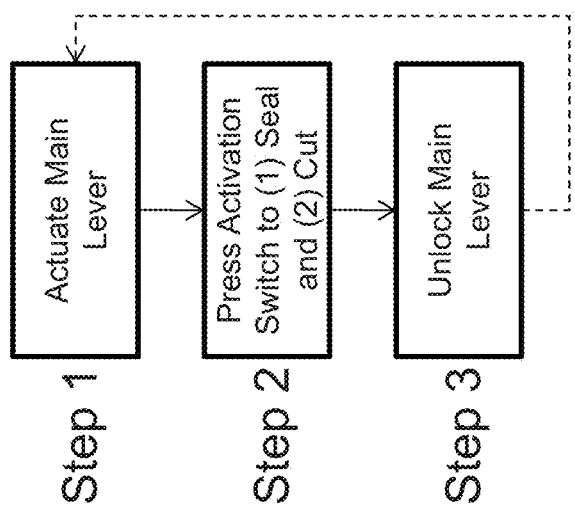
FIG. 66 is a process flow diagram illustrating the steps for operating one exemplary embodiment of an electrocautery sealing and cutting surgical device according to the present invention.
Figure 67:
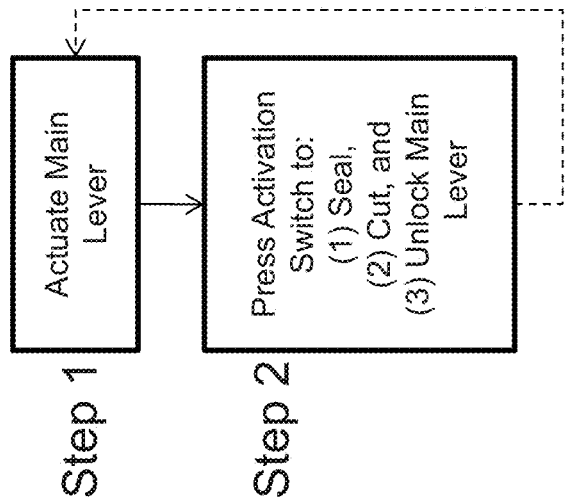
FIG. 67 is a process flow diagram illustrating the steps for operating another exemplary embodiment of an electrocautery sealing and cutting surgical device according to the present invention.

The embodiments discussed above each include manual actuation of the grasping and cutting sub-assemblies. FIGS. 54 to 60 illustrate an embodiment where the jaw movement mechanism is manual and the blade movement mechanism is electrically powered and controlled. FIGS. 61 to 64 illustrate an embodiment where the jaw and blade movement mechanisms are both electrically powered and controlled. Thus, any strenuous hand activity by the surgeon required during the cauterization/cutting procedure for prior art devices is substantially reduced or entirely eliminated. In all of these figures, the end effector is removed for clarity. FIGS. 65 to 67 illustrate how the electronically controlled grasping and cutting device of the present invention reduces the number of steps required to carry out a single cauterization/cutting procedure.

In the exemplary embodiment of the blade-powered device 5400 of FIGS. 54 to 57, a non-illustrated removable battery is inserted into a battery compartment 5405 within a handle portion 5404 of the device 5400. A jaw control trigger 5410 is pivotally connected to the device 5400 and has a flange 5412 pivotally connected to an end of a jaw control rod 5490. Thus, pivoting movement of the jaw control trigger 5410 causes a longitudinal translation movement of the jaw control rod 5490. The jaw control rod 5490 is longitudinally connected to a manual jaw slide 5492, which is shown by itself in FIG. 55. Behind the mount 5494 is a connection that causes a corresponding translation of the jaw actuator 1390 with any movement of the manual jaw slide 5492.

Figure 56:
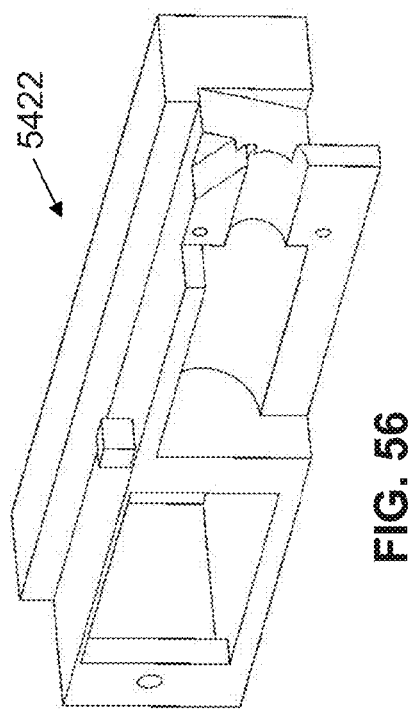
FIG. 56 is a perspective view from above a side of a blade control slide of the device of FIG. 54.
Figure 55:
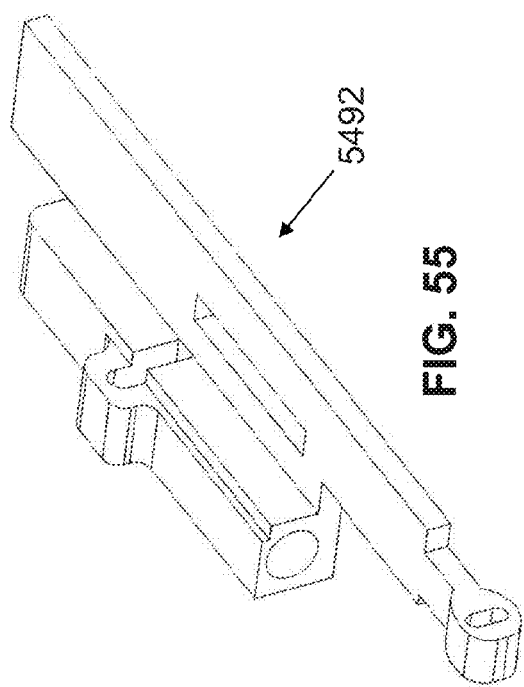
FIG. 55 is a perspective view from above a side of a jaw control slide of the device of FIG. 54.
Figure 57:
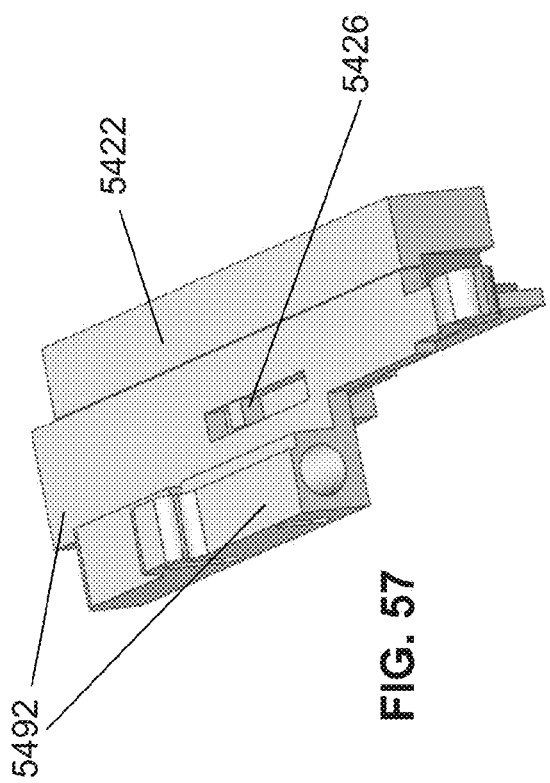
FIG. 57 is a perspective view from above a side of the jaw and blade control slides of FIGS. 55 and 56.

The manual jaw slide 5492 is slidably disposed upon a blade control slide 5422, shown by itself in FIG. 56. Both the manual jaw slide 5492 and the blade control slide 5422 are shown separate from the device 5400 in FIG. 57. As shown in FIG. 57, the blade control slide 5422 has a protruding boss 5426 that allows interaction of the blade control slide 5422 with the manual jaw slide 5492. In particular, closing of the jaws by a distal movement of the manual jaw slide 5492 results in a partial distal movement of the blade control slide 5422.

Figure 58:
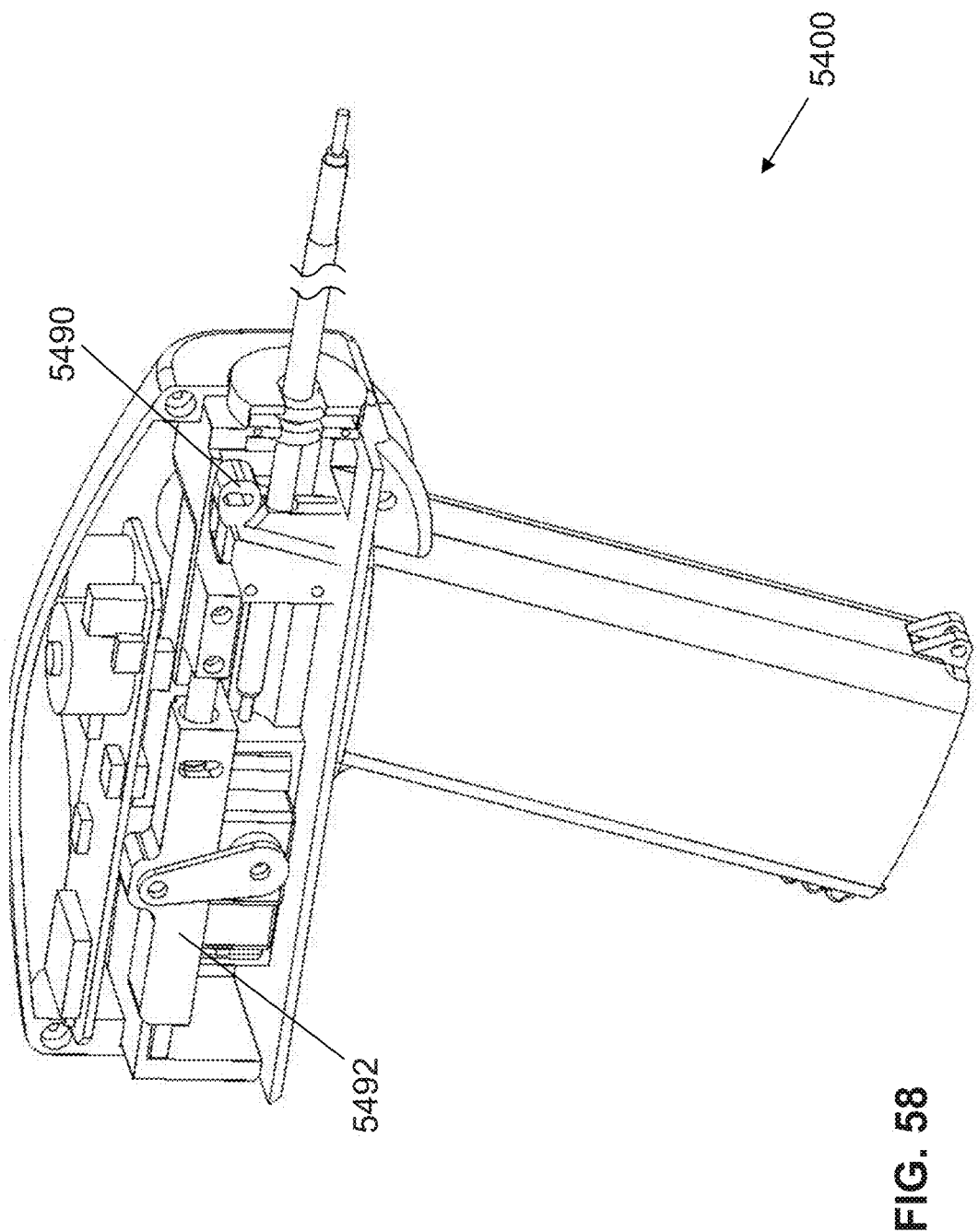
FIG. 58 is a fragmentary, perspective view of the device of FIG. 54 in a jaw-open and blade-retracted state with a control trigger removed.
Figure 59:
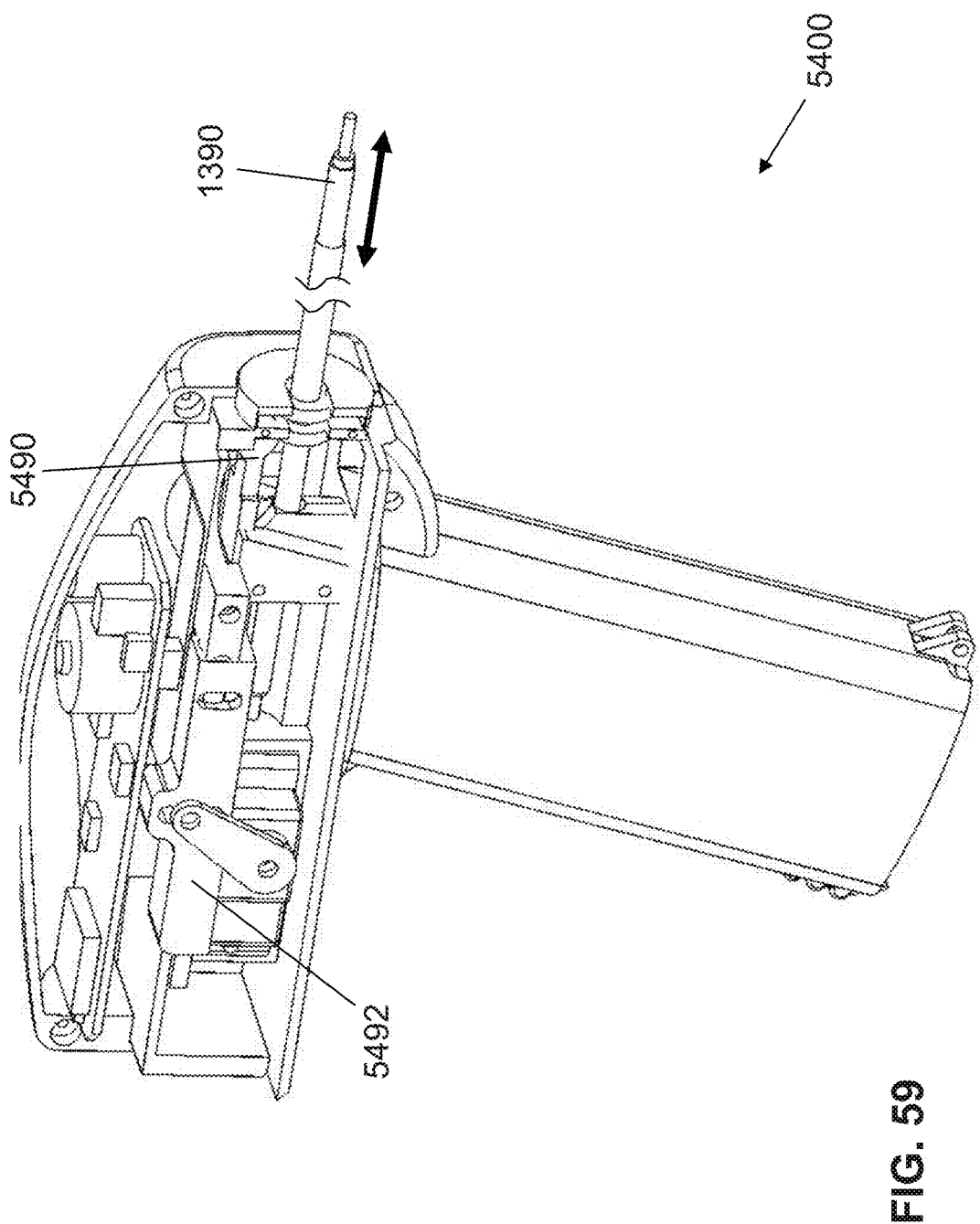
FIG. 59 is a fragmentary, perspective view of the device of FIG. 58 in a jaw-closed and blade-retracted state.
Figure 60:
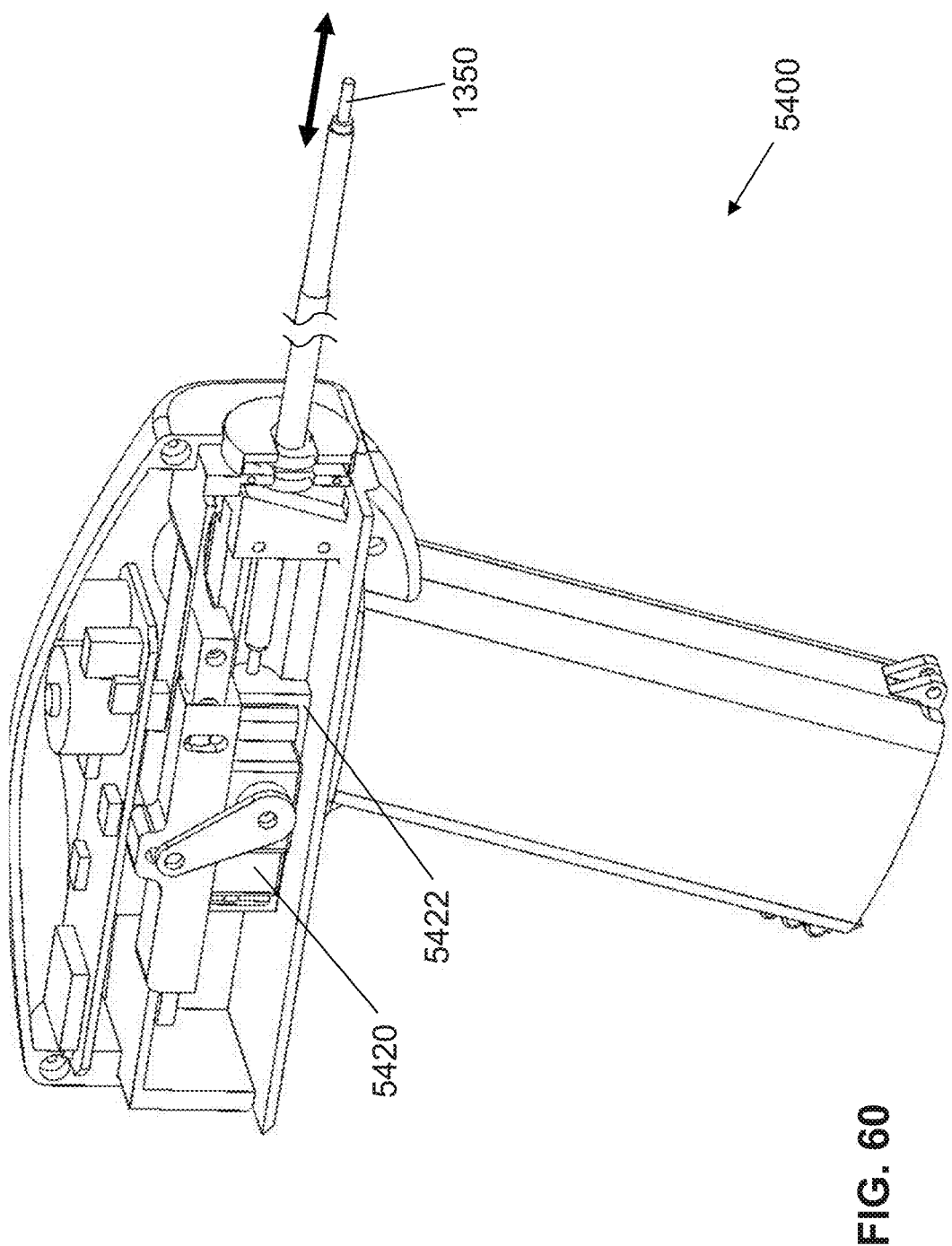
FIG. 60 is a fragmentary, perspective view of the device of FIG. 59 in a jaw-closed and blade-extended state.
Figure 61:
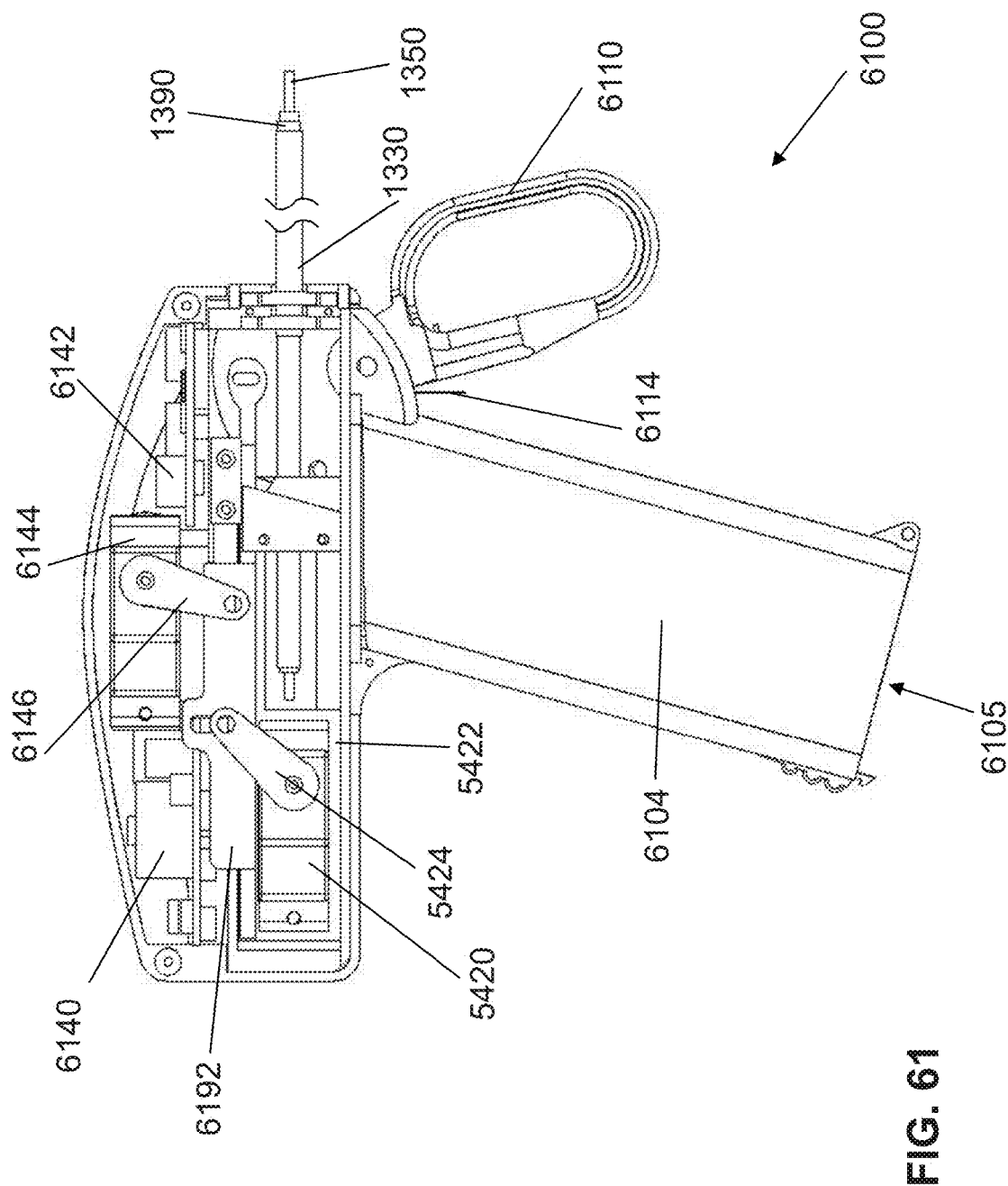
FIG. 61 is a fragmentary, side elevational view of another exemplary embodiment of a powered-blade electrocautery and cutting device according to the present invention

Movement of these parts and control of the both the blade and jaw mechanisms are illustrated in FIGS. 58 to 60. In FIG. 58, the jaw control trigger 5410 is removed. In the proximally disposed orientation of both the manual jaw slide 5492 and the blade control slide 5422 in FIG. 58, the jaws are open and the blade is retracted. With a depression of the jaw control trigger 5410, the jaw control rod 5490 moves distally, causing the jaw actuator 1390 to move distally and close the jaws. The jaw control trigger 5410 has a sensor 5414 that detects a fully depressed position thereof. When this sensor 5414 (e.g., a microswitch) is actuated or detects the fully depressed position, a jaws-closed state is recognized, thereby indicating that the blade can be moved safely within the jaws of the end effector. As such, electronics 5440 connected to the sensor 5414 powers the cautery device to deliver energy to the tissue disposed between the jaws. When the cauterization process is complete, tissue cutting can commence. The electronics 5440 detects this state and actuates a blade control servo 5420. In the exemplary embodiment shown, actuation of the blade control servo 5420 causes a counter-clockwise rotation of the blade movement crank 5424, which, due to the steady positioning of the manual jaw slide 5492, allows the blade control slide 5422 (along with the blade control servo 5420) to move distally from the blade-retracted position shown in FIG. 59 to the blade-extended position shown in FIG. 60. Other non-illustrated microswitches and/or circuitry can detect a completed blade extension and, thereafter, cause the blade control servo 5420 to reverse (clockwise movement) and, thereby, withdraw the blade from the cauterized tissue disposed between the jaws to complete the tissue cutting process. As shown, the blade movement crank 5424 remains substantially still as the jaws are closed.

A return spring 5496 can be disposed to bias the jaw control rod 5490 distally to, thereby, cause jaw separation when the surgeon is not depressing the jaw control trigger 5410. Similarly, the blade control slide 5422 can be biased (e.g., spring-loaded) in a proximal direction to keep the blade in the retracted position when at a steady state and to assist in removal from cauterized tissue between the jaws when stuck thereto.

In the exemplary embodiment of the jaw-and-blade-powered device 6100 of FIGS. 61 to 64, a non-illustrated removable battery is inserted into a battery compartment 6105 within a handle portion 6104 of the device 6100. A jaw control trigger 6110 is pivotally connected to the device 6100 but, in this embodiment, has no mechanical connection to control of the jaws. Instead, all control of the jaws occurs through a sensor 6114 that detects one or more depressed positions of the jaw control trigger 6110. When this sensor 6114 (e.g., a single or multi-position microswitch) is actuated or detects a partially depressed position, it sends a signal corresponding to the state of compression to jaw control circuitry 6142, which, in turn, controls movement of a jaw-movement servo 6144.

If jaw control is dependent only upon a fully closed jaw control trigger position, then the servo 6144 moves the jaws from the open to closed position when the jaw control trigger 6110 is fully depressed. On the other hand, if jaw control is dependent upon a relative jaw control trigger position, then the servo 6144 moves the jaws between the jaw-open to jaw-closed position corresponding to a degree of depression of the jaw control trigger 6110. Either way, the circuitry 6142 causes the jaw control servo 6144 to rotate the jaw movement crank 6146 (e.g., counter-clockwise) and move the automatic jaw slide 6192 distally to effect distal movement of the jaw actuator 1390, which, in turn, closes the jaws. Thus, pivoting movement of the jaw control trigger 6110 causes a corresponding electronically controlled and regulated translation of the jaw actuator 1390. With appropriately positioned non-illustrated force sensors, control of the jaw-movement servo 6144 can be regulated to prevent compression force upon tissue disposed between the jaws from exceeding a certain pre-set maximum value (and, conversely, can be regulated to insure compression force upon tissue disposed between the jaws exceeds a certain pre-set minimum value).

The automatic jaw slide 6192 is slidably disposed upon a blade control slide 5422 in the device 6100. As in the blade-powered assembly of FIGS. 54 to 60, closing of the jaws by distal movement of the automatic jaw slide 6192 results in a partial distal movement of the blade control slide 5422.

Figure 62:
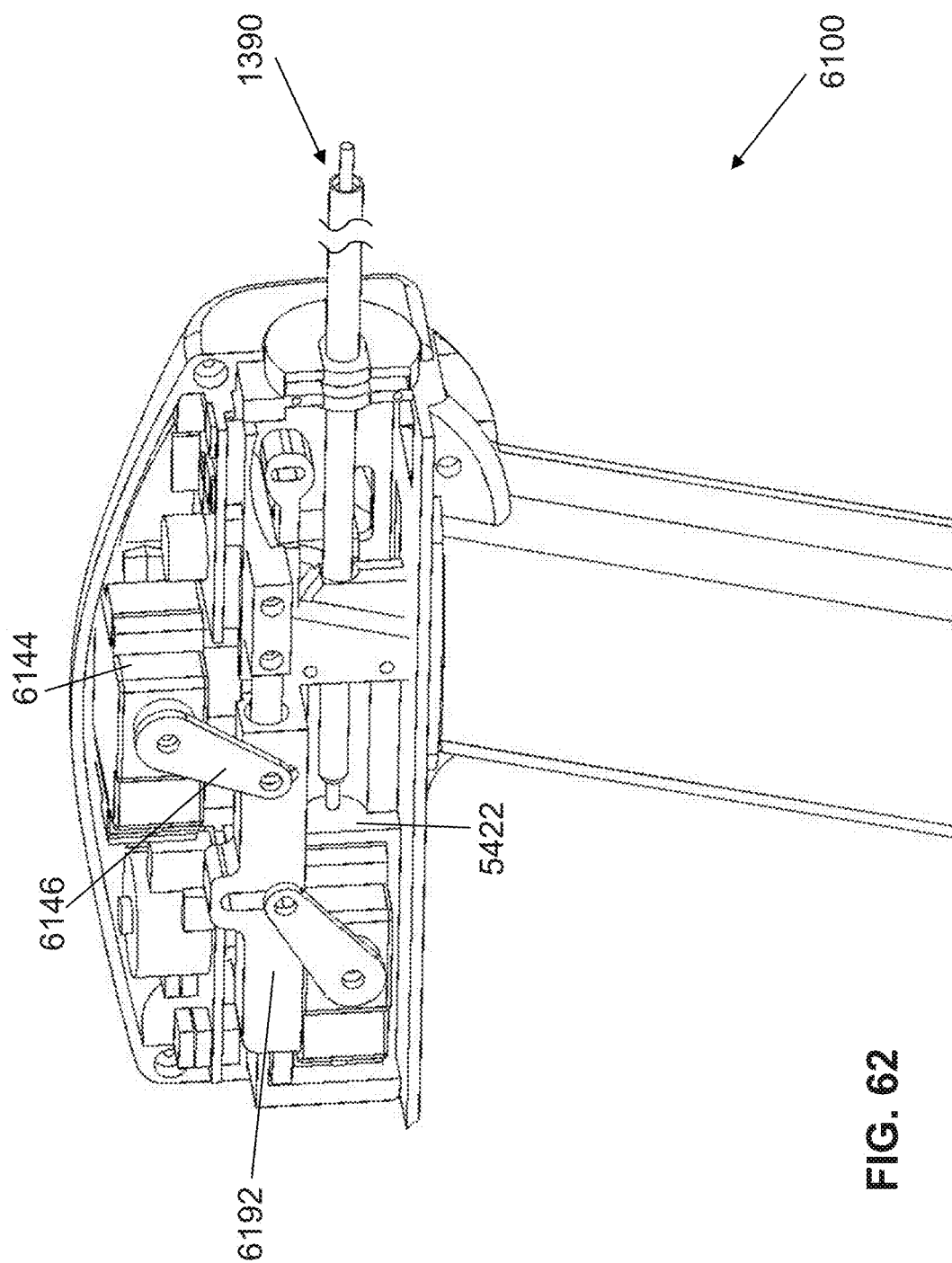
FIG. 62 is a fragmentary, perspective view of the device of FIG. 61 in a jaw-open and blade-retracted state with a control trigger removed.
Figure 63:
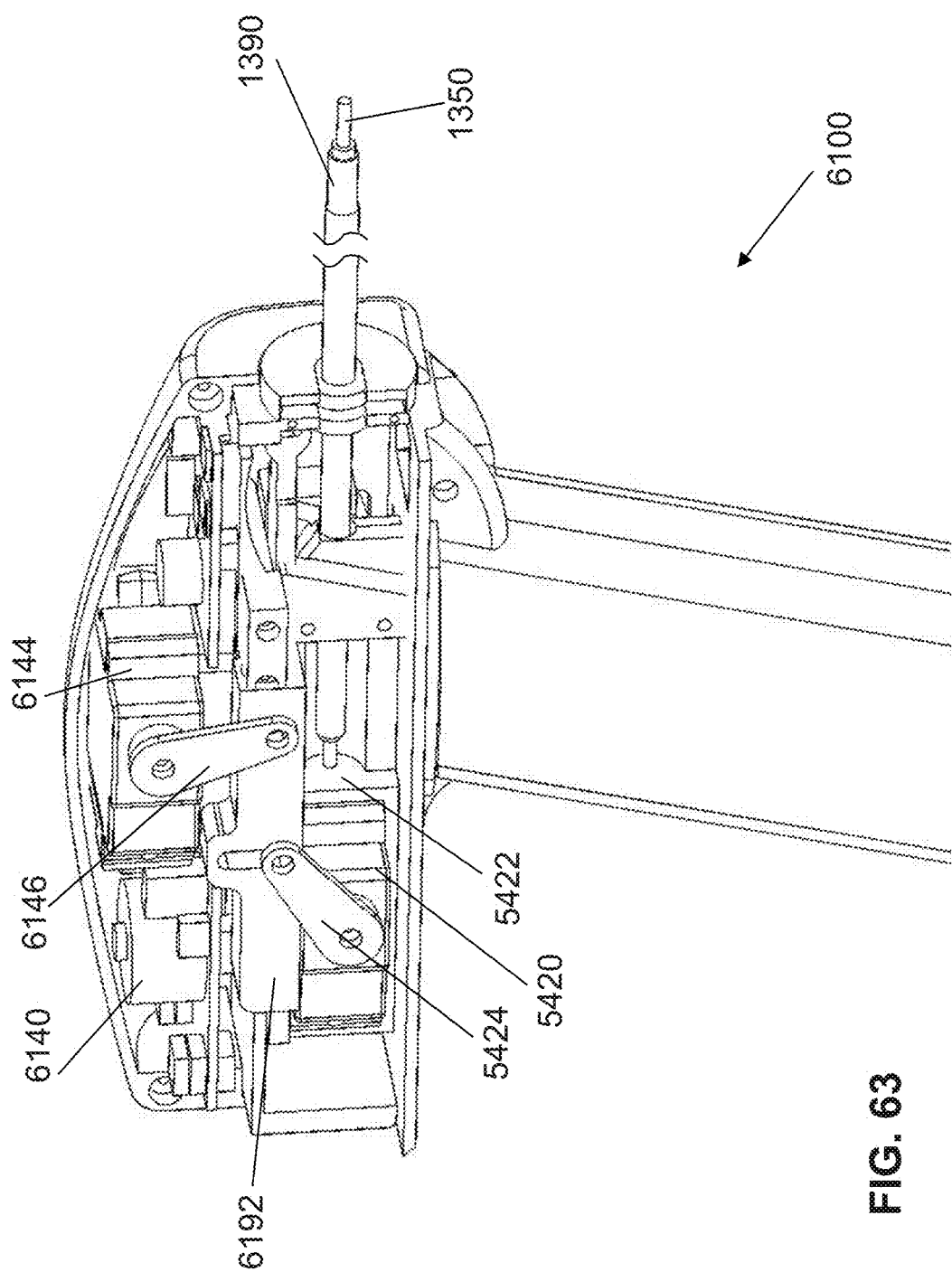
FIG. 63 is a fragmentary, perspective view of the device of FIG. 62 in a jaw-closed and blade-retracted state.
Figure 64:
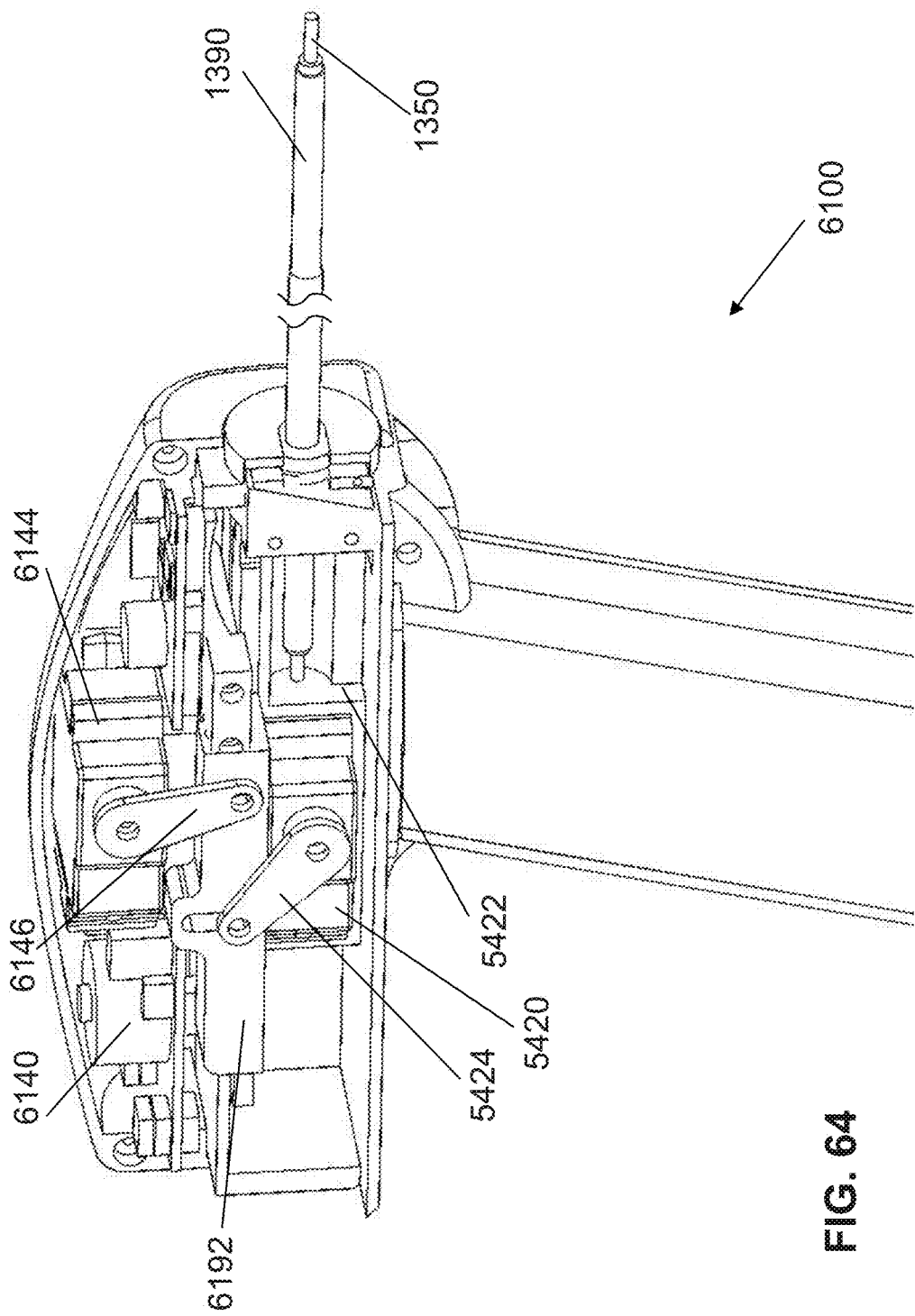
FIG. 64 is a fragmentary, perspective view of the device of FIG. 63 in a jaw-closed and blade-extended state.

Movement of these parts and control of the both the blade and jaw mechanisms are illustrated in FIGS. 62 to 64, in which, the jaw control trigger 6110 is removed for clarity. In the proximally disposed orientation of both the automatic jaw slide 6192 and the blade control slide 5422 in FIG. 62, the jaws are open and the blade is retracted. With a depression of the jaw control trigger 6110, the jaw control circuitry 6142 causes the jaw control servo 6144 to move the automatic jaw slide 6192 distally, causing the jaw actuator 1390 to move distally and close the jaws, as shown from the progression from FIG. 62 to FIG. 63.

With the jaws in a closed position (which can be detected by the circuitry 6142), cautery electronics 6140, also connected to the sensor 6114 and/or the jaw movement circuitry 6142, power the cautery portions of the jaws to deliver energy to the tissue disposed therebetween. When the cauterization process is complete, tissue cutting can commence. The cautery electronics 6140 detects this end state and actuates a blade control servo 5420. In the exemplary embodiment shown, actuation of the blade control servo 5420 causes a counter-clockwise rotation of the blade movement crank 5424, which, due to the steady positioning of the automatic jaw slide 6192, allows the blade control slide 5422 (along with the blade control servo 5420) to move distally from the blade-retracted position shown in FIG. 63 to the blade-extended position shown in FIG. 64. Other non-illustrated microswitches and/or circuitry can detect a completed blade extension and, thereafter, cause the blade control servo 5420 to reverse (clockwise movement) and, thereby, withdraw the blade from the cauterized tissue disposed between the jaws to complete the tissue cutting process. As shown, the blade movement crank 5424 remains substantially still as the jaws are closed.

A return spring can be disposed to bias the jaw and blade servos 5402, 6144 proximally to, thereby, cause jaw separation and retraction of the blade when the surgeon is not depressing the jaw control trigger 6110 and/or to assist in removal of the blade from cauterized tissue between the jaws when stuck thereto.

The exemplary embodiments with servo-controlled blade and/or jaw assemblies are shown herein only with the power generation circuitry in the handle. Nonetheless, these embodiments should not be considered limiting. All of the alternative and/or additional embodiments mentioned herein are applicable in any combination to each of these embodiments, for example, some circuitry can be placed in the battery itself or in a removable cartridge.

The actuation assemblies of the present invention reduce the number of steps to effect the sealing and cutting surgical procedure. This improvement is illustrated and explained with respect to FIGS. 65 to 67. To begin, FIG. 67 illustrates four steps that are needed to perform a prior art electrocautery sealing and cutting procedure. With the device jaws in a normally open position, in Step 1, the surgeon closes the jaws by actuating a main lever. With the first pulling motion, the jaws close and impart the sealing force to the tissue or vessel. In Step 2, the surgeon actuates electrocautery and seals the tissue. In Step 3, the surgeon pulls a trigger to move the cutting blade distally and the sealed tissue is cut. Typically, the blade is retracted upon release of the trigger. The surgeon, in Step 4, unlocks the main lever and, if desired, can repeat the process (dashed line). Each of Steps 1, 3 and 4, requires the surgeon to expend a significant amount of energy with his/her hand. For surgical procedures taking a long time and requiring a number of such sealings/cuttings, the surgeon can become tired.

The device of the invention, in contrast, dramatically reduces the forces required to effect the surgical procedure and, at the same time, reduces the total number of steps for completing the procedure—the combination of which conserves energy needed to carry out procedures over extended periods of time. This reduction is illustrated and explained with respect to FIGS. 66 and 67. To begin the inventive procedure, the surgeon closes the jaws in Step 1 by actuating a main lever 5410, 6110 of the device. With this first pulling motion, the jaws close and impart a first intermediate sealing force to the tissue or vessel. Thereafter, in Step 2, the surgeon makes a single actuation (e.g., presses a button, moves a toggle, rolls a wheel) on the device and the entire surgical procedure is carried out automatically. With respect to a configuration where the unlocking of the main lever is manual, only the sealing and cutting is performed automatically in Step 2. The main lever is unlocked by the surgeon in Step 3. In contrast, when the main lever is also electrically operated, both Steps 2 and 3 of FIG. 66 are performed with no other action than pressing the procedure-actuation switch, which is not illustrated but can be positioned on the side of the handle body similar to the button 4240 in FIG. 42.

It is beneficial if electrocautery is effected when tissue is at an optimal state for a desirable medical change to occur after the sealing and cutting procedure. Therefore, within the steps of compressing the tissue and carrying out electrocautery for sealing (but before cutting), these exemplary devices can be configured to carry out an OTC-determination step. This determination can be carried out in various ways. In one exemplary embodiment according to the invention, electrodes on either side of the tissue sense an impedance of the tissue disposed between the jaws (e.g., at the jaw mouth surfaces). OTC can be determined by comparing the measured impedance to a known range of impedances value corresponding to an OTC state of the tissue. As the tissue desiccates, the impedance of the tissue changes. Therefore, the active feedback circuitry can be provided to continuously monitor the impedance and to indicate to the surgeon to open or close the jaws accordingly (with appropriate indicators at the control handle, e.g., ↑=open or ↓=close) so that the OTC state is maintained up to and including the time that sealing and cutting is performed. But, with the servo-controlled jaw movement assembly shown in FIGS. 61 to 64, the jaw movement circuitry 6142 can be programmed to open or close the jaws with speed, precision, and accuracy.

The OTC feedback device performs particularly well when coupled to a mechanism for closing and opening the jaws. Passing an upper OTC value in a positive direction means that too much pressure is being imparted on the tissue and the motorized jaws are opened to an extent that brings the measured value back within the OTC range. In contrast, passing the lower OTC value in a negative direction means that too little pressure is being imparted on the tissue and the motorized jaws are closed to an extent that brings the measured value back within the OTC range. This self-adjusting compression device keeps compression force on the interposed tissue within the OTC compression range during and after desiccation. When in the OTC range after desiccation, the device notifies the surgeon of this fact, referred to as a "procedure-ready state." With this information, a delay can be pre-programmed in the device so that the sealing does not occur until after a time period expires, for example, any amount of time up to 5 seconds. In one exemplary embodiment, if the actuation device is pressed again, then the procedure is aborted and the surgeon can reposition the jaws or entirely abort the operation. If the surgeon does nothing during the delay period, then the device automatically starts the sealing procedure. Indicating information for the procedure-ready state can be conveyed to the surgeon audibly (e.g., with a speaker), visually (e.g., with an LED), or tactilely (e.g., with a vibration device).

Immediately after the tissue is sealed, embodiments of the device automatically start the cutting procedure by powering the blade from its retracted position to its extended position. Without any further activation or movement by the surgeon, the blade is, then, returned to its retracted position to complete the sealing/cutting procedure. In an exemplary embodiment, the retraction can be activated by appropriately positioned limit switches that are disposed in the blade-movement area to be contacted at the appropriate time. Alternatively, the stroke of the powered extension/retraction device can be limited to go no further than desired limits. Endpoint switches can be coupled with a mechanical gearbox but use of the servo provides advantages because the servo can pulse modulate the speed and the distance of travel. Powered retraction insures both that the blade does not remain in the cut tissue and that the blade is fully retracted. If desired, a motorized assembly can be included to unlock the main lever after blade retraction, allowing the main lever to spring back to its original open position (for example, through the force of a bias device, such a spring).

Closing of the jaws and movement of the blade is, in an exemplary embodiment, carried out utilizing one or more servos. One embodiment described above included a partial servo assembly where the jaws are controlled by hand and the knife is controlled by servo. However, another exemplary partial servo embodiment can provide an assembly where the jaws are controlled by the servo and the knife is controlled manually. Both movements are executed by moving an object, such as a rod or a beam, along the longitudinal axis of the device. By appropriate placement of one or more servos, these objects are connected directly to distal end of the servo arm (or via an intermediate linkage system). Thus, actuation of the respective servo moves the control rod longitudinally along the axis of the device. The range of the jaw-servo can be between the fully closed and fully opened orientation of the jaws. The jaw-servo can control the jaws whether the device is a single-moving jaw assembly or a dual-moving jaw assembly. If desired, two jaw-servos can independently operate the dual-moving jaw assembly. Either way, by controlling the jaw(s) with a servo, exact control of the jaws is made possible and, with a connection to an OTC feedback device, can permit exact and rapid jaw position control dependent upon measured values, e.g., voltage, current, tissue compression, tissue impedance, to name a few. Another beneficial advantage of servo-controlled jaw movement is that the servo can vary the jaw compressing force throughout the cutting procedure to further insure that the OTC range is maintained.

An advantageous feature that is provided by regulating the cutting blade with a servo is that the designer or even the surgeon can exactly regulate the speed of the cut. So, for example, if the surgeon knows that it would be beneficial for the speed of the cut to increase for a particularly tough compressed tissue, then the surgeon could turn a non-illustrated dial (for instance) that would effect a blade speed change.

The power-assisted actuation assembly of the present invention reduces the number of steps to carry out the surgical cautery/cutting procedure. With the jaws of the inventive device in the normally open position, the surgeon closes the jaws by actuating the jaw-closing trigger 5410, 6110. Like the prior art, this lever 5410, 6110 can have the pull-to-lock and pull-again-to-unlock actuation assembly. With this first pulling motion, the jaws close and impart a first intermediate sealing force to the tissue or vessel. This force need not be the final compressive force but merely can be an intermediate stage that securely holds the tissue therebetween. Thereafter, in a second step, the surgeon merely presses a single button on the device and the entire procedure is carried out automatically—the procedure including, for example, a determination of Optimal Tissue Compression (OTC), an electrocautery process to cause sealing of the tissue, a cutting movement through the sealed tissue, and a release of the jaws back to the intermediate stage. The process is finalized in the third step by a second pulling motion on the main lever to open the jaws fully. It is noted that, in another exemplary embodiment of the invention, the electronic control assembly can be configured to automatically actuate the main lever and, thereby, open the jaws for release of the sealed/cut tissue, making it ready for the next sealing/cutting procedure. With the invention, therefore, the surgeon can effect a sealing and cutting procedure with only two or three steps, these steps not requiring the surgeon to provide any significant external force (such as physically moving a trigger) other than initiating the first closure of the main lever.

As set forth in the preceding paragraph, the device of the instant invention is able to automatically compress the tissue at a pre-defined force that allows beneficial healing without irretrievably harming the compressed tissue. It is known that, when tissue is being compressed (whether a single layer or multiple layers) and before cutting the tissue, it is desirable for the tissue to be at a certain compressive state (OTC) so that a desirous medical change can occur; at the same time, the tissue should not be compressed too far to cause tissue necrosis. Because there is no way to precisely control the exact kind of tissue that is being placed within the compressing jaws, it is not possible to ensure manually that the tissue is compressed within an Optimal Tissue Compression range, referred to as an OTC range. Therefore, ruling out of tissue necrosis is difficult or not possible for prior art electrocautery devices.

As stated above with respect to FIG. 34, at least one power cell 3520 (e.g., a set of 2 to 6 lithium polymer cells having a high discharge current capacity on the order of 10 to 15 times the rated storage capacity (known as 10-15 C) is electrically connected to voltage control circuitry 3530, which can be, for example, a buck power supply controlling the output signal voltage. Radio-frequency signal generating circuitry 3540 receives the output signal and converts it into a high-frequency alternating-current signal, which AC signal is supplied to the end effector jaws through the conductive supply ports 3512 and the distribution panel 3410.

Figure 68:
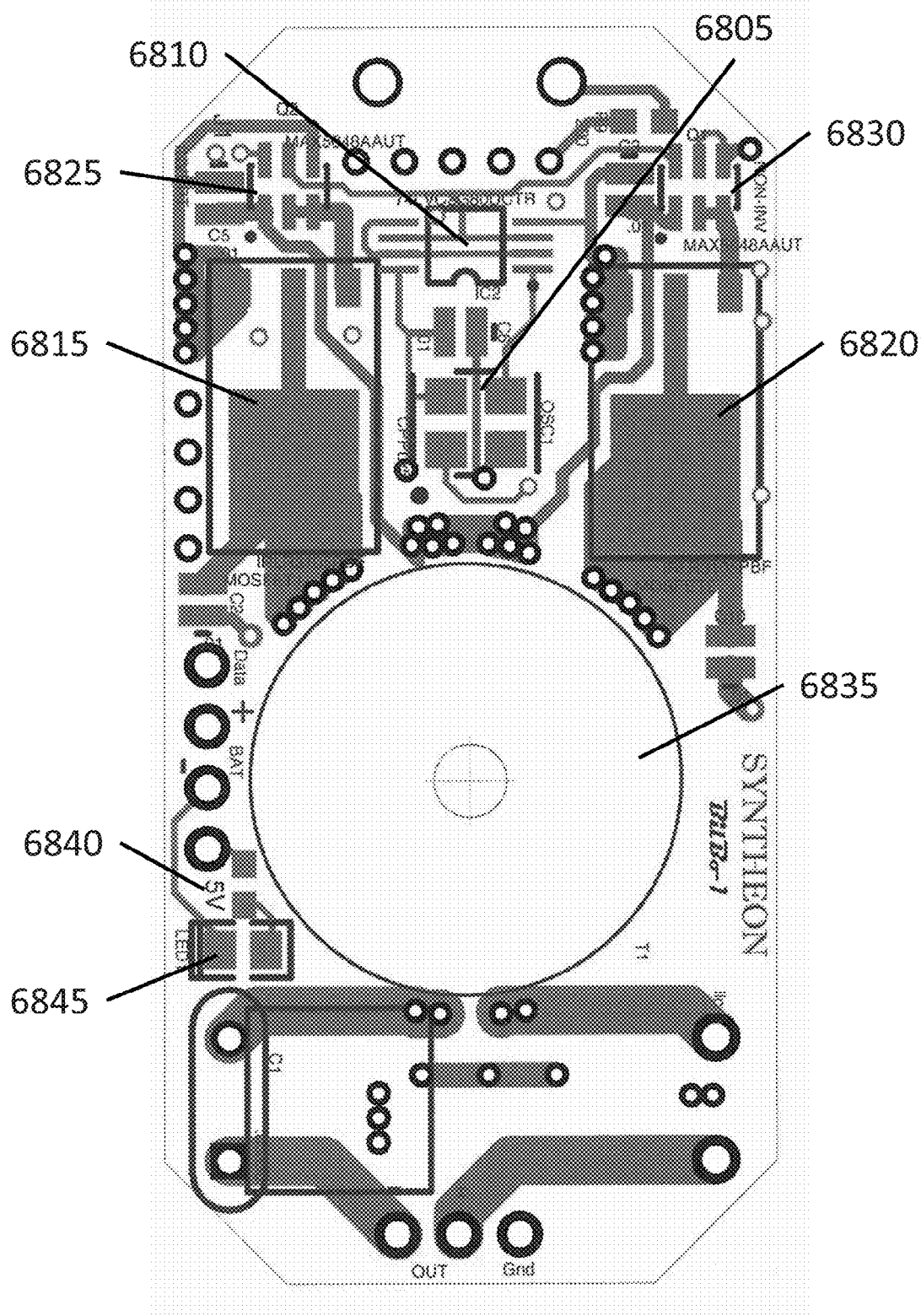
FIG. 68 is a plan view of a first layer of an exemplary embodiment of a four-layer circuit board.

FIGS. 68 to 71 illustrate an exemplary embodiment of radio-frequency signal generating circuitry 3540 with a four-layer board. FIG. 68 is the first layer of this four-layer circuit board. The first layer includes an oscillator 6805, a logic chip 6810, two MOSFETs 6815, 6820, and two MOSFET drivers 6825, 6830. The oscillator 6805 establishes the frequency. The logic chip 6810 creates a logic level signal to control the two MOSFET drivers 6825, 6830. Gates for the two MOSFETs 6815, 6820 are connected to each respective driver 6825, 6830. A control signal connects an inverting input of one MOSFET driver and a non-inverting input of the second MOSFET driver. The first layer also includes a 5V input 6840 that drives a light emitting diode (LED) 6845.

Figure 69:
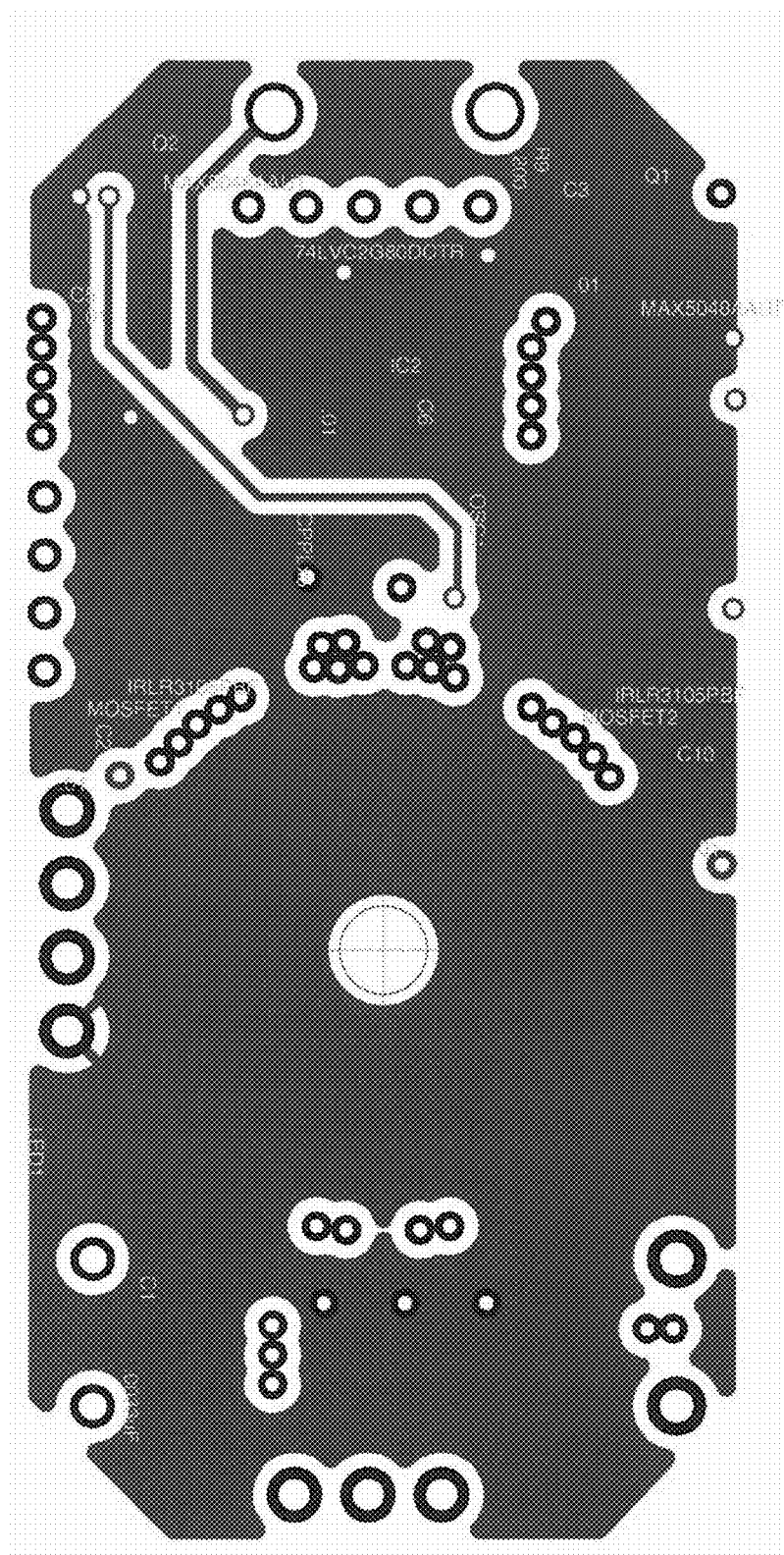
FIG. 69 is a plan view of a second layer of an exemplary embodiment of the four-layer circuit board.

FIG. 69 is a second layer of an exemplary embodiment of the four-layer circuit board. The second layer provides the 5V voltage (Vcc plane) to other layers of the board. The second layer provides voltage to the logic chip and the oscillator.

Figure 70:
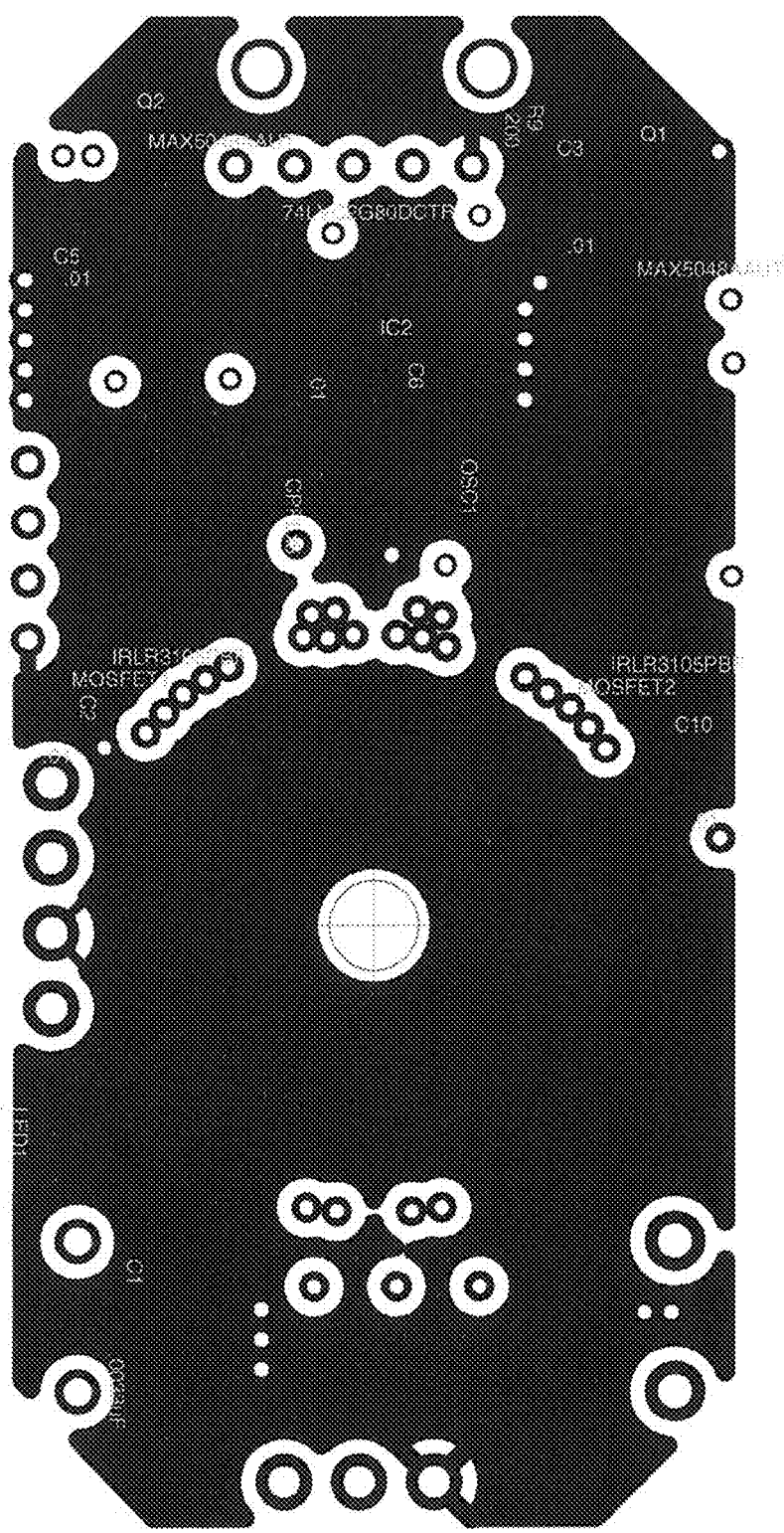
FIG. 70 is a plan view of a third layer of an exemplary embodiment of the four-layer circuit board.

FIG. 70 is a third layer of an exemplary embodiment of the four-layer circuit board. The third layer is the ground plane of the circuit board.

Figure 71:
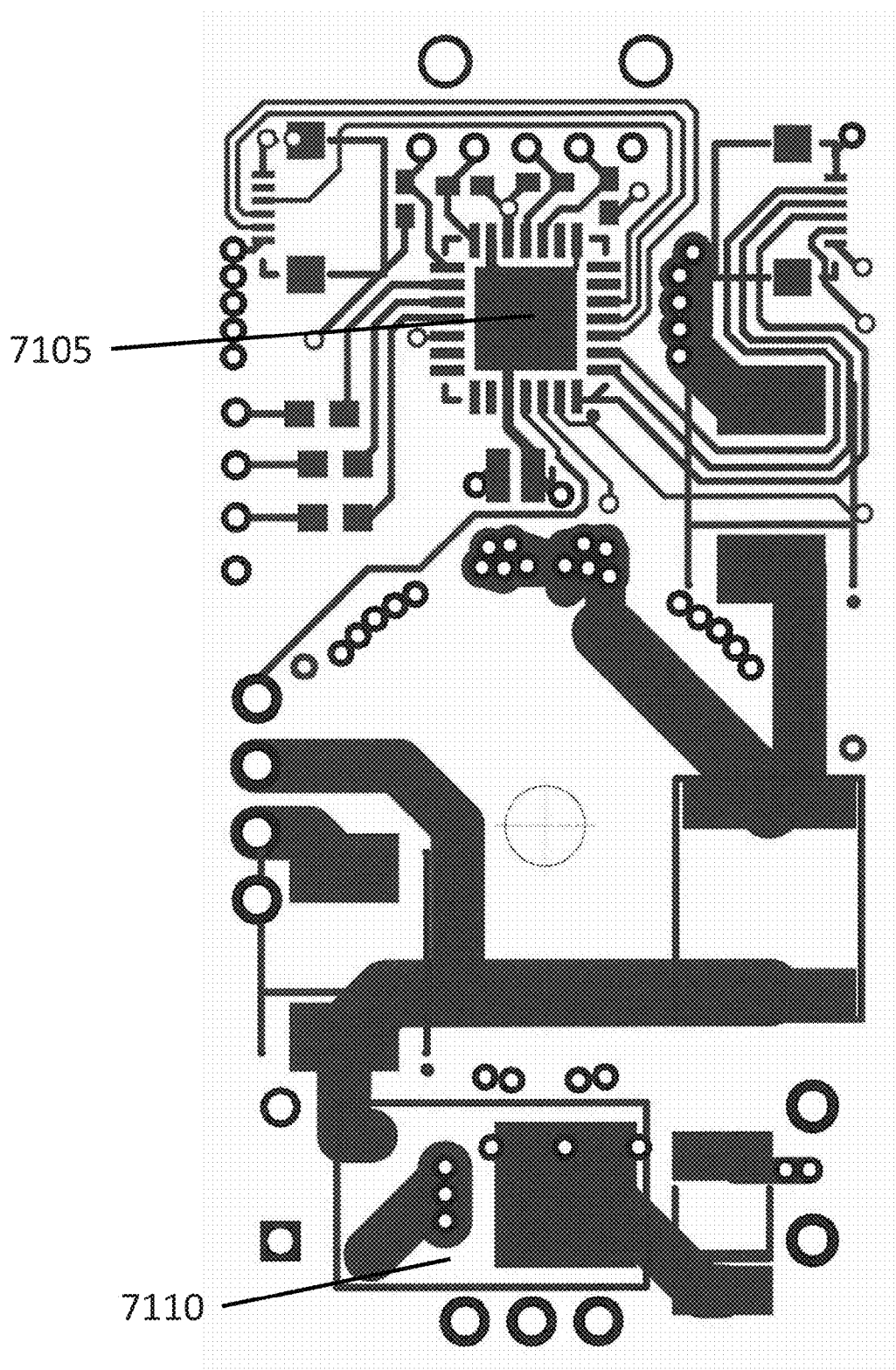
FIG. 71 is a plan view of a fourth layer of an exemplary embodiment of the four-layer circuit board.

FIG. 71 is a fourth layer of an exemplary embodiment of the four-layer circuit board. The fourth layer includes a programmable microcontroller 7105. The fourth layer also includes a 5V regulator 7110, which provides the Vcc voltage to the second layer. Buttons and other inputs can be connected to the available inputs on the programmable microcontroller 7105.

Figure 72:
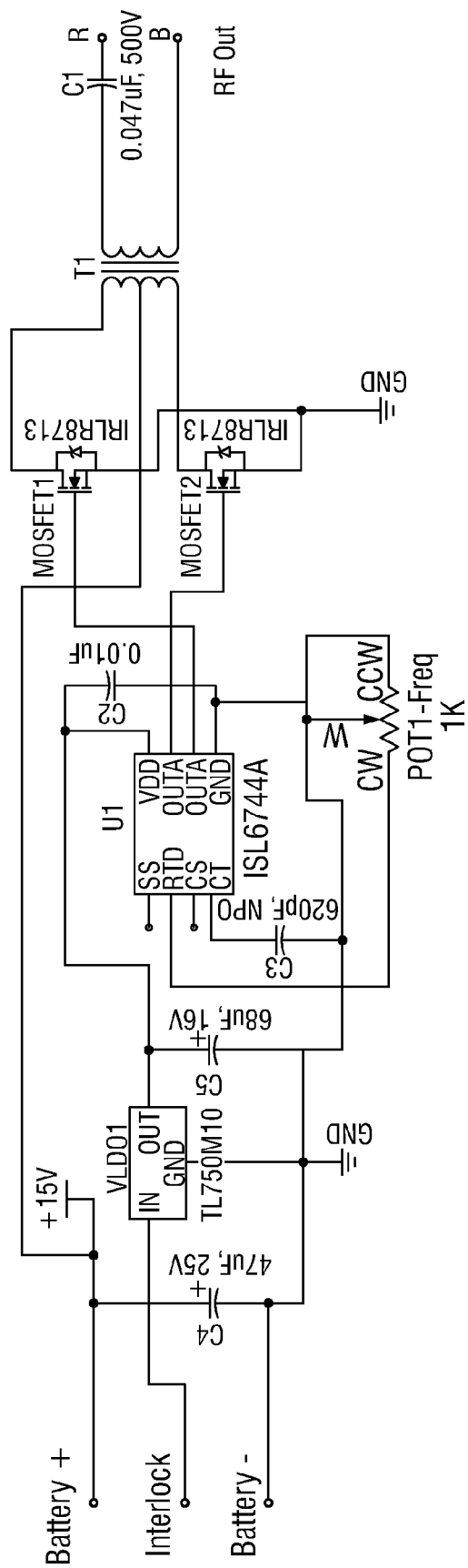
FIG. 72 is a circuit diagram of an exemplary embodiment of a radio-frequency generator.

FIG. 72 is a circuit diagram of an exemplary embodiment of a radio frequency (RF) generator, e.g., radio-frequency signal generating circuitry 3540, for a vessel sealer device. This circuit is used to receive DC input and provide AC output. The RF vessel sealer board has capacitors C1, C2, C3, C4, C5, a resistor POT1, two MOSFETs MOSFET1, MOSFET2, a voltage regulator VLDO1, a pulse width modulation controller U1, and a transformer T1. Direct current (DC) voltage is applied from a battery (e.g., 1880, 3500, 3600, 3880) to battery leads Battery+, Battery−. An interlock terminal controls power to the circuit through the voltage regulator. The main voltage (+15V) is applied to the center tap of the transformer.

The interlock is an input on the voltage regulator. The voltage applied to the interlock is 15V, e.g. full battery voltage. The output of the voltage regulator supplies DC voltage of about +8V to the oscillator and MOSFET driver.

Self-oscillating MOSFET driver U1 is implemented as a dual MOSFET driver. Output A of U1 drives MOSFET1 and Output B of U1 drives MOSFET2. U1 has its own oscillator. Therefore, U1 is able to establish its own frequency. Using the local oscillator, U1 can switch MOSFET1 and MOSFET2 on and off at the frequency generated by the oscillator.

C3 and POT1 are used to set the frequency of the oscillator. POT1 is connected to a resistance for time delay (RTD) port of the dual MOSFET driver U1. C3 is connected to an oscillator timing capacitor port, CT, of U1. In one exemplary embodiment, this frequency is set at about 300 kHz. The frequency is set at this level because it is a minimum frequency allowed by the Food and Drug Administration (FDA) for electro-surgery devices.

When the output for each respective MOSFET goes high, there is a delay to charge the MOSFET gate up because the input gate of MOSFET is, substantially, a capacitor. MOSFETs get hot during the time when they are switching from on to off. The goal is to switch the MOSFET on/off quickly. This is another reason why the lowest authorized frequency, i.e., 300 kHz, is selected for the oscillator of the dual MOSFET driver.

Only one MOSFET is active at a time. MOSFET1 grounds the top of transformer T1 and MOSFET2 grounds the bottom of transformer T1. The resulting output on the secondary, e.g., high voltage, side of the transformer T1 is an approximately 120V output, which is the product of the turns ratio of the transformer T1 and the output voltage of the voltage regulator. In one exemplary embodiment, the frequency of the voltage on the secondary side of the transformer T1 is approximately 300 kHz.

The capacitors C1, C2, C3, C4 serve various functions. C1 is optional and is placed between the transformer T1 and the output R/B. C1 is not required for the circuit but is placed therein to comply with FDA requirements, which require a capacitor in legacy devices (which had separate, plug in power supplies) in order to minimize low frequency leakage, i.e., to prevent 60 Hz current from going into the patient. In one exemplary embodiment, the value of C1 is 0.047 uF. C2 is a filter capacitor placed between voltage Vdd and ground. C2 is a bypass capacitor for controlling noise. In one exemplary embodiment, the value of C2 is 0.01 uF. As stated above, C3 is used to set the frequency of the oscillator in the dual MOSFET driver U1. In one exemplary embodiment, the value of C3 is 820 pF. C4 is used as an input filter on the battery and keeps noise from flowing upstream to the battery. In one exemplary embodiment, the value of C4 is 47 uF. C5 is used as an output filter on the voltage regulator. In one exemplary embodiment, the value of C5 is 68 uF.

Figure 73:
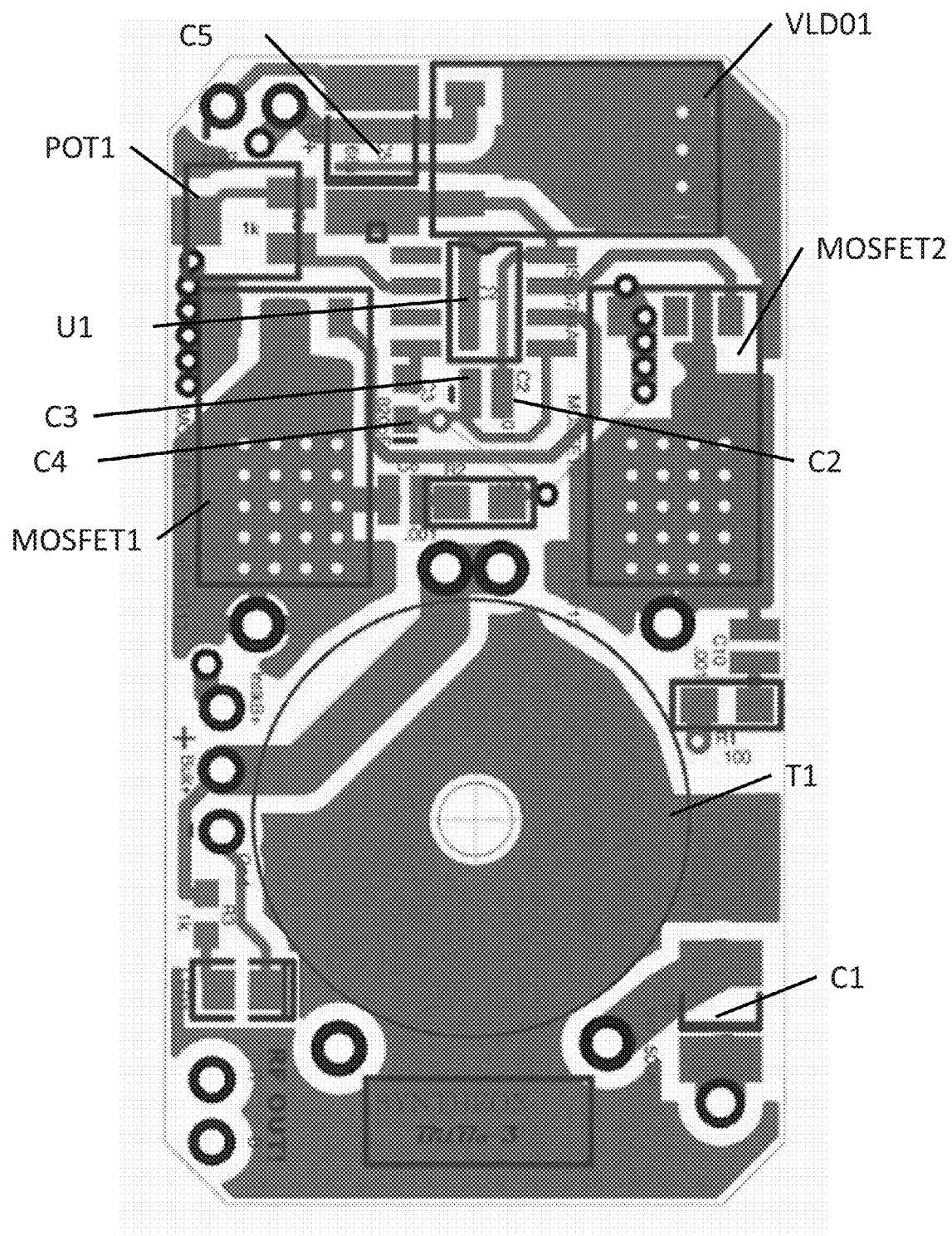
FIG. 73 is a plan view of a first layer of an exemplary embodiment of a two-layer circuit board.
Figure 74:
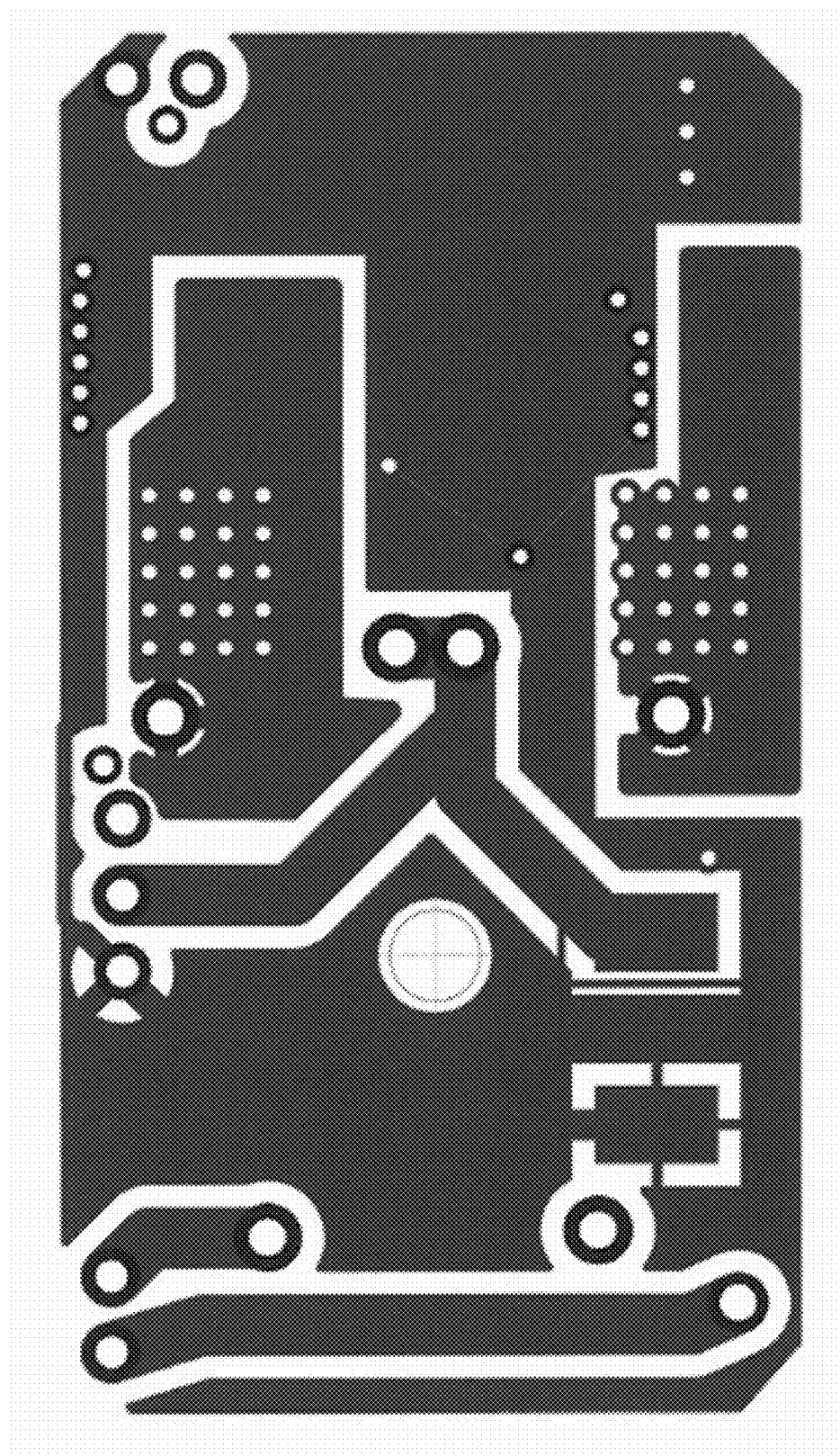
FIG. 74 is a plan view of a second layer of an exemplary embodiment of the two-layer circuit board.

FIGS. 73 and 74 illustrate a two-layer solution for a self-contained vessel sealer board implementing the circuit described with respect to FIG. 72. FIG. 73 is a first layer of an exemplary embodiment of this two-layer circuit board. The first layer of the RF vessel sealer board has capacitors C1, C2, C3, C4, C5, a resistor POT1, two MOSFETs MOSFET1, MOSFET2, a voltage regulator VLDO1, a pulse width modulation controller U1, and a transformer T1. The aforementioned elements operate as described above with respect to FIG. 72. Also included are resistors R1, R2, R3 and a capacitor C10 that are used for an optional microcontroller to provide overall control in some applications. FIG. 74 is a second layer of the exemplary embodiment of the two-layer circuit board. The second layer provides a position for C2, additional ground plane area, and some interconnections of the circuit.

The push-pull outlet with center tap provided by the two MOSFETS and the transformer is able to produce an output waveform with a full duty cycle output, i.e., a duty cycle 50% on and 50% off for each polarity, resulting in a low crest factor. Prior art devices are regulated by a pulse width modulator on the output, not a push-pull outlet. Devices using pulse width modulator regulation have a high crest factor, i.e., the peak output voltage is much greater than the average output voltage. This high crest factor results in more sparking and charring and, more importantly, less sealing with the instrument. Using the transformer T1 and the MOSFETs MOSFET1, MOSFET2 of the exemplary embodiments provides a much better seal without the problems inherent in the prior art devices. In addition, the circuit of the present invention is configured to be the smallest, simplest, and cheapest power supply for a Radio-Frequency generator. Thus, the circuit can be disposable if desired.

Figure 75:
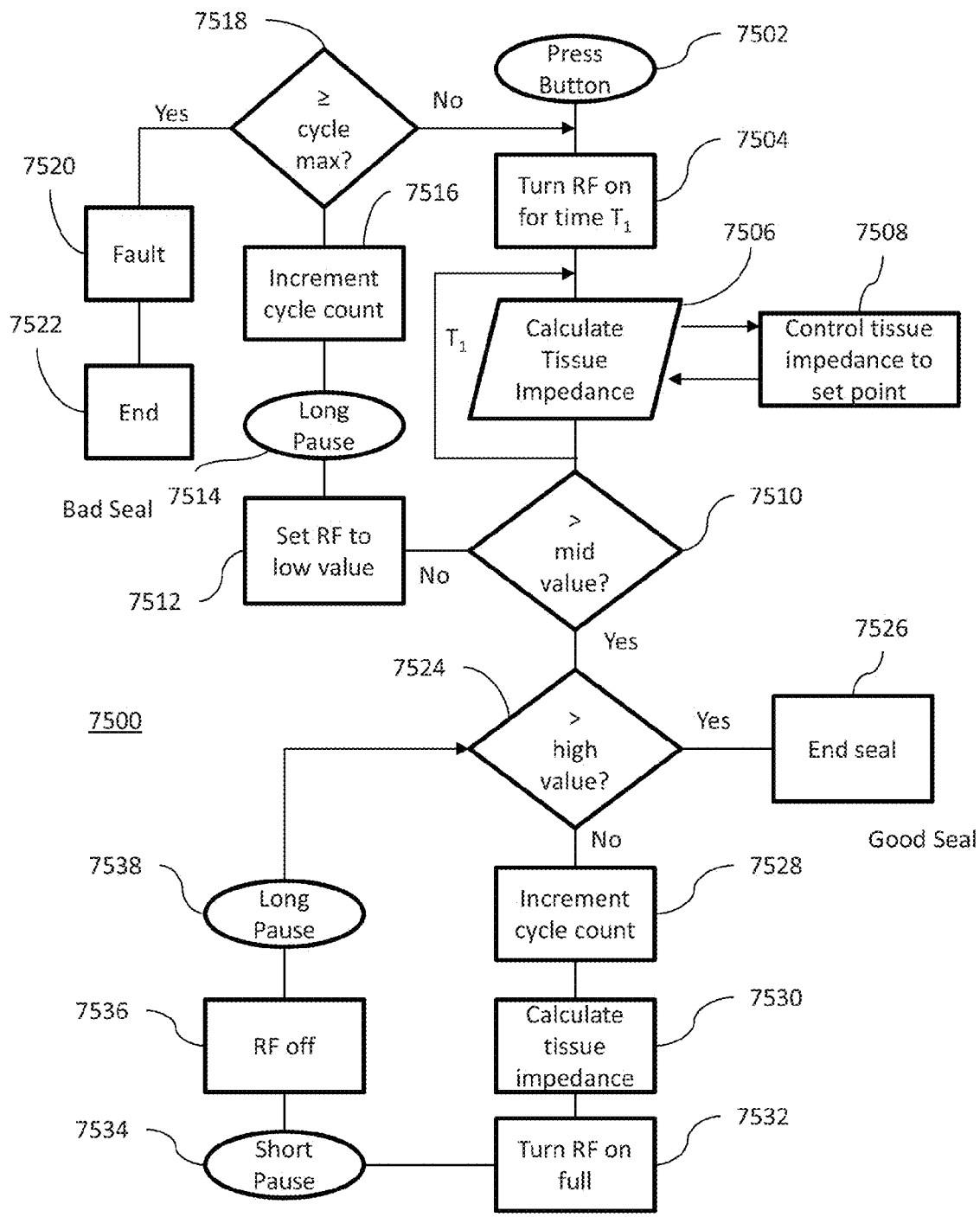
FIG. 75 is a process flow diagram illustrating steps for operating an exemplary embodiment of a method for providing RF tissue sealing.

FIG. 75 is a process flow diagram illustrating steps for operating an exemplary embodiment of a method for providing RF tissue sealing using the radio-frequency signal generating circuitry 3540. The process of method 7500 is used to control a switch mode power supply to provide power to a radio-frequency generator circuit in order to provide effective and improved vessel sealing. At block 7502, a user of the RF cautery and cutting device presses a button to apply RF energy across desiccating tissue (e.g., tissue clamped between the jaws of the vessel sealing end effector). At block 7504, radio-frequency generation occurs for time $T_1$. Tissue impedance is calculated over time $T_1$ at block 7506 until the tissue impedance reaches a certain point at block 7508. At block 7510, a determination is made as to whether the tissue impedance is greater than an intermediate value. If the tissue impedance is not greater than this intermediate value, the RF energy is set to a low value at block 7512. At block 7514, a long pause is introduced. At block 7516, the cycle count is incremented by incrementing the duty cycle of the input voltage. At block 7518, a determination is made as to whether the cycle count has been incremented to be greater than or equal to a cycle maximum. If the cycle maximum has been reached, the user is alerted that a fault has been detected at block 7520 and the process ends at block 7522. A fault is evidence of a bad seal. If the cycle maximum has not been reached, the process returns to block 7504.

If the tissue impedance is greater than the intermediate value, at block 7524, a determination is made as to whether a tissue impedance is greater than a high value. If the tissue impedance is greater than a high value, the sealing process ends at block 7526. High tissue impedance is evidence of a good seal.

If the tissue impedance is less than this high value, the cycle count is incremented at block 7528. Tissue impedance is calculated at block 7530. At block 7532, RF energy is set to a full value. At block 7534, a short pause is introduced. At block 7536, the RF energy is turned off. At block 7538, a long pause is introduced. After block 7538, the process returns to block 7524 to determine whether the tissue impedance is greater than a high value.

The foregoing description and accompanying drawings illustrate the principles, preferred embodiments and modes of operation of the invention. More specifically, the encrypted identification systems and methods according to the present invention have been described with respect to an inventory system and process. However, the invention should not be construed as being limited to the particular embodiments discussed above. Additional variations of the embodiments discussed above will be appreciated by those skilled in the art as well as for applications, unrelated to inventory, that require encrypted identification of parts.

The above-described embodiments should be regarded as illustrative rather than restrictive. Accordingly, it should be appreciated that variations to those embodiments can be made by those skilled in the art without departing from the scope of the invention as defined by the following claims.

We claim:

1. A circuit for generating a radio-frequency signal for a surgical device, comprising:
   a voltage regulator including a direct current (DC) voltage output;
   a first MOSFET including a first terminal, a second terminal, and a third terminal;
   a second MOSFET including a first terminal, a second terminal, and a third terminal, wherein the first terminal of the first MOSFET is coupled to the first terminal of the second MOSFET;
   a MOSFET driver including:
      an input coupled to the DC voltage output of the voltage regulator;
      a first output;
      a second output; and
      a local oscillator directly coupled to the second terminal of the first MOSFET by way of the first output of the MOSFET driver and directly coupled to the second terminal of the second MOSFET by way of the second output of the MOSFET driver; and
   a transformer including a first terminal, a second terminal, and a center tap, wherein the first terminal of the transformer is directly coupled to the third terminal of the first MOSFET, the second terminal of the transformer is directly coupled to the third terminal of the second MOSFET, and a main voltage is configured to be applied at the center tap.

2. The circuit according to claim 1, further comprising an interlock terminal configured to control power through the voltage regulator.

3. The circuit according to claim 1, wherein the DC voltage output of the voltage regulator is coupled to the local oscillator and to the MOSFET driver.

4. The circuit according to claim 1, wherein the MOSFET driver is configured to self-oscillate.

5. The circuit according to claim 4, wherein the MOSFET driver is a dual MOSFET driver.

6. The circuit according to claim 5, wherein the MOSFET driver is configured to establish the frequency of the local oscillator.

7. The circuit according to claim 6, further comprising a capacitor and a resistor connected to the local oscillator and having respective capacitance and resistance values that set a frequency of the local oscillator.

8. The circuit according to claim 7, wherein the MOSFET driver has a resistance for a time delay port connected to the resistor.

9. The circuit according to claim 8, wherein the MOSFET driver has an oscillator timing capacitor port connected to the capacitor.

10. The circuit according to claim 9, wherein the frequency is set to 300 kHz.

11. The circuit according to claim 1, wherein the first terminal of the transformer, in a first configuration, is coupled to ground by way of the third terminal of the first MOSFET.

12. The circuit according to claim 11, wherein the second terminal of the transformer, in a second configuration, is coupled to ground by way of the third terminal of the second MOSFET.

13. The circuit according to claim 12, wherein the output of the transformer is a product of a turns ratio of the transformer and the voltage supplied by the voltage regulator.

14. The circuit according to claim 13, wherein:
   the transformer has a secondary side; and
   the output of the transformer is at the secondary side and comprises an output voltage.

15. The circuit according to claim 14, wherein the output voltage on the secondary side of the transformer has a frequency of 300 kHz.

* * * * *